US011083537B2

(12) United States Patent
Tripathi et al.

(10) Patent No.: US 11,083,537 B2
(45) Date of Patent: Aug. 10, 2021

(54) STEREOSCOPIC CAMERA WITH FLUORESCENCE VISUALIZATION

(71) Applicant: Alcon Inc., Fribourg (CH)

(72) Inventors: Ashok Burton Tripathi, Santa Barbara, CA (US); Maximiliano Ramirez Luna, Santa Barbara, CA (US); George Polchin, Santa Barbara, CA (US); Thomas Riederer, Santa Barbara, CA (US); Alan Fridman, Goleta, CA (US)

(73) Assignee: Alcon Inc., Fribourg (CH)

( * ) Notice: Subject to any disclaimer, the term of this patent is extended or adjusted under 35 U.S.C. 154(b) by 66 days.

(21) Appl. No.: 16/552,297

(22) Filed: Aug. 27, 2019

(65) Prior Publication Data

US 2020/0008899 A1 Jan. 9, 2020

Related U.S. Application Data

(63) Continuation-in-part of application No. 16/422,204, filed on May 24, 2019, which is a continuation of (Continued)

(51) Int. Cl.
*A61B 9/00* (2006.01)
*A61B 90/00* (2016.01)
(Continued)

(52) U.S. Cl.
CPC .............. *A61B 90/37* (2016.02); *G02B 15/14* (2013.01); *G03B 5/00* (2013.01); *G03B 35/08* (2013.01);
(Continued)

(58) Field of Classification Search
CPC .. A61B 90/37; H04N 13/296; H04N 5/23212; H04N 5/23296; H04N 13/225;
(Continued)

(56) References Cited

U.S. PATENT DOCUMENTS 3,517,183 A 6/1970 Rebres
3,867,697 A 2/1975 Vanzetti et al.
(Continued)

FOREIGN PATENT DOCUMENTS

DE 3431992 4/1985
EP 0146476 A2 6/1985
(Continued)

OTHER PUBLICATIONS

US 3,973,836 A, 08/1976, Govignon et al. (withdrawn)
(Continued)

*Primary Examiner* — Tat C Chio
(74) *Attorney, Agent, or Firm* — Quinn IP Law

(57) ABSTRACT

A stereoscopic camera with fluorescence visualization is disclosed. An example stereoscopic camera includes a visible light source, a near-ultraviolet light source, and a near-ultraviolet light source. The stereoscopic camera also includes a light filter assembly having left and right filter magazines positioned respectively along left and right optical paths and configured to selectively enable certain wavelengths of light to pass through. Each of the left and right filter magazines includes an infrared cut filter, a near-ultraviolent cut filter, and a near-infrared bandpass filter. A controller of the camera is configured to provide for a visible light mode, an indocyanine green ("ICG") fluorescence mode, and a 5-aminolevulinic acid ("ALA") fluorescence mode by synchronizing the activation of the light sources with the selection of the filters. A processor of the camera combines image data from the different modes to enable fluorescence emission light to be superimposed on visible light stereoscopic images.

12 Claims, 36 Drawing Sheets

Related U.S. Application Data application No. 15/814,127, filed on Nov. 15, 2017, now Pat. No. 10,299,880.

(60) Provisional application No. 62/489,289, filed on Apr. 24, 2017, provisional application No. 62/489,876, filed on Apr. 25, 2017.

(51) Int. Cl.

| | |
|---|---|
| *H04N 13/296* | (2018.01) |
| *H04N 5/232* | (2006.01) |
| *G06T 19/00* | (2011.01) |
| *H04N 13/225* | (2018.01) |
| *H04N 13/236* | (2018.01) |
| *H04N 13/246* | (2018.01) |
| *H04N 13/254* | (2018.01) |
| *G02B 15/14* | (2006.01) |
| *G03B 5/00* | (2021.01) |
| *G03B 35/08* | (2021.01) |
| *G03B 35/10* | (2021.01) |
| *H04N 13/239* | (2018.01) |
| *H04N 13/156* | (2018.01) |
| *H04N 13/337* | (2018.01) |
| *H04N 13/183* | (2018.01) |
| *H04N 9/04* | (2006.01) |

(52) U.S. Cl.
CPC ............ *G03B 35/10* (2013.01); *G06T 19/006* (2013.01); *H04N 5/23212* (2013.01); *H04N 5/23296* (2013.01); *H04N 13/156* (2018.05); *H04N 13/225* (2018.05); *H04N 13/236* (2018.05); *H04N 13/239* (2018.05); *H04N 13/246* (2018.05); *H04N 13/254* (2018.05); *H04N 13/296* (2018.05); *G03B 2205/0046* (2013.01); *H04N 9/045* (2013.01); *H04N 9/04515* (2018.08); *H04N 13/183* (2018.05); *H04N 13/337* (2018.05)

(58) Field of Classification Search
CPC .. H04N 13/236; H04N 13/246; H04N 13/254; H04N 13/239; H04N 13/156; H04N 13/337; H04N 13/183; H04N 9/04515; H04N 9/045; H04N 13/15; H04N 13/161; H04N 2213/001; H04N 13/257; G06T 19/006; G02B 15/14; G02B 21/22; G03B 5/00; G03B 35/08; G03B 35/10; G03B 2205/0046; G03B 15/03; G03B 15/14
See application file for complete search history.

(56) References Cited

U.S. PATENT DOCUMENTS

| | | |
|---|---|---|
| 4,395,731 A | 7/1983 | Schoolman |
| 4,418,993 A | 12/1983 | Lipton |
| 4,691,997 A | 9/1987 | Munchel |
| 4,786,155 A | 11/1988 | Fantone et al. |
| 4,790,305 A | 12/1988 | Zoltan |
| 4,791,478 A | 12/1988 | Tredwell et al. |
| 4,967,268 A | 10/1990 | Lipton et al. |
| 4,989,078 A | 1/1991 | Paxton |
| 4,995,716 A | 2/1991 | Warnicki et al. |
| 5,007,715 A | 4/1991 | Verhhulst |
| 5,022,744 A | 6/1991 | Leiter |
| 5,045,936 A | 9/1991 | Lobb et al. |
| 5,048,946 A | 9/1991 | Sklar et al. |
| 5,054,907 A | 10/1991 | Sklar et al. |
| 5,098,426 A | 3/1992 | Sklar et al. |
| 5,109,276 A | 4/1992 | Nudelman et al. |
| 5,193,000 A | 3/1993 | Lipton et al. |
| 5,200,838 A | 4/1993 | Nudelman et al. |
| 5,513,005 A | 4/1996 | Muller et al. |
| 5,530,494 A | 6/1996 | Ogawa et al. |
| 5,545,120 A | 8/1996 | Chen et al. |
| 5,548,355 A | 8/1996 | Iki |
| 5,568,188 A | 10/1996 | Widmer et al. |
| 3,431,992 A | 12/1996 | Whitecar |
| 5,579,772 A | 12/1996 | Kinukawa et al. |
| 5,652,676 A | 7/1997 | Grinblat |
| 5,662,584 A | 9/1997 | Hori et al. |
| 5,715,836 A | 2/1998 | Kliegis et al. |
| 5,740,802 A | 4/1998 | Nafis et al. |
| 5,751,927 A | 5/1998 | Wason |
| 5,815,240 A | 9/1998 | Iki |
| 5,825,532 A | 10/1998 | Mochizuki et al. |
| 5,835,133 A | 11/1998 | Moreton et al. |
| 5,867,210 A | 2/1999 | Rod |
| 5,867,309 A | 2/1999 | Spink et al. |
| 5,870,137 A | 2/1999 | Stuettler |
| 5,873,822 A | 2/1999 | Ferre et al. |
| 5,912,763 A | 6/1999 | Spink et al. |
| 5,933,513 A | 8/1999 | Yoneyama et al. |
| 5,999,840 A | 12/1999 | Grimson et al. |
| 6,006,126 A | 12/1999 | Cosman |
| 6,069,733 A | 5/2000 | Spink et al. |
| 6,088,470 A | 7/2000 | Camus et al. |
| 6,133,762 A | 10/2000 | Hill et al. |
| 6,133,945 A | 10/2000 | Stuettler |
| 6,144,762 A | 11/2000 | Brooks |
| 6,147,797 A | 11/2000 | Lee |
| 6,179,421 B1 | 1/2001 | Pang |
| 6,191,809 B1 | 2/2001 | Hori et al. |
| 6,201,984 B1 | 3/2001 | Funda et al. |
| 6,241,672 B1 | 6/2001 | Hochman et al. |
| 6,256,529 B1 | 7/2001 | Holupka et al. |
| 6,276,799 B1 | 8/2001 | Van Sarloos et al. |
| 6,318,860 B1 | 11/2001 | Suzumura |
| 6,337,765 B1 | 1/2002 | Spink et al. |
| 6,396,627 B1 | 5/2002 | Tachihara et al. |
| 6,441,958 B1 | 8/2002 | Yeung et al. |
| 6,483,948 B1 | 11/2002 | Spink et al. |
| 6,522,906 B1 | 2/2003 | Salisbury, Jr. et al. |
| 6,596,025 B2 | 7/2003 | Portney |
| 6,607,527 B1 | 8/2003 | Ruiz et al. |
| 6,631,990 B2 | 10/2003 | Schippert et al. |
| RE38,307 E | 11/2003 | Gustafsson et al. |
| 6,643,070 B2 | 11/2003 | Deverin et al. |
| 6,675,032 B2 | 1/2004 | Chen et al. |
| 6,685,317 B2 | 2/2004 | Su et al. |
| 6,697,664 B2 | 2/2004 | Kienzle, III et al. |
| 6,765,718 B1 | 7/2004 | Spink et al. |
| 7,025,459 B2 | 4/2006 | Cornsweet et al. |
| 7,066,928 B2 | 6/2006 | Dick et al. |
| 7,110,614 B2 | 9/2006 | Launay et al. |
| 7,146,983 B1 | 12/2006 | Hohla et al. |
| 7,261,415 B2 | 8/2007 | Chernyak |
| 7,313,430 B2 | 12/2007 | Urquhart |
| 7,320,685 B2 | 1/2008 | Feige et al. |
| 7,331,667 B2 | 2/2008 | Grotehusmann et al. |
| 7,370,965 B2 | 5/2008 | Kojima et al. |
| 7,428,001 B2 | 9/2008 | Schowengerdt et al. |
| 7,431,457 B2 | 10/2008 | Chernyak |
| 7,654,668 B2 | 2/2010 | Neuhann et al. |
| 7,695,136 B2 | 4/2010 | Dai |
| 7,831,096 B2 | 11/2010 | Williamson, Jr. |
| 7,905,887 B2 | 3/2011 | Moeller et al. |
| 7,959,289 B2 | 6/2011 | Cattin-Liebl |
| 8,025,400 B2 | 9/2011 | Chernyak |
| 8,057,038 B2 | 11/2011 | Dai et al. |
| 8,088,124 B2 | 1/2012 | Loesel et al. |
| 8,131,343 B2 | 3/2012 | Burgkart |
| 8,186,830 B2 | 5/2012 | Grotehusmann et al. |
| 8,192,445 B2 | 6/2012 | Parmer et al. |
| 8,375,956 B2 | 2/2013 | Gray et al. |
| 8,414,123 B2 | 4/2013 | Boukhny et al. |
| 8,454,160 B2 | 6/2013 | Dai |
| 8,474,974 B2 | 7/2013 | Dai |
| 8,486,085 B2 | 7/2013 | Moeller et al. |
| 8,528,566 B2 | 9/2013 | Loesel et al. |
| 8,708,488 B2 | 4/2014 | Kraus |

(56) References Cited

U.S. PATENT DOCUMENTS

| | | |
|---|---|---|
| 8,740,385 B2 | 6/2014 | Chernyak |
| 8,784,443 B2 | 7/2014 | Tripathi |
| 8,848,869 B2 | 9/2014 | Gertner et al. |
| 8,978,660 B2 | 3/2015 | Chernyak et al. |
| 2002/0063850 A1 | 5/2002 | Barry et al. |
| 2002/0080478 A1 | 6/2002 | Manns |
| 2002/0097378 A1 | 7/2002 | Saito et al. |
| 2002/0156345 A1 | 10/2002 | Eppler |
| 2003/0021016 A1 | 1/2003 | Grier |
| 2003/0053025 A1 | 3/2003 | Turner et al. |
| 2003/0055410 A1 | 3/2003 | Evans et al. |
| 2003/0071893 A1 | 4/2003 | Miller et al. |
| 2003/0120266 A1 | 6/2003 | Fujieda |
| 2003/0142271 A1 | 7/2003 | Ross et al. |
| 2003/0184855 A1 | 10/2003 | Yasuda et al. |
| 2003/0185450 A1 | 10/2003 | Garakani et al. |
| 2003/0223037 A1 | 12/2003 | Chernyak |
| 2004/0017607 A1 | 1/2004 | Hauger et al. |
| 2004/0227828 A1 | 11/2004 | Loose |
| 2004/0252276 A1 | 12/2004 | Nanjo et al. |
| 2004/0263785 A1 | 12/2004 | Chernyak |
| 2004/0264765 A1 | 12/2004 | Ohba |
| 2005/0007659 A1 | 1/2005 | Steinthal et al. |
| 2005/0014996 A1 | 1/2005 | Konomura et al. |
| 2005/0018135 A1 | 1/2005 | Maeda et al. |
| 2005/0024720 A1 | 2/2005 | Cartildge |
| 2005/0025365 A1 | 2/2005 | Oosawa |
| 2005/0046930 A1 | 3/2005 | Olschewski |
| 2005/0071087 A1 | 3/2005 | Anderson |
| 2005/0107808 A1 | 5/2005 | Evans et al. |
| 2005/0111088 A1 | 5/2005 | Winterot et al. |
| 2005/0117118 A1 | 6/2005 | Miller et al. |
| 2005/0128573 A1 | 6/2005 | Merz |
| 2005/0200808 A1 | 9/2005 | Wyatt |
| 2005/0203384 A1 | 9/2005 | Sati et al. |
| 2005/0225721 A1 | 10/2005 | Harris et al. |
| 2006/0084955 A1 | 4/2006 | Hindi et al. |
| 2006/0116668 A1 | 6/2006 | Gray et al. |
| 2006/0223037 A1 | 10/2006 | Tanda |
| 2007/0081709 A1 | 4/2007 | Warmath |
| 2007/0121202 A1 | 5/2007 | Riederer |
| 2007/0121203 A1 | 5/2007 | Riederer |
| 2007/0140673 A1 | 6/2007 | Butler-Smith et al. |
| 2007/0188603 A1 | 8/2007 | Riderer |
| 2008/0018643 A1 | 1/2008 | Feikas |
| 2008/0103367 A1 | 5/2008 | Burba et al. |
| 2008/0118115 A1 | 5/2008 | Williamson |
| 2008/0247616 A1 | 10/2008 | Pescatore et al. |
| 2009/0048608 A1 | 2/2009 | Boukhny et al. |
| 2009/0125088 A1 | 5/2009 | Schleicher et al. |
| 2009/0137988 A1 | 5/2009 | Kurtz |
| 2009/0143772 A1 | 6/2009 | Kurtz |
| 2009/0171358 A1 | 7/2009 | Chang et al. |
| 2009/0236541 A1 | 9/2009 | Lomnes et al. |
| 2009/0254070 A1 | 10/2009 | Tripathi |
| 2010/0026787 A1 | 2/2010 | Yasuda et al. |
| 2010/0045933 A1 | 2/2010 | Eberl et al. |
| 2010/0094262 A1 | 4/2010 | Tripathi |
| 2010/0208199 A1 | 8/2010 | Levis et al. |
| 2010/0217278 A1 | 8/2010 | Tripathi |
| 2010/0277627 A1 | 11/2010 | Duparre et al. |
| 2011/0064286 A1 | 3/2011 | Chien et al. |
| 2011/0102549 A1 | 5/2011 | Takahashi |
| 2011/0160578 A1 | 6/2011 | Tripathi |
| 2011/0202046 A1 | 8/2011 | Angeley et al. |
| 2011/0213342 A1 | 9/2011 | Tripathi |
| 2011/0224657 A1 | 9/2011 | Stevens et al. |
| 2011/0274322 A1 | 11/2011 | Kern et al. |
| 2011/0279653 A1 | 11/2011 | Hoshino |
| 2011/0286630 A1 | 11/2011 | Harder et al. |
| 2012/0172854 A1 | 7/2012 | Raymond et al. |
| 2012/0242956 A1 | 9/2012 | Chernyak |
| 2013/0100257 A1 | 4/2013 | Sawachi |
| 2014/0114297 A1 | 4/2014 | Woodley et al. |
| 2014/0125949 A1 | 5/2014 | Shea et al. |
| 2014/0257258 A1 | 9/2014 | Kurtz |
| 2014/0303486 A1 | 10/2014 | Baumgartner et al. |
| 2014/0316388 A1 | 10/2014 | Hipsley |
| 2014/0324071 A1 | 10/2014 | Tripathi |
| 2015/0212294 A1 | 7/2015 | Imamura et al. |
| 2016/0038337 A1 | 2/2016 | Tripathi |
| 2016/0051360 A1 | 2/2016 | Tripathi |
| 2016/0246041 A1 | 8/2016 | Rappel |
| 2016/0353079 A1 | 12/2016 | Sawada |
| 2017/0143442 A1* | 5/2017 | Tesar ................ H04N 13/344 |
| 2018/0129018 A1 | 5/2018 | Cheng et al. |

FOREIGN PATENT DOCUMENTS

| | | |
|---|---|---|
| JP | 3209543 | 9/1991 |
| JP | 2009-061035 | 3/2009 |
| WO | 2000/060992 | 10/2000 |
| WO | 2000/060998 | 10/2000 |
| WO | 2003/030763 | 4/2003 |
| WO | 2005/000139 A1 | 1/2005 |
| WO | 2005042760 | 5/2005 |
| WO | 2009/158517 A3 | 12/2009 |

OTHER PUBLICATIONS

"Eye Surgery Using 3D Technology," WSFL video clip, <URL: http://southflorida.sun.sentinel.com/videobeta/watch/?watch=d69be520-0d51-4a4d-b2d2-d27f20f4bfcc&cat=empty&src=front&title=Eye%20surgery%20using%203D%20technology/.

Canrobert Oliveira, MD, The 'Keratopyramis Phenomenum' and the Canrobert 'C' Procedure, International Society of Refractive Keratoplasty 193 Pre-American Academy of Ophthalmology, Nov. 12, 1993 and Nov. 13, 1993 Chicago, Illinois USA.

DentiMag3D. Product Description [online]. StereoImaging Corporation [retrieved on Oct. 13, 2005]. retrieved from the Internet: <URL:http://www.stereoimaging.com/products/dentimag.html>.

Edward J. Holland, MD, Acrysof Toric IOL: Surgical Pearls, Cataract & Refractive Surgery Today, May 2006, pp. 71-72.

International Search Report for PCT/US2011/025746.

James P. Gills, MD, Nomogram for Limbal Relaxing Incisions with Cataract Surgery.

John Chang, M.D., Cyclotorsion during laser in situ keratomileusis, J. Cataract Refract Surg, 34:1720-1726 (2008).

Leica IC 3D. product Description [online]. Leica Microsystems [retrived on Oct. 13, 2005]. Retrieved from the Internet: <URL: http://www.oleica-microsystems.com/website/Ims.nsf?opendatabase&path=/website/products.nsf/(ALLIDs)/ECFFFC6CF17470FEC125706D002FBF06>.

Leica ICD: compact, Integrated Digital Camera for stereomiroscopes. Brochure [online]. Leica Microsystems, 2005, pp. 1-4 [retrieved on Apr. 20, 2006]. Retrieved from the Internet:<URL:http://www.leica-microsystems.com/website/Ims.nsf?opendatabase&path=WebSite/Download.nsf/(ALLIDs)/1C611440E77FF0EFC125700B003E478C>.

Louis D. "Skip" Nichamin, MD, Management of Astigmatism at the Time of Lens-Based Surgery, Tasman W. Jaeger E.A., Duane's Clinical Ophthalmology, 2006 Edition.

Posted by RCJones, Bascom Palmer Eye Institute again ranked nation's No. 1 eye hospital by U.S. News & World Report, Jul. 17, 2009, <URL: http://everitas.univmiami.net/2009/07/17/bascom-palmer-eye-institute-again-rankednations-no-1-eye-hospital-by-us-news-world-report/.

Retrieved on Aug. 27, 2008 . retrieved from the Internet, <URL:http://www.LRIcalculator.com.

Robert J. Weinstock, MD, Heads up Cataract Surgery Using the Truevision 3D System.

Ron Rajecki, The future of cataract surgery: Improved ergonomics, Ophthalmology Times, Jul. 1, 2009.

Rupert Menapace, MD, Posterior Capsulorrhexis and Optic Buttoning-In Combined with Anterior Capsule Polishing, Cataract & Refractive Surgery Today Europe, Jan./Feb. 2008, pp. 16-19.

Stephen Nellis, Venture capital in a freeze—But Santa Barbara med-tech company isn't giving up, Pacific Coast Business Times, Jan. 25, 2009.

(56) References Cited

OTHER PUBLICATIONS

Suenaga et al., Real-time in situ three-dimensional integral videography and surgical navigation using augmented reality: a pilot study. International Journal of Oral Science 5: 98-102 (2013).

Technology to perform LRIs using lasers [online]. LensAR Inc. [retrieved on Oct. 20, 2009]. retrieved from the Internet, <URL:http://www.sujanani.com/lasik/lasik_surgery/?p=101859.

Technology to perform LRIs using lasers [online]. LenSx Lasers, Inc. [retrieved on Oct. 20, 2009]. retrieved from the Internet, <URL:http://www.ventureinvestors.com/archives/1516.

Technology to perform LRIs using lasers [online]. OptiMedica [retrieved on Oct. 20, 2009]. retrieved from the Internet, <URL:http://www.optimedica.com/.

The World's Only: Interactive Leica 3D System for Microscopy. Press Release [online]. Leica Microsystems, Jun. 24, 2005, pp. 1-2 [retrieved on Oct. 13, 2005]. Retrieved from the Internet: <URL:http://www.leica-microsystems.com/website/lms.nsf?opendatabase&path=/website/products.nsf/(ALLIDs)/ECFFFcCF17470FEC125706D002FBF06> (See Press Releases).

TrueVision Systems Inc., 510K Application Summary for TrueVision 3D Visualization and Guidance System, Dec. 22, 2010.

U.S. Office Action mailed by Office dated Mar. 29, 2016 for U.S. Appl. No. 13/024,948, filed Feb. 10, 2011.

International Search Report for PCT/US2013/057686 dated Mar. 6, 2014.

Supplementary European Search Report for European Patent Application 13834045 dated Jul. 14, 2017.

Gering et al., An integrated visualization system for surgical planning and guidance using image fusion and interventional imaging. Medical Image Computing and Computer Assisted Intervention-Miccai '99. Second International Conference, Cambridge, UK, Sep. 19-22, 1999, pp. 809-819.

U.S. Office Action mailed by Office dated May 12, 2016 for U.S. Appl. No. 14/424,985, filed Feb. 27, 2015.

International search report on international application PCT/US2018/028360 dated Nov. 7, 2019.

\* cited by examiner

STEREOSCOPIC CAMERA WITH FLUORESCENCE VISUALIZATION

PRIORITY CLAIM

The present application is a continuation-in-part of U.S. patent application Ser. No. 16/422,204 filed on May 24, 2019, which is a continuation application of U.S. patent application Ser. No. 15/814,127 filed on Nov. 15, 2017, now U.S. Pat. No. 10,299,880, which is a non-provisional of and claims priority to and the benefit of U.S. Provisional Patent Application No. 62/489,289 filed on Apr. 24, 2017 and U.S. Provisional Patent Application No. 62/489,876 filed on Apr. 25, 2017, the entirety of which are incorporated herein by reference.

BACKGROUND

Surgery is art. Accomplished artists create works of art that far exceed the capabilities of a normal person. Artists use a brush to turn canisters of paint into vivid images that provoke strong and unique emotions from viewers. Artists take ordinary words written on paper and turn them into dramatic and awe-inspiring performances. Artists grasp instruments causing them to emit beautiful music. Similarly, surgeons take seemingly ordinary scalpels, tweezers, and probes and produce life-altering biological miracles.

Like artists, surgeons have their own methods and preferences. Aspiring artists are taught the fundamentals of their craft. Beginners often follow prescribed methods. As they gain experience, confidence, and knowledge, they develop their own unique artistry reflective of themselves and their personal environment. Similarly, medical students are taught the fundamentals of surgical procedures. They are rigorously tested on these methods. As the students progress through residency and professional practice, they develop derivations of the fundamentals (still within medical standards) based on how they believe the surgery should best be completed. For instance, consider the same medical procedure performed by different renowned surgeons. The order of events, pacing, placement of staff, placement of tools, and use of imaging equipment varies between each of the surgeons based on their preferences. Even incision sizes and shapes can be unique to the surgeon.

The artistic-like uniqueness and accomplishment of surgeons make them weary of surgical tools that change or alter their methods. The tool should be an extension of the surgeon, operating simultaneously and/or in harmonious synchronization. Surgical tools that dictate the flow of a procedure or change the rhythm of a surgeon are often discarded or modified to conform.

In an example, consider microsurgery visualization where certain surgical procedures involve patient structures that are too small for a human to visualize easily with the naked eye. For these microsurgery procedures, magnification is required to adequately view the micro-structures. Surgeons generally want visualization tools that are natural extensions of their eyes. Indeed, early efforts at microsurgery visualization comprised attaching magnifying lens to head-mounted optical eyepieces (called surgical loupes). The first pair was developed in 1876. Vastly improved versions of surgical loupes (some including optical zooms and integrated light sources) are still being used by surgeons today. FIG. 1 shows a diagram of a pair of surgical loupes 100 with a light source 102 and magnification lenses 104. The 150-year staying power of surgical loupes can be attributed to the fact that they are literally an extension of a surgeon's eyes.

Despite their longevity, surgical loupes are not perfect. Loupes with magnifying lenses and light sources, such as the loupes 100 of FIG. 1, have much greater weight. Placing even a minor amount of weight on the front of a surgeon's face can increase discomfort and fatigue, especially during prolonged surgeries. The surgical loupes 100 also include a cable 106 that is connected to a remote power supply. The cable effectively acts as a chain, thereby limiting the mobility of the surgeon during their surgical performance.

Another microsurgery visualization tool is the surgical microscope, also referred to as the operating microscope. Widespread commercial development of surgical microscopes began in the 1950s with the intention of replacing surgical loupes. Surgical microscopes include optical paths, lenses, and focusing elements that provide greater magnification compared to surgical loupes. The large array of optical elements (and resulting weight) meant that surgical microscopes had to be detached from the surgeon. While this detachment gave the surgeon more room to maneuver, the bulkiness of the surgical microscope caused it to consume considerable operating space above a patient, thereby reducing the size of the surgical stage.

FIG. 2 shows a diagram of a prior art surgical microscope 200. As one can imagine, the size and presence of the surgical microscope in the operating area made it prone to bumping. To provide stability and rigidity at the scope head 201, the microscope is connected to relatively large boom arms 202 and 204 or other similar support structure. The large boom arms 202 and 204 consume additional surgical space and reduce the maneuverability of the surgeon and staff. In total, the surgical microscope 200 shown in FIG. 2 could weigh as much as 350 kilograms ("kg").

To view a target surgical site using the surgical microscope 200, a surgeon looks directly though oculars 206. To reduce stress on a surgeon's back, the oculars 206 are generally positioned along a surgeon's natural line of sight using the arm 202 to adjust height. However, surgeons do not perform by only looking at a target surgical site. The oculars 206 have to be positioned such that the surgeon is within arm's length of a working distance to the patient. Such precise positioning is critical to ensure the surgical microscope 200 becomes an extension rather than a hindrance to the surgeon, especially when being used for extended periods of time.

Like any complex instrument, it takes surgeons tens to hundreds of hours to feel comfortable using a surgical microscope. As shown in FIG. 2, the design of the surgical microscope 200 requires a substantially 90° angle optical path from the surgeon to the target surgical site. For instance, a perfectly vertical optical path is required from the target surgical site to the scope head 201. This means that the scope head 201 has to be positioned directly above the patient for every microsurgical procedure. In addition, the surgeon has to look almost horizontally (or some slight angle downward) into the oculars 206. A surgeon's natural inclination is to direct his vision to his hands at the surgical site. Some surgeons even want to move their heads closer to the surgical site to have more precise control of their hand movements. Unfortunately, the surgical microscopes 200 do not give surgeons this flexibility. Instead, surgical microscopes 200 ruthlessly dictate that the surgeon is to place their eyes on the oculars 206 and hold their head at arm's length during their surgical performance, all while consuming valuable surgical space above the patient. A surgeon cannot even simply look down at a patient because the scope head 201 blocks the surgeon's view.

To make matters worse, some surgical microscopes 200 include a second pair of oculars 208 for co-performers (e.g., assistant surgeons, nurses, or other clinical staff). The second pair of oculars 208 is usually positioned at a right angle from the first oculars 206. The closeness between the oculars 206 and 208 dictates that the assistant must stand (or sit) in close proximity to the surgeon, further restricting movement. This can be annoying to some surgeons who like to perform with some space. Despite their magnification benefits surgical microscopes 200 are not natural extensions of a surgeon. Instead, they are overbearing directors in the surgical room.

SUMMARY

The present disclosure is directed to stereoscopic visualization camera and platform that is configured to effectively operate as an extension of a surgeon's eyes while giving the surgeon the freedom to conduct a microsurgery procedure generally without restrictions. The example stereoscopic visualization camera disclosed herein comprises a digital stereoscopic visualization platform with full-range, operator-independent orientation for microsurgical applications. The example stereoscopic visualization camera and platform decouples the micro-surgery visualization system from a surgeon's head and eyes to provide for a wide variety of multi-axis orientations of the surgical visualization system relative to the surgeon and to the target surgical field. As a result, the surgeon is provided with an enhanced magnified view of the surgical site without having to work around a bulky microscope positioned over the patient and in front of the surgeon's face. The example stereoscopic visualization camera accordingly enables a surgeon to complete life-altering microsurgeries comfortably in whatever position suits the surgeon. Moreover, the surgical visualization camera of the present disclosure can be positioned along and about any number of orientations relative to the surgical field that best suit the needs of the surgeon or patient, rather than the physical and mechanical limitations of the visualization apparatus.

The example stereoscopic visualization camera and corresponding platform has many distinct advantages over known monoscopic and stereoscopic cameras. Current monoscopic and stereoscopic cameras are connected to an optical path of a surgical microscope. While being connected to the optical path, the cameras have no control over focus, zooming, and/or setting a working distance. Instead, these controls are located at the scope head of the surgical microscope. In addition, optical elements in a surgical microscope provide generally acceptable image quality for oculars. However, defects in the image quality or slightly misaligned right and left views become more apparent when acquired by a camera and displayed on a video monitor.

The example stereoscopic visualization camera overcomes the above-mentioned issues of known monoscopic and stereoscopic cameras by being configured as a self-contained device that does not rely on external microscope optical elements. The example stereoscopic visualization camera instead internalizes the optical elements that are common on a surgical microscope. The optical elements may be provided on tracks and/or flexures within the camera to allow for manual and/or automatic adjustment. Accordingly, adjustment of the optical elements can be provided through camera controls and/or user input devices connected to the camera, which enables adjustment to be made specifically for the camera. In addition, the optical elements of the stereoscopic visualization camera may be automatically and/or manually adjusted to align focus points of left and right images and reduce visual defects and/or spurious parallax. The end result is a relatively lightweight maneuverable stereoscopic visualization camera that provides a virtually flawless three-dimensional stereoscopic display that allows surgeons to practice their art without visual encumbrances.

In an example embodiment, a stereoscopic imaging apparatus is configured to reduce spurious parallax between first and second images streams acquired or recorded in parallel of a target site. The apparatus includes first optical elements positioned along a first optical path. The first optical elements comprise a first plurality of lenses including a first zoom lens configured to be moveable along the first optical path in a z-direction and a first image sensor to acquire the first image stream of the target site from light in the first optical path. The apparatus also includes second optical elements positioned along a second optical path parallel to the first optical path. The second optical elements comprise a second plurality of lenses including a second zoom lens configured to be moveable along the second optical path in a z-direction and a second image sensor to acquire the second image stream of the target site from light in the second optical path. The apparatus further includes a processor configured to locate a position of a first zoom repeat point ("ZRP") by causing the first zoom lens to move along the z-direction during a recording of the first image stream, locating a first portion of area that does not move in an x-direction or a y-direction within the images of the first image stream, and determining a first distance between an origin point within at least one of the images of the first image stream and the first portion of the area as the position of the first ZRP. The example processor is also configured to determine a first pixel set of a first pixel grid of the first image sensor using the first distance such that the first ZRP is located at a center of the first pixel set and determine a second pixel set of a second pixel grid of the second image sensor that includes an image that is aligned with an image from the first pixel set of the first image sensor. The example processor is further configured to locate a position of a second ZRP by causing the second lens to move along the z-direction during a recording of the second image stream, locating a second portion of area that does not move in the x-direction or the y-direction within the images of the second image stream, and determining a second distance between a center of the second pixel set and the second portion of the area as the position of the second ZRP. Moreover, the example processor is configured to adjust one of the second plurality of lenses or the second image sensor in at least one of the x-direction, the y-direction, and a tilt-direction to cause the second ZRP to be aligned with the center of the second pixel set based on the determined second distance.

The example processor reduces or eliminates spurious parallax by determining a first pixel set of a first pixel grid of the first image sensor using the first distance such that the first ZRP is located at a center of the first pixel set. In addition, the processor determines a second pixel set of a second pixel grid of the second image sensor that includes an image that is aligned with an image from the first pixel set of the first image sensor. Further, the example processor adjusts one of the second plurality of lenses in at least one of the x-direction and the y-direction and a tilt direction to cause the second ZRP to be aligned with a center of the second pixel set based on the determined second distance. In an alternative embodiment, the example processor may digitally change an optical property of the one of the second plurality of lenses to have the same effect as moving the one of the second plurality of lenses. The processor stores the location of the first and second pixel sets in relation to a magnification level of the first and second zoom lenses as a calibration point. The processor may use the calibration point and select the stored locations of the pixel sets when the stereoscopic imaging apparatus subsequently returns to the same or a similar magnification level.

In another embodiment, a stereoscopic imaging apparatus is configured to provide for fluorescence visualization. In this embodiment, the stereoscopic imaging apparatus includes a main objective assembly configured to change a working distance along an optical axis to a target surgical site, and left and right lens sets defining respective parallel left and right optical paths along the optical axis and configured to form the respective optical paths from light that is received from the main objective assembly of the target surgical site. The stereoscopic imaging apparatus also includes a light filter assembly having left and right filter magazines positioned respectively along the left and right optical paths and configured to selectively enable certain wavelengths of the light to pass through. Each of the left and right filter magazines includes an infrared cut filter, a near-ultraviolet cut filter, and a near-infrared bandpass filter. The stereoscopic imaging apparatus further includes left and right image sensors configured to receive the filtered light and convert the filtered light into image data that is indicative of the received filtered light, and a processor communicatively coupled to the left and right image sensors and configured to convert the image data into stereoscopic video signals or video data for display on a display monitor. Additionally, the stereoscopic imaging apparatus includes a deflecting element located between the main objective assembly and the left and right lens sets. The deflecting element is configured to reflect the light received from the main objective assembly to the left and right lens sets. Moreover, the stereoscopic imaging apparatus includes a visible light source positioned to transmit visible light through the main objective assembly to the target surgical site, a near-infrared light source positioned to transmit near-infrared light through the main objective assembly to the target surgical site, and an excitation filter positioned in front of the near-infrared light source configured to enable light at indocyanine green ("ICG") fluorescence absorption wavelengths to pass through. Further, the stereoscopic imaging apparatus includes a controller configured to provide a visible light mode by causing the visible light reflected from the target surgical site to be provided to the left and right image sensors by activating the visible light source and selecting at least one of the infrared cut filter or the near-ultraviolet cut filter to be placed in the respective optical path, provide an ICG fluorescence mode by causing ICG fluorescence emission light from the target surgical site to be provided to the left and right image sensors by activating at least one of the visible light source or the near-infrared light source and selecting the near-infrared bandpass filter to be placed in the respective optical path, and switch between the visible light mode and the ICG mode to enable the processor to provide stereoscopic video signals or video data with at least some image data corresponding to the ICG fluorescence emission light to be superimposed on image data corresponding to the visible light.

The advantages discussed herein may be found in one, or some, and perhaps not all of the embodiments disclosed herein. Additional features and advantages are described herein, and will be apparent from the following Detailed Description and the figures.

DETAILED DESCRIPTION

Figure 1:
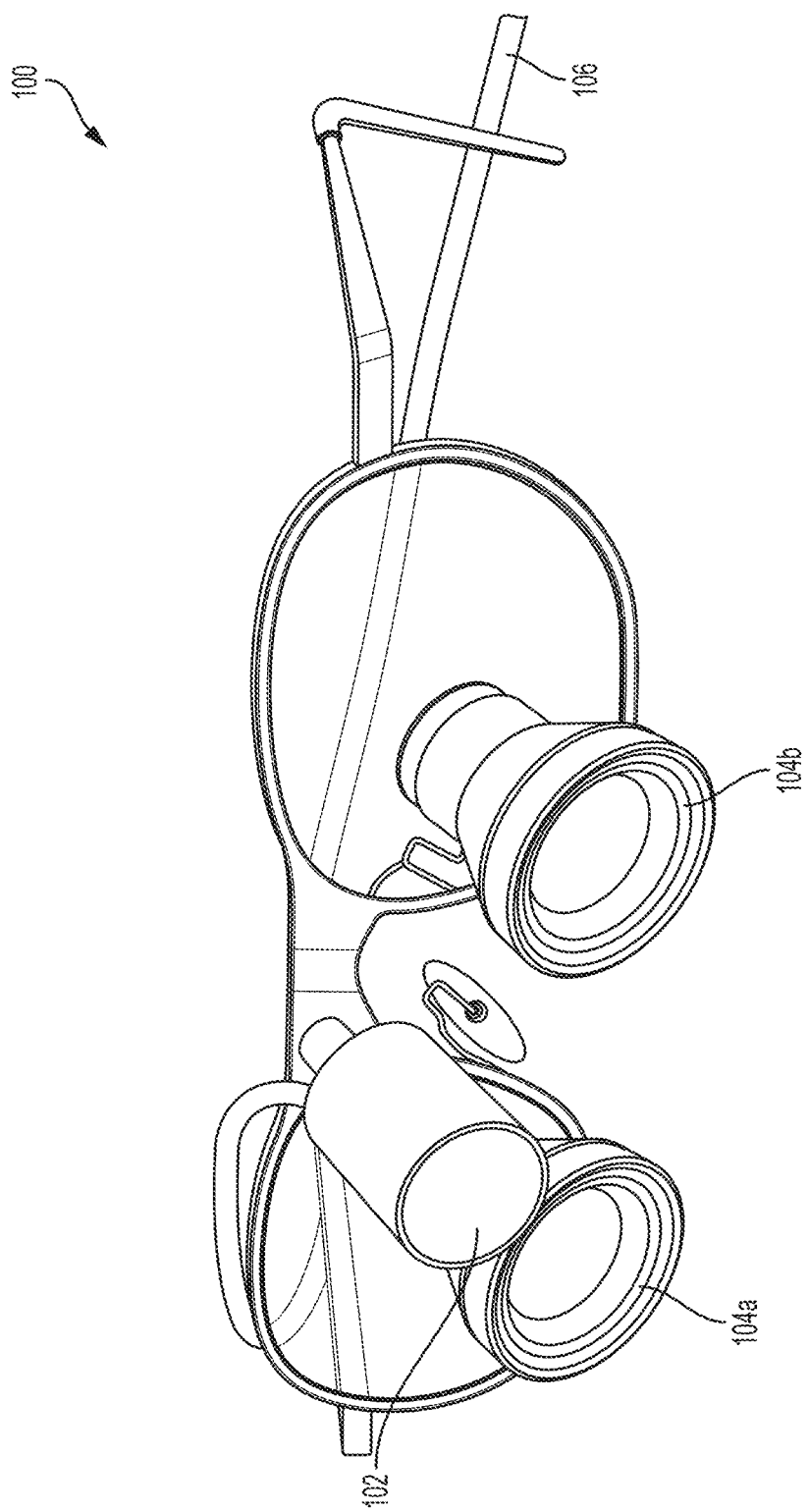
FIG. 1 shows a diagram of a pair of prior art surgical loupes.

The present disclosure relates in general to a stereoscopic visualization camera and platform. The stereoscopic visualization camera may be referred to as a digital stereoscopic microscope ("DSM"). The example camera and platform are configured to integrate microscope optical elements and video sensors into a self-contained head unit that is significantly smaller, lighter, and more maneuverable than prior art microscopes (such as the surgical loupes 100 of FIG. 1 and the surgical microscope 200 of FIG. 2). The example camera is configured to transmit a stereoscopic video signal to one or more television monitors, projectors, holographic devices, smartglasses, virtual reality devices, or other visual display devices within a surgical environment.

The monitors or other visual display devices may be positioned within the surgical environment to be easily within a surgeon's line of sight while performing surgery on a patient. This flexibility enables the surgeon to place display monitors based on personal preferences or habits. In addition, the flexibility and slim profile of the stereoscopic visualization camera disclosed herein reduces area consumed over a patient. Altogether, the stereoscopic visualization camera and monitors (e.g., the stereoscopic visualization platform) enables a surgeon and surgical team to perform complex microsurgical surgical procedures on a patient without being dictated or restricted in movement compared to the surgical microscope 200 discussed above. The example stereoscopic visualization platform accordingly operates as an extension of the surgeon's eyes, enabling the surgeon to perform masterpiece microsurgeries without dealing with the stress, restrictions, and limitations induced by previous known visualization systems.

The disclosure herein generally refers to microsurgery. The example stereoscopic visualization camera may be used in virtually any microsurgical procedure including, for example, cranial surgery, brain surgery, neurosurgery, spinal surgery, ophthalmologic surgery, corneal transplants, orthopedic surgery, ear, nose and throat surgery, dental surgery, plastics and reconstructive surgery, or general surgery.

The disclosure also refers herein to target site, scene, or field-of-view. As used herein, target site or field-of-view includes an object (or portion of an object) that is being recorded or otherwise imaged by the example stereoscopic visualization camera. Generally the target site, scene, or field-of-view is a working distance away from a main objective assembly of the example stereoscopic visualization camera and is aligned with the example stereoscopic visualization camera. The target site may include a patient's biological tissue, bone, muscle, skin or combinations thereof. In these instances, the target site may be three dimensional by having a depth component corresponding to a progression of a patient's anatomy. The target site may also include one or more templates used for calibration or verification of the example stereoscopic visualization camera. The templates may be two-dimensional, such as a graphic design on paper (or plastic sheet) or three dimensional, such as to approximate a patient's anatomy in a certain region.

Reference is also made throughout to an x-direction, a y-direction, a z-direction, and a tilt-direction. The z-direction is along an axis from the example stereoscopic visualization camera to the target site and generally refers to depth. The x-direction and y-direction are in a plane incident to the z-direction and comprise a plane of the target site. The x-direction is along an axis that is 90° from an axis of the y-direction. Movement along the x-direction and/or the y-direction refer to in-plane movement and may refer to movement of the example stereoscopic visualization camera, movement of optical elements within the example stereoscopic visualization camera, and/or movement of the target site.

The tilt-direction corresponds movement along Euler angles (e.g., a yaw axis, a pitch axis, and a roll axis) with respect to the x-direction, the y-direction, and/or the z-direction. For example, a perfectly aligned lens has substantially a 0° tilt with respect to the x-direction, the y-direction, and/or the z-direction. In other words, a face of the lens is 90° or perpendicular to light along the z-direction. In addition, edges of the lens (if the lens has a rectangular shape) are parallel along the x-direction and the y-direction. Lens and/or optical image sensors can be titled through yaw movement, pitch movement, and/or roll movement. For example, a lens and/or optical image sensor may be titled along a pitch axis, with respect to the z-direction, to face upwards or downwards. Light along the z-direction contacts a face of a lens (that is pitched upwards or downwards) at non-perpendicular angle. Tilting of a lens and/or optical image sensor along a yaw axis, pitch axis, or roll axis enables, for example, a focal point or ZRP to be adjusted.

I. Example Stereoscopic Visualization Camera

Figure 3:
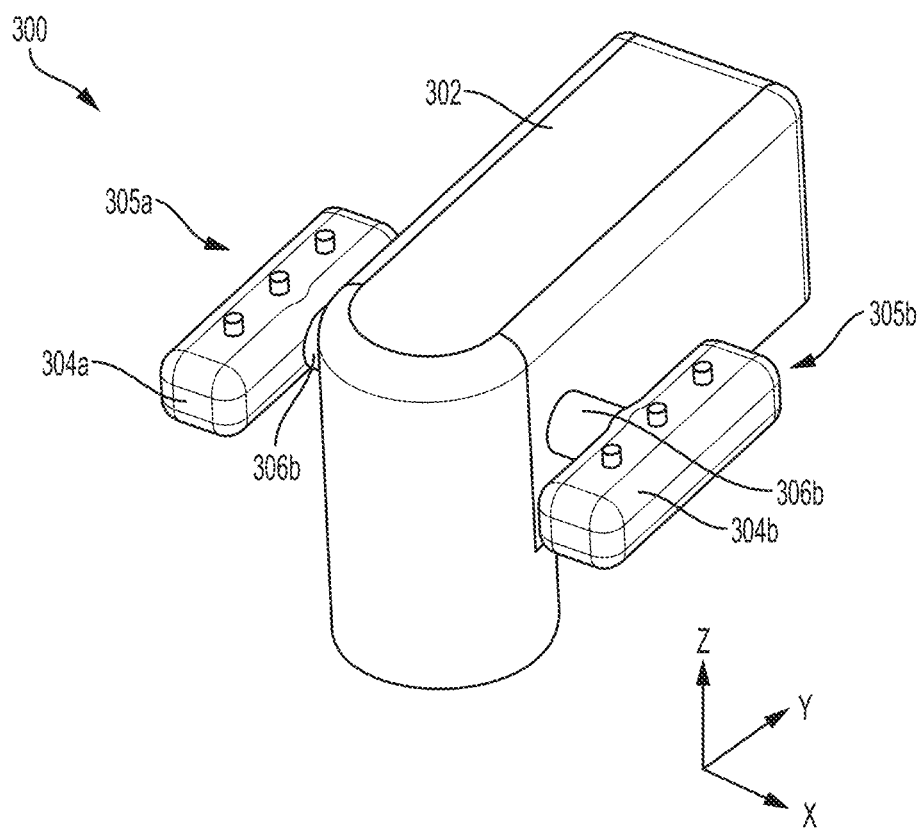
FIGS. 3 and 4 show diagrams of perspective views of a stereoscopic visualization camera, according to an example embodiment of the present disclosure.
Figure 4:
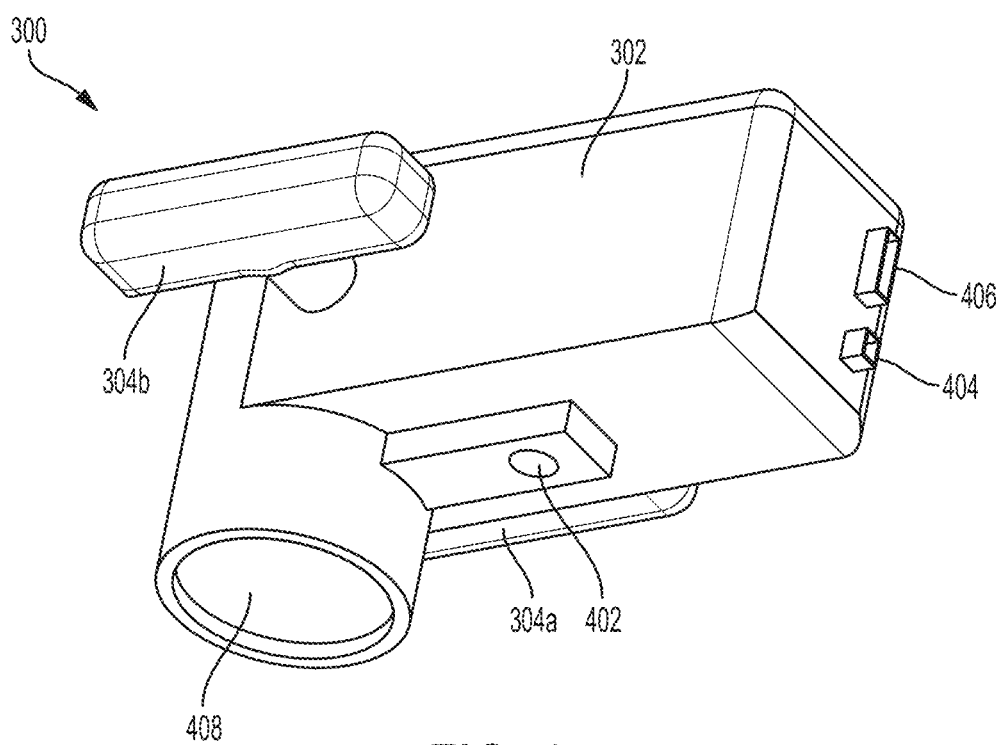

FIGS. 3 and 4 show diagrams of perspective views of a stereoscopic visualization camera 300, according to an example embodiment of the present disclosure. The example camera 300 includes a housing 302 configured to enclose optical elements, lens motors (e.g., actuators), and signal processing circuitry. The camera 300 has a width (along an x-axis) between 15 to 28 centimeters (cm), preferably around 22 cm. In addition, the camera 300 has a length (along a y-axis) between 15 to 32 cm, preferably around 25 cm. Further, the camera 300 has a height (along a z-axis) between 10 to 20 cm, preferably around 15 cm. The weight of the camera 300 is between 3 to 7 kg, preferably around 3.5 kg.

The camera 300 also includes control arms 304*a* and 304*b* (e.g., operating handles), which are configured to control magnification level, focus, and other microscope features. The control arms 304*a* and 304*b* may include respective controls 305*a* and 305*b* for activating or selecting certain features. For example, the control arms 304*a* and 304*b* may include controls 305*a* and 305*b* for selecting a fluorescence mode, adjusting an amount/type of light projected onto a target site, and controlling a display output signal (e.g., selection between 1080p or 4K and/or stereoscopic). In addition, the controls 305a and/or 305b may be used to initiate and/or perform a calibration procedure and/or move a robotic arm connected to the stereoscopic visualization camera 300. In some instances, the controls 305a and 305b may include the same buttons and/or features. In other instances the controls 305a and 305b may include different features. Further, the control arms 304a and 304b may also be configured as grips to enable an operator to position the stereoscopic visualization camera 300.

Each control arm 304 is connected to the housing 302 via a rotatable post 306, as shown in FIG. 3. This connection enables the control arms 304 to be rotated with respect to the housing 302. This rotation provides flexibility to a surgeon to arrange the control arms 304 as desired, further enhancing the adaptability of the stereoscopic visualization camera 300 to be in synchronization with a surgical performance.

While the example camera 300 shown in FIGS. 3 and 4 includes two control arms 304a and 304b, it should be appreciated that the camera 300 may only include one control arm or zero control arms. In instances where the stereoscopic visualization camera 300 does not include a control arm, controls may be integrated with the housing 302 and/or provided via a remote control.

FIG. 4 shows a bottom-up perspective view of a rear-side of the stereoscopic visualization camera 300, according to an example embodiment of the present disclosure. The stereoscopic visualization camera 300 includes a mounting bracket 402 configured to connect to a support. As described in more detail in FIGS. 5 and 6, the support may include an arm with one or more joints to provide significant maneuverability. The arm may be connected to a moveable cart or secured to a wall or ceiling.

The stereoscopic visualization camera 300 also includes a power port 404 configured to receive a power adapter. Power may be received from an AC outlet and/or a battery on a cart. In some instances, the stereoscopic visualization camera 300 may include an internal battery to facilitate operation without cords. In these instances, the power port 404 may be used to charge the battery. In alternative embodiments, the power port 404 may be integrated with the mounting bracket 402 such that the stereoscopic visualization camera 300 receives power via wires (or other conductive routing materials) within the support.

FIG. 4 also shows that the stereoscopic visualization camera 300 may include a data port 406. The example data port 406 may include any type of port including, for example, an Ethernet interface, a high-definition multimedia interface ("HDMI") interface, a universal serial bus ("USB") interface, a Serial Digital Interface ("SDI"), a digital optical interface, an RS-232 serial communication interface etc. The data port 406 is configured to provide a communicative connection between the stereoscopic visualization camera 300 and cords routed to one or more computing devices, servers, recording devices, and/or display devices. The communicative connection may transmit stereoscopic video signals or two-dimensional video signals for further processing, storage, and/or display. The data port 406 may also enable control signals to be sent to the stereoscopic visualization camera 300. For instance, an operator at a connected computer (e.g., a laptop computer, desktop computer, and/or tablet computer) may transmit control signals to the stereoscopic visualization camera 300 to direct operation, perform calibration, or change an output display setting.

In some embodiments, the data port 406 may be replaced (and/or supplemented) with a wireless interface. For example, the stereoscopic visualization camera 300 may transmit stereoscopic display signals via Wi-Fi to one or more display devices. A use of a wireless interface, combined with an internal battery, enables the stereoscopic visualization camera 300 to be wire-free, thereby further improving maneuverability within a surgical environment.

The stereoscopic visualization camera 300 shown in FIG. 4 also includes a front working distance main objective lens 408 of a main objective assembly. The example lens 408 is the start of the optical path within the stereoscopic visualization camera 300. Light from a light source internal to the stereoscopic visualization camera 300 is transmitted through the lens 408 to a target site. Additionally, light reflected from the target site is received in the lens 408 and passed to downstream optical elements.

II. Exemplary Maneuverability of the Stereoscopic Visualization Camera

Figure 5:
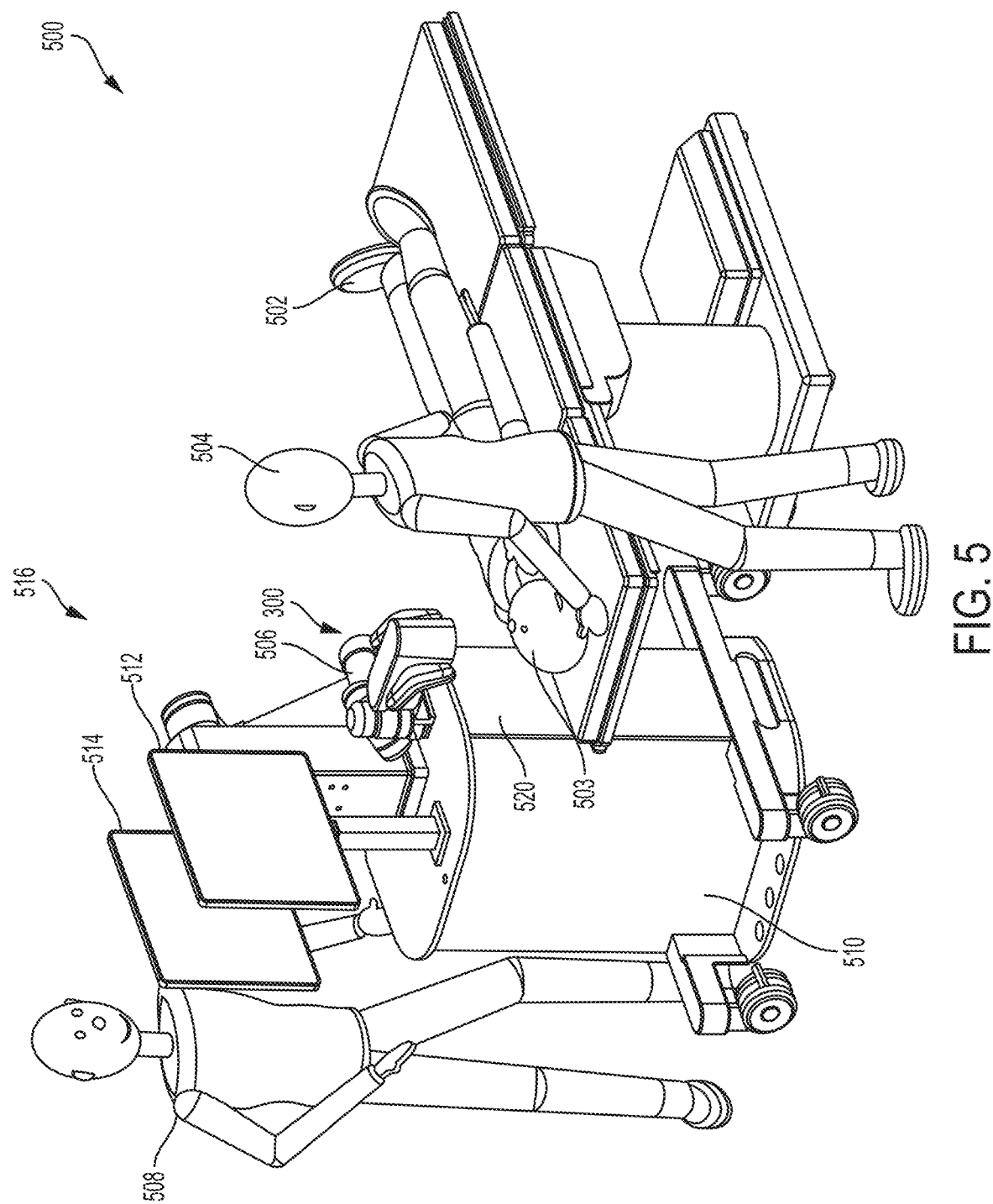
FIGS. 5 and 6 show diagrams of a microsurgical environment including the stereoscopic visualization camera of FIGS. 3 and 4, according to example embodiments of the present disclosure.
Figure 6:
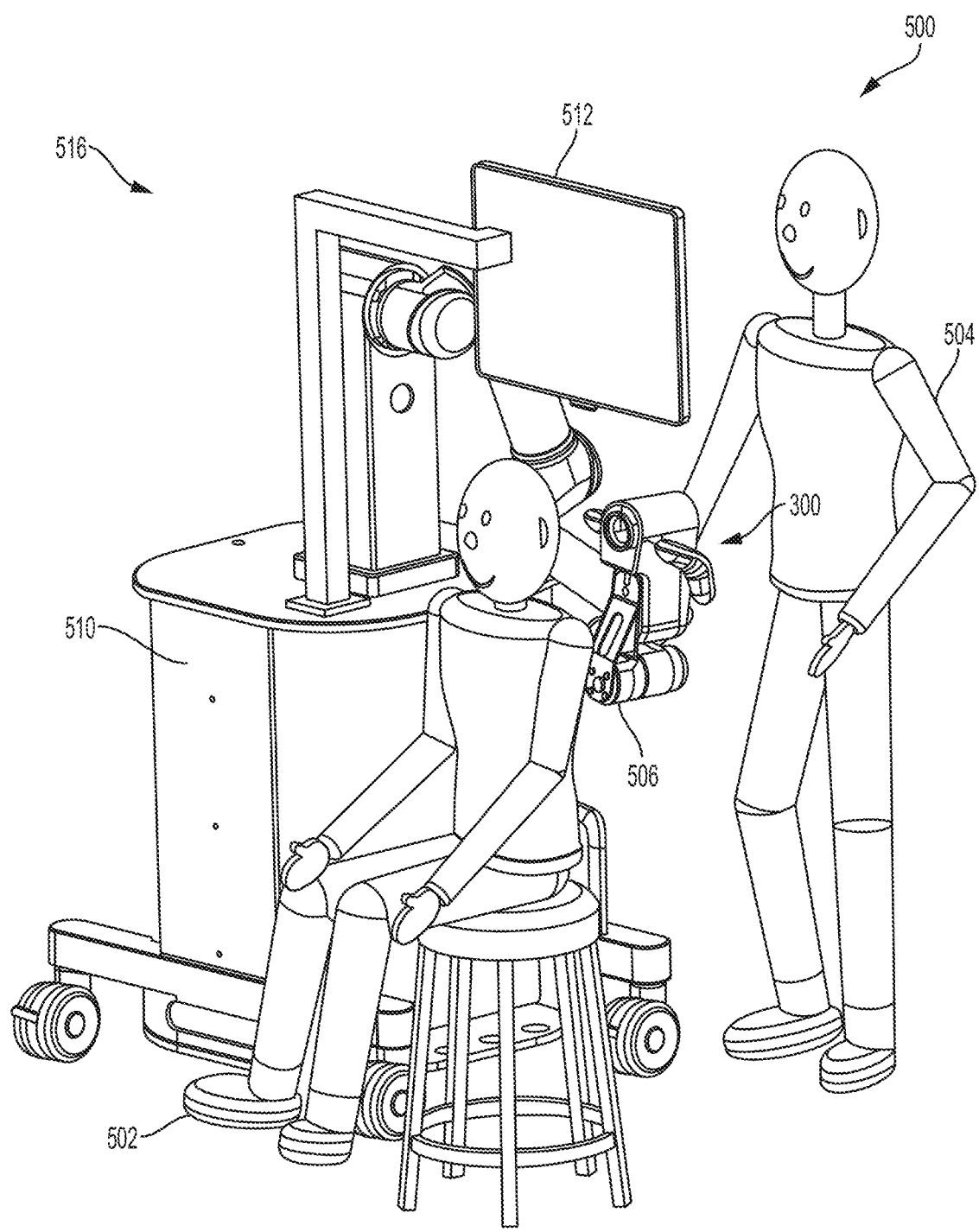

FIGS. 5 and 6 show diagrams of the stereoscopic visualization camera 300 used within a microsurgical environment 500, according to example embodiments of the present disclosure. As illustrated, the small footprint and maneuverability of the stereoscopic visualization camera 300 (especially when used in conjunction with a multiple-degree of freedom arm) enables flexible positioning with respect to a patient 502. A portion of the patient 502 in view of the stereoscopic visualization camera 300 includes a target site 503. A surgeon 504 can position the stereoscopic visualization camera 300 in virtually any orientation while leaving more than sufficient surgical space above the patient 502 (lying in the supine position). The stereoscopic visualization camera 300 accordingly is minimally intrusive (or not intrusive) to enable the surgeon 504 to perform a life-altering microsurgical procedure without distraction or hindrance.

In FIG. 5, the stereoscopic visualization camera 300 is connected to a mechanical arm 506 via mounting bracket 402. The arm 506 may include one or more rotational or extendable joints with electromechanical brakes to facilitate easy repositioning of the stereoscopic visualization camera 300. To move the stereoscopic visualization camera 300, the surgeon 504, or the assistant 508, actuates brake releases on one or more joints of the arm 506. After the stereoscopic visualization camera 300 is moved into a desired position, the brakes may be engaged to lock the joints of the arm 506 in place.

A significant feature of the stereoscopic visualization camera 300 is that it does not include oculars. This means that the stereoscopic visualization camera 300 does not have to be aligned with the eyes of the surgeon 504. This freedom enables the stereoscopic visualization camera 300 to be positioned and orientated in desirable positions that were not practical or possible with prior known surgical microscopes. In other words, the surgeon 504 can perform microsurgery with the most optimal view for conducting the procedure rather than being restricted to merely adequate view dictated by oculars of a surgical microscope.

Returning to FIG. 5, the stereoscopic visualization camera 300, via the mechanical arm 506, is connected to a cart 510 with display monitors 512 and 514 (collectively a stereoscopic visualization platform 516). In the illustrated configuration, the stereoscopic visualization platform 516 is self-contained and may be moved to any desired location in the microsurgical environment 500 including between surgical rooms. The integrated platform 516 enables the stereoscopic visualization camera 300 to be moved and used on-demand without time needed to configure the system by connecting the display monitors 512 and 514.

The display monitors 512 and 514 may include any type of display including a high-definition television, an ultra-high definition television, smart-eyewear, projectors, one or more computer screens, laptop computers, tablet computers, and/or smartphones. The display monitors 512 and 514 may be connected to mechanical arms to enable flexible positioning similar to the stereoscopic visualization camera 300. In some instances, the display monitors 512 and 514 may include a touchscreen to enable an operator to send commands to the stereoscopic visualization camera 300 and/or adjust a setting of a display.

In some embodiments, the cart 516 may include a computer 520. In these embodiments, the computer 520 may control a robotic mechanical arm connected to the stereoscopic visualization camera 300. Additionally or alternatively, the computer 520 may process video (or stereoscopic video) signals (e.g., an image or frame stream) from the stereoscopic visualization camera 300 for display on the display monitors 512 and 514. For example, the computer 520 may combine or interleave left and right video signals from the stereoscopic visualization camera 300 to create a stereoscopic signal for displaying a stereoscopic image of a target site. The computer 520 may also be used to store video and/or stereoscopic video signals into a video file (stored to a memory) so the surgical performance can be documented and played back. Further, the computer 520 may also send control signals to the stereoscopic visualization camera 300 to select settings and/or perform calibration.

In some embodiments, the microsurgical environment 500 of FIG. 5 includes an ophthalmic surgery procedure. In this embodiment, the mechanical arm 506 may be programmed to perform an orbiting sweep of a patient's eye. Such a sweep enables the surgeon to examine a peripheral retina during vitreo-retinal procedures. In contrast, with conventional optical microscopes, the only way a surgeon can view the peripheral retina is to push the side of the eye into the field of view using a technique known as scleral depression.

FIG. 6 shows a diagram of the microsurgical environment 500 with the patient 502 in a sitting position for a posterior-approach skull base neurosurgery. In the illustrated embodiment, the stereoscopic visualization camera 300 is placed into a horizontal position to face the back of the head of the patient 502. The mechanical arm 506 includes joints that enable the stereoscopic visualization camera 300 to be positioned as shown. In addition, the cart 510 includes the monitor 512, which may be aligned with the surgeon's natural view direction.

The absence of oculars enables the stereoscopic visualization camera 300 to be positioned horizontally and lower than the eye-level view of the surgeon 504. Further, the relatively low weight and flexibility enables the stereoscopic visualization camera 300 to be positioned in ways unimaginable for other known surgical microscopes. The stereoscopic visualization camera 300 thereby provides a microsurgical view for any desired position and/or orientation of the patient 502 and/or the surgeon 504.

While FIGS. 5 and 6 show two example embodiments for positioning the stereoscopic visualization camera 300, it should be appreciated that the stereoscopic visualization camera 300 may be positioned in any number of positions depending on the number of degrees of freedom of the mechanical arm 506. It is entirely possible in some embodiments to position the stereoscopic visualization camera 300 to face upwards (e.g., upside down).

III. Comparison of the Example Stereoscopic Visualization Platform to Known Surgical Microscopes In comparing the stereoscopic visualization camera 300 of FIGS. 3 to 6 to the surgical microscope 200 of FIG. 2, the differences are readily apparent. The inclusion of oculars 206 with the surgical microscope requires that the surgeon constantly orient his/her eyes to eyepieces, which are in a fixed location relative to the scope head 201 and patient. Further, the bulkiness and weight of the surgical microscope restricts it to being positioned only in a generally vertical orientation with respect to a patient. In contrast, the example stereoscopic visualization camera 300 does not include oculars and may be positioned in any orientation or position with respect to a patient, thereby freeing the surgeon to move during surgery.

To enable other clinician staff to view a microsurgical target site, the surgical microscope 200 requires the addition of second oculars 208. Generally, most known surgical microscopes 200 do not allow adding third oculars. In contrast, the example stereoscopic visualization camera 300 may be communicatively coupled to an unlimited number of display monitors. While FIGS. 5 and 6 above showed display monitors 512 and 514 connected to cart 510, a surgical room may be surrounded in display monitors that all show the microsurgical view recorded by the stereoscopic visualization camera 300. Thus, instead of limiting a view to one or two people (or requiring sharing an ocular), an entire surgical team can view a magnified view of a target surgical site. Moreover, people in other rooms, such as training and observation rooms, can be presented with the same magnified view displayed to the surgeon.

Compared to the stereoscopic visualization camera 300, the two-ocular surgical microscope 200 is more prone to being bumped or inadvertently moved. Since surgeons place their heads on oculars 206 and 208 during surgery to look through eyepieces, the scope head 201 receives constant force and periodic bumps. Adding the second oculars 208 doubles the force from a second angle. Altogether, the constant force and periodic bumping by the surgeons may cause the scope head 201 to move, thereby requiring the scope head 201 to be repositioned. This repositioning delays the surgical procedure and annoys the surgeon.

The example stereoscopic visualization camera 300 does not include oculars and is not intended to receive contact from a surgeon once it is locked into place. This corresponds to a significantly lower chance of the stereoscopic visualization camera 300 being accidently moved or bumped during the surgeon's performance.

To facilitate the second oculars 208, the surgical microscope 200 has to be outfitted with a beamsplitter 210, which may include glass lenses and mirrors housed in precision metallic tubes. The use of a beamsplitter 210 reduces light received at the first oculars because some of the light is reflected to the second oculars 208. Further, addition of the second oculars 208 and the beamsplitter 210 increases the weight and bulkiness of the scope head 201.

In contrast to the surgical microscope 200, the stereoscopic visualization camera 300 only contains optical paths for sensors, thereby reducing weight and bulkiness. In addition, the optical sensors receive the full incident light since beamsplitters are not needed to redirect a portion of the light. This means the image received by optical sensors of the example stereoscopic visualization camera 300 is as bright and clear as possible.

Some models of surgical microscopes may enable a video camera to be attached. For instance, the surgical microscope 200 of FIG. 2 includes a monoscopic video camera 212 connected to an optical path via beamsplitter 214. The video camera 212 may be monoscopic or stereoscopic, such as the Leica® TrueVision® 3D Visualization System Ophthalmology camera. The video camera 212 records an image received from the beamsplitter 214 for display on a display monitor. The addition of the video camera 212 and beamsplitter 214 further add to the weight of the scope head 201. In addition, the beamsplitter 214 consumes additional light destined for the oculars 206 and/or 208.

Each beamsplitter 210 and 214 divides the incident light fractionally into three paths, removing light from the surgeon's view. The surgeon's eye has limited low-light sensitivity such that light from the operative site presented to him/her must be sufficient to allow the surgeon to perform the procedure. However, a surgeon cannot always increase the intensity of light applied to a target site on a patient, especially in opthalmological procedures. A patient's eye has limited high-light sensitivity before it develops light toxicity. Hence, there is a limitation to the number and fraction of beamsplitters and to the amount of light which can be split off from the first oculars 206 to enable the use of ancillary devices 208 and 212.

The example stereoscopic visualization camera 300 of FIGS. 3 to 6 does not include beamsplitters such that optical imaging sensors receive the full amount of light from a main objective assembly. This enables the use of sensors with low-light sensitivity or even optical sensors with sensitivity outside the wavelengths of visible light to be used since post-processing can make the images sufficiently bright and visible (and adjustable) for display on the monitors.

Further, since the optical elements that define the optical paths are self-contained within the stereoscopic visualization camera 300, the optical elements may be controlled through the camera. This control allows placement and adjustment of the optical elements to be optimized for a three-dimensional stereoscopic display rather than for microscope oculars. This configuration of the camera permits control to be provided electronically from camera controls or from a remote computer. In addition, the control may be provided automatically through one or more programs onboard the camera 300 configured to adjust optical elements for retaining focus while zooming or to adjust for optical defects and/or spurious parallax. In contrast, optical elements of the surgical microscope 200 are external to the video camera 212 and controlled only via operator input, which is generally optimized for viewing a target site through the oculars 206.

In a final comparison, the surgical microscope 200 includes an X-Y panning device 220 for moving a field-of-view or target scene. The X-Y panning device 220 is typically a large, heavy, and expensive electromechanical module since it must rigidly support and move the surgical scope head 201. In addition, moving the scope head 201 changes the positioning of the surgeon to the new location of the oculars 206.

In contrast, the example stereoscopic visualization camera 300 includes a memory including instructions, which when executed, cause a processor to select pixel data of optical sensors to enable X-Y panning across a wide pixel grid. In addition, the example stereoscopic visualization camera 300 may include a small motor or actuator that controls a main objective optical element to change a working distance to a target site without moving the camera 300.

IV. Example Optical Elements of the Stereoscopic Visualization Camera

Figure 7:
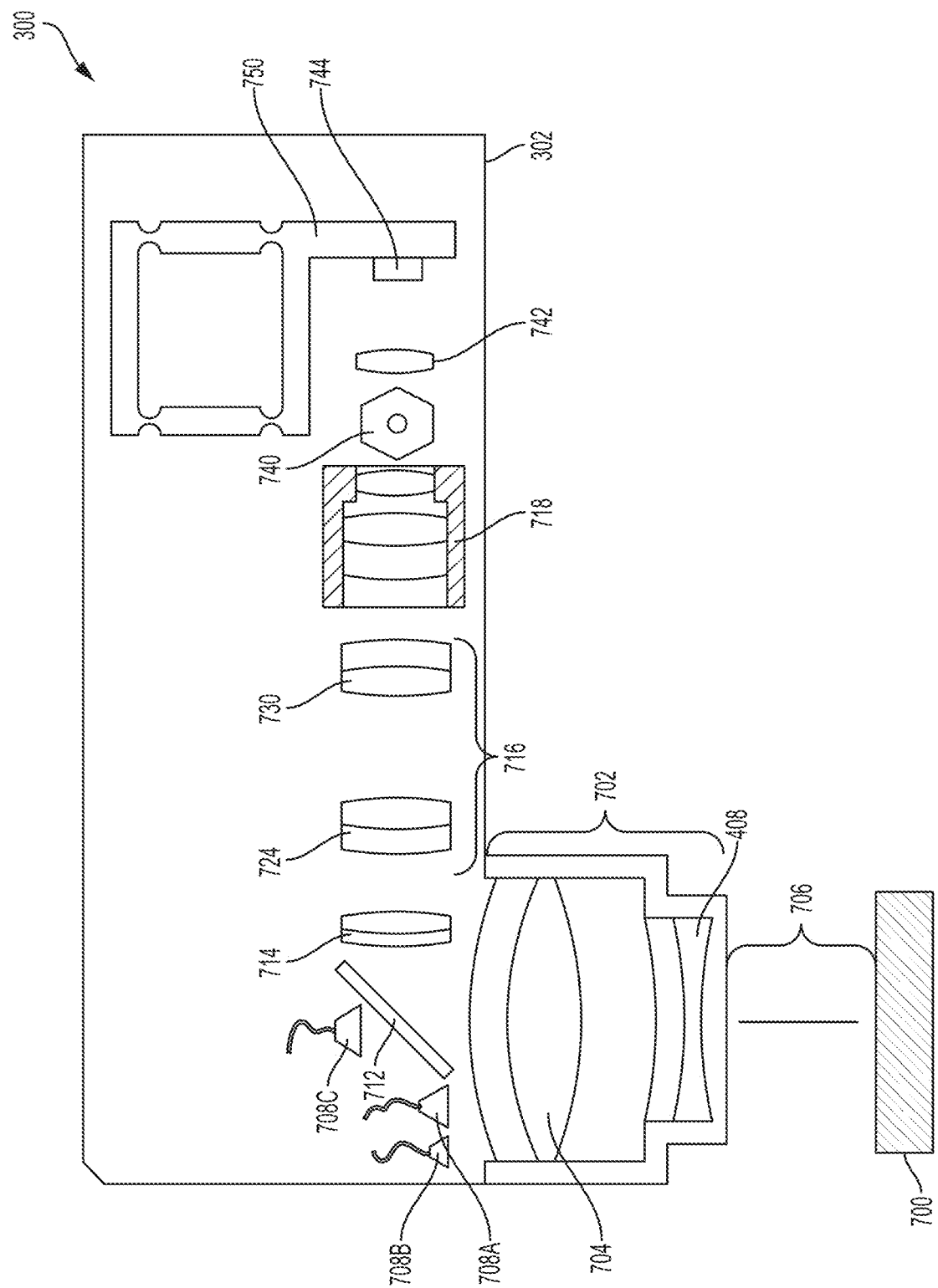
FIGS. 7 and 8 show diagrams illustrative of optical elements within the example stereoscopic visualization camera of FIGS. 3 to 6, according to an example embodiment of the present disclosure.
Figure 8:
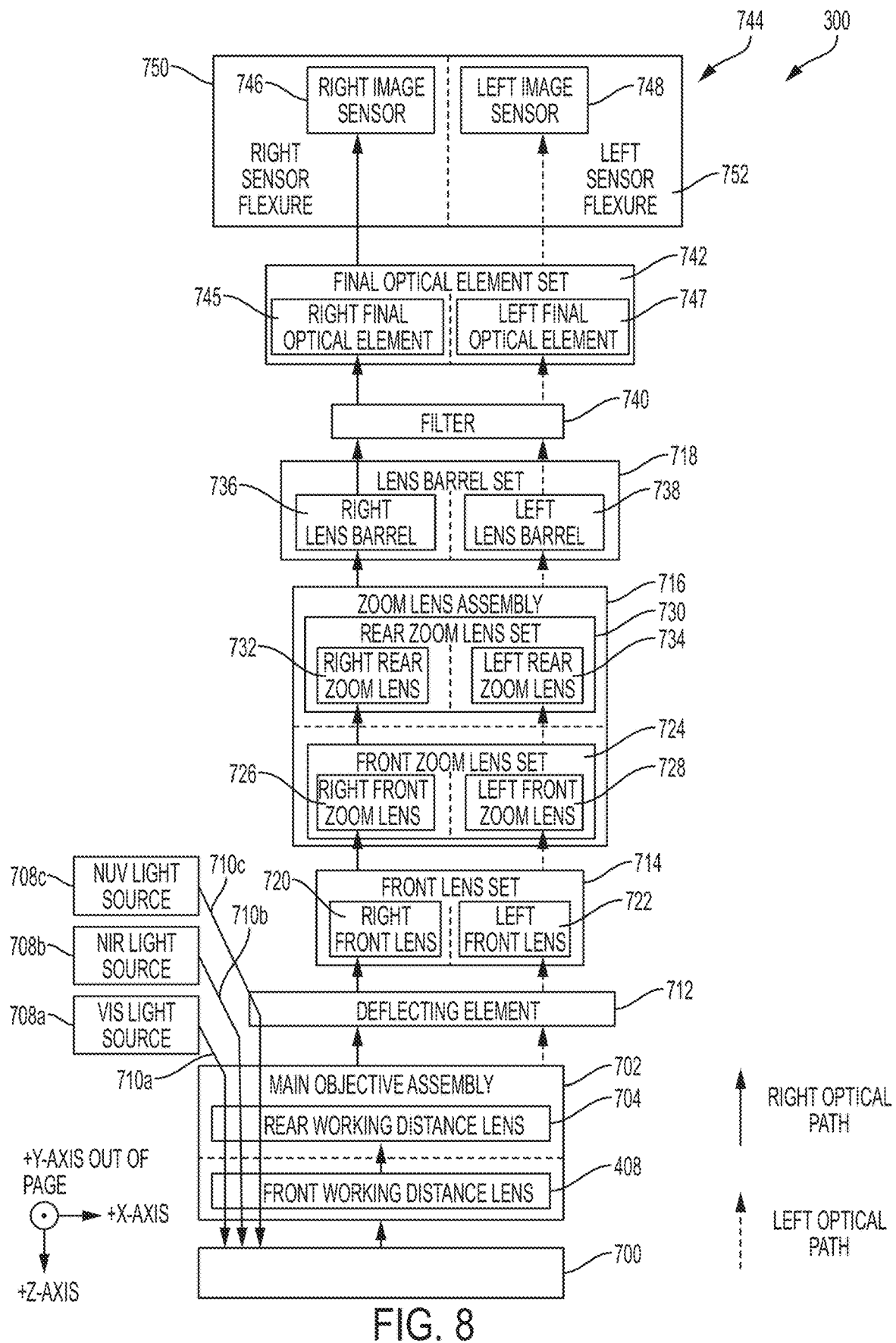

FIGS. 7 and 8 show diagrams illustrative of optical elements within the example stereoscopic visualization camera 300 of FIGS. 3 to 6, according to an example embodiment of the present disclosure. It may seem relatively simple to acquire left and right views of a target site to construct a stereoscopic image. However, without careful design and compensation, many stereoscopic images have alignment issues between the left and right views. When viewed for a prolonged period of time, alignment issues can create confusion in an observer's brain as a result of differences between the left and right views. This confusion can lead to headaches, fatigue, vertigo, and even nausea.

The example stereoscopic visualization camera 300 reduces (or eliminates) alignment issues by having a right optical path and left optical path with independent control and/or adjustment of some optical elements while other left and right optical elements are fixed in a common carrier. In an example embodiment, some left and right zoom lenses may be fixed to a common carrier to ensure left and right magnification is substantially the same. However, front or rear lenses may be independently adjustable radially, rotationally, axially, and/or tilted to compensate for small differences in zoom magnification, visual defects, and/or spurious parallax such as movement of a zoom repeat point. Compensation provided by adjustable lenses results in almost perfectly aligned optical paths throughout a complete zoom magnification range.

Additionally or alternatively, alignment issues may be reduced (or eliminated) using pixel readout and/or rendering techniques. For example, a right image (recorded by a right optical sensor) may be adjusted upwards or downwards with respect to a left image (recorded by a left optical sensor) to correct vertical misalignment between the images. Similarly, a right image may be adjusted left or right with respect to a left image to correct horizontal misalignment between the images.

FIGS. 7 and 8 below show an example arrangement and positioning of optical elements that provide for almost artifact, spurious parallax, and distortion-free aligned optical paths. As discussed later, certain of the optical elements may be moved during calibration and/or use to further align the optical paths and remove any remaining distortions, spurious parallax, and/or defects. In the illustrated embodiment, the optical elements are positioned in two parallel paths to generate a left view and a right view. Alternative embodiments may include optical paths that are folded, deflected or otherwise not parallel.

The illustrated paths correspond to a human's visual system such that the left view and right view, as displayed on a stereoscopic display, appear to be separated by a distance that creates a convergence angle of roughly 6 degrees, which is comparable to the convergence angle for an adult human's eyes viewing an object at approximately 4 feet away, thereby resulting in stereopsis. In some embodiments, image data generated from the left view and right view are combined together on the display monitor(s) 512 and 514 to generate a stereoscopic image of a target site or scene. Alternative embodiments comprise other stereoscopic displays where the left view is presented to only the left eye of a viewer and the corresponding right view is presented to only the right eye. In exemplary embodiments used to adjust and verify proper alignment and calibration, both views are displayed overlaid to both eyes.

A stereoscopic view is superior to a monoscopic view because it mimics the human visual system much more closely. A stereoscopic view provides depth perception, distance perception, and relative size perception to provide a realistic view of a target surgical site to a surgeon. For procedures such as retinal surgery, stereoscopic views are vital because surgical movements and forces are so small that the surgeon cannot feel them. Providing a stereoscopic view helps a surgeon's brain magnify tactile feel when the brain senses even minor movements while perceiving depth.

FIG. 7 shows a side view of the example stereoscopic visualization camera 300 with the housing 302 being transparent to expose the optical elements. FIG. 8 shows a diagram illustrative of an optical path provided by the optical elements shown in FIG. 7. As shown in FIG. 8, the optical path includes a right optical path and a left optical path. The optical paths in FIG. 8 are shown from a perspective of facing a forward direction and looking down at the stereoscopic visualization camera 300. From this view, the left optical path appear on the right side of FIG. 8 while the right optical path is shown on the left side.

The optical elements shown in FIG. 7 are part of the left optical path. It should be appreciated that the right optical path in FIG. 7 is generally identical to the left optical path regarding relation location and arrangement of optical elements. As mentioned above, the interpupillary distance between a center of the optical paths is between 58 to 70 mm, which may be scaled to 10 to 25 mm. Each of the optical elements comprise lenses having certain diameters (e.g., between 2 mm and 29 mm). Accordingly, a distance between the optical elements themselves is between 1 to 23 mm, preferably around 10 mm.

The example stereoscopic visualization camera 300 is configured to acquire images of a target site 700 (also referred to as a scene or field-of-view). The target site 700 includes an anatomical location on a patient. The target site 700 may also include laboratory biological samples, calibration slides/templates, etc. Images from the target site 700 are received at the stereoscopic visualization camera 300 via a main objective assembly 702, which includes the front working distance lens 408 (shown in FIG. 4) and a rear working distance lens 704.

A. Example Main Objective Assembly

The example main objective assembly 702 may include any type of refractive assembly or reflective assembly. FIG. 7 shows the objective assembly 702 as an achromatic refractive assembly with the front working distance lens 408 being stationary and the rear working distance lens 704 being movable along the z-axis. The front working distance lens 408 may comprise a plano convex ("PCX") lens and/or a meniscus lens. The rear working distance lens 704 may comprise an achromatic lens. In examples where the main objective assembly 702 includes an achromatic refractive assembly, the front working distance lens 408 may include a hemispherical lens and/or a meniscus lens. In addition, the rear working distance lens 704 may include an achromatic doublet lens, an achromatic doublet group of lenses, and/or an achromatic triplet lens.

The magnification of the main objective assembly 702 is between 6× to 20×. In some instances, the magnification of the main objective assembly 702 may vary slightly based on a working distance. For example, the main objective assembly 702 may have a magnification of 8.9× for a 200 mm working distance and a magnification of 8.75× for a 450 mm working distance.

The example rear working distance lens 704 is configured to be moveable with respect to the front working distance lens 408 to change a spacing therebetween. The spacing between the lenses 408 and 704 determines the overall front focal length of the main objective assembly 702, and accordingly the location of a focal plane. In some embodiments, the focal length is the distance between the lenses 408 and 704 plus one-half the thickness of the front working distance lens 408.

Together, the front working distance lens 408 and the rear working distance lens 704 are configured to provide an infinite conjugate image for providing an optimal focus for downstream optical image sensors. In other words, an object located exactly at the focal plane of the target site 700 will have its image projected at a distance of infinity, thereby being infinity-coupled at a provided working distance. Generally, the object appears in focus for a certain distance along the optical path from the focal plane. However, past the certain threshold distance, the object begins to appear fuzzy or out of focus.

FIG. 7 shows working distance 706, which is the distance between an outer surface of the front working distance lens 408 and to the focal plane of the target site 700. The working distance 706 may correspond to an angular field-of-view, where a longer working distance results in a wider field-of-view or larger viewable area. The working distance 706 accordingly sets a plane of the target site or scene that is in focus. In the illustrated example, the working distance 706 is adjustable from 200 to 450 mm by moving the rear working distance lens 704. In an example, the field-of-view can be adjusted between 20 mm×14 mm to 200 mm×140 mm using upstream zooming lenses when the working distance is 450 mm.

The main objective assembly 702 shown in FIGS. 7 and 8 provides an image of the target site 700 for both the left and right optical paths. This means that the width of the lenses 408 and 704 should be at least as wide as the left and right optical paths. In alternative embodiments, the main objective assembly 702 may include separate left and right front working distance lenses 408 and separate left and right rear working distance lens 704. The width of each pair of the separate working distance lenses may be between ¼ to ½ of the width of the lenses 408 and 704 shown in FIGS. 7 and 8. Further, each of the rear working distance lenses 704 may be independently adjustable.

In some embodiments, the main objective assembly 702 may be replaceable. For example, different main objective assemblies may be added to change a working distance range, a magnification, a numerical aperture, and/or refraction/reflection type. In these embodiments, the stereoscopic visualization camera 300 may change positioning of downstream optical elements, properties of optical image sensors, and/or parameters of image processing based on which main objective assembly is installed. An operator may specify which main objective assembly is installed in the stereoscopic visualization camera 300 using one of the controls 305 of FIG. 3 and/or a user input device.

B. Example Lighting Sources

To illuminate the target site 700, the example stereoscopic visualization camera 300 includes one or more lighting sources. FIGS. 7 and 8 show three lighting sources including a visible light source 708a, a near-infrared ("NIR") light source 708b, and a near-ultraviolet ("NUV") light source 708c. In other examples, the stereoscopic visualization camera 300 may include additional or fewer (or no) light sources. For instance, the NIR and NUV light sources may be omitted. The example light sources 708 are configured to generate light, which is projected to the target scene 700. The generated light interacts and reflects off the target scene, with some of the light being reflected to the main objective assembly 702. Other examples may include external light sources or ambient light from the environment.

The example visible light source 708a is configured to output light in the human-visible part of the light spectrum in addition to some light with wavelengths outside the visible region. The NIR light source 708b is configured to output light that is primarily at wavelengths slightly past the red part of the visible spectrum, which is also referred to as "near-infrared." The NUV light source 708c is configured to output light that is primarily at wavelengths in the blue part of the visible spectrum, which is referred to as "near-ultraviolet." The light spectra output by the light sources 708 is controlled by respective controllers, described below. A brightness of light emitted by the light sources 708 may be controlled by a switching rate and/or applied voltage waveform.

FIGS. 7 and 8 illustrate that the visible light source 708a and the NIR light source 708b are provided directly through the main objective assembly 702 to the target site 700. As shown in FIG. 8, visible light from the visible light source 708a propagates along visible path 710a. Additionally, NIR light from the NIR light source 708b propagates along NIR path 710b. While the light sources 708a and 708b are shown as being behind the main objective assembly 702 (with respect to the target site 700), in other examples the light sources 708a and 708b may be provided before the main objective assembly 702. In one embodiment, the light sources 708a and 708b may be provided on an outside of the housing 302 and face toward the target site 700. In yet other embodiments, the light sources 708 may be provided separate from the stereoscopic visualization camera 300 using, for example, a Koeher illumination setup and/or a darkfield illumination setup.

In contrast to the light sources 708a and 708b, NUV light from the NUV light source 708c is reflected by a deflecting element 712 (e.g., a beamsplitter) to the main objective assembly 702 using an epi-illumination setup. The deflecting element 712 may be coated or otherwise configured to reflect only light beyond the NUV wavelength range, thereby filtering NUV light. NUV light from the NUV light source 708c propagates along NUV path 710c.

In some embodiments, the NIR and NUV light sources 708b and 708c may be used with excitation filters to further filter light that may not be blocked by filters (e.g., filter 740). The filters may be placed in front of the light sources 708b and 708c before the main objective assembly 702 and/or after the main objective assembly. The light from the NUV and NIR light sources 708b and 708c, after being filtered, comprises wavelengths that excite fluorescence in fluorescent sites 914 (shown in FIG. 9) of an anatomical object. Further, the light from the NUV and NIR light sources 708b and 708c, after being filtered, may comprise wavelengths that are not in the same range as those being emitted by the fluorescent sites 914.

The projection of the light from light sources 708 through the main objective assembly provides the benefit of changing the lighted field-of-view based on the working distance 706 and/or focal plane. Since the light passes through the main objective assembly 702, the angle at which light is projected changes based on the working distance 706 and corresponds to the angular field-of-view. This configuration accordingly ensures the field-of-view is properly illuminated by the light sources 708, regardless of working distance or magnification.

C. Example Deflecting Element

The example deflecting element 712 illustrated in FIGS. 7 and 8 is configured to transmit a certain wavelength of light from the NUV light source 708c to the target site 700 through the main objective assembly 702. The deflecting element 712 is also configured to reflect light received from the target site 700 to downstream optical elements, including a front lens set 714 for zooming and recording. In some embodiments, the deflecting element 712 may filter light received from the target site 700 through the main objective assembly 702 so that light of certain wavelengths reaches the front lens set 714.

The deflecting element 712 may include any type of mirror or lens to reflect light in a specified direction. In an example, the deflecting element 712 includes a dichroic mirror or filter, which has different reflection and transmission characteristics at different wavelengths. The stereoscopic visualization camera 300 of FIGS. 7 and 8 includes a single deflecting element 712, which provides light for both the right and left optical paths. In other examples, the camera 300 may include separate deflecting elements for each of the right and left optical paths. Further, a separate deflecting element may be provided for the NUV light source 708c.

Figure 9:
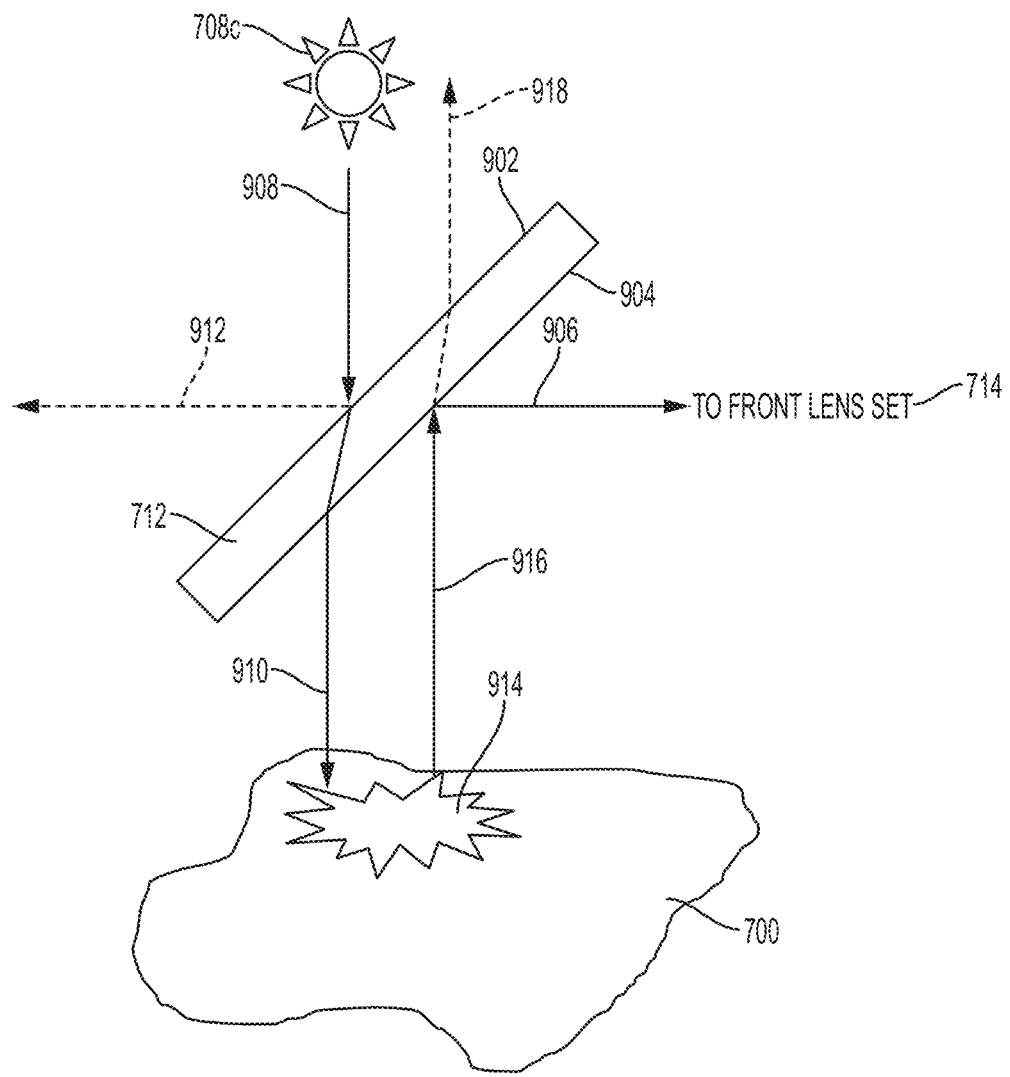
FIG. 9 shows a diagram of a deflecting element of the example stereoscopic visualization camera of FIGS. 7 and 8, according to an example embodiment of the present disclosure.

FIG. 9 shows a diagram of the deflecting element 712 of FIGS. 7 and 8, according to an example embodiment of the present disclosure. For brevity, the main objective assembly 702 is not shown. In this example, the deflecting element 712 includes two parallel faces 902 and 904 for transmitting and reflecting light of certain wavelengths. The parallel faces 902 and 904 are set at a 45° angle with respect to the left and right optical paths (represented as path 906). The 45° angle is selected since this angle causes reflected light to propagate at a 90° angle from the transmitted light, thereby providing optimal separation without causing the separated light to be detected in the downstream front lens set 714. In other embodiments, the angle of the deflecting element 712 could be between 10 degrees and 80 degrees without unintentionally propagating light of unwanted wavelengths.

The example NUV light source 708c is located behind the deflecting element 712 (with respect to the target site 700). Light from the light source 708c propagates along path 908 and contacts the deflecting element 712. NUV light around the primary wavelength range of the NUV light source 708c is transmitted through the deflecting element 712 along path 910 to the target site 700. Light from the NUV light source 708c that has a wavelength above (and below) the primary wavelength range of the NUV light source 708c is reflected along path 912 to a light sink or unused region of the housing 302.

When the NUV light reaches the target site 700, it is absorbed by one or more fluorescent sites 914 of an anatomical object. In some instances, the anatomical object may have been injected with a contrast agent configured to absorb NUV light and emit light with a different primary wavelength. In other instances, the anatomical object may naturally absorb NUV light and emit light with a different primary wavelength. At least some of the light reflected or emitted by the fluorescent site 914 propagates along path 916 until it contacts the deflecting element 712. Most of the light reflects off the surface 904 along path 906 to the front lens set 714. A portion of the light, including NUV light around the primary wavelength range of the NUV light source 708c is transmitted through the deflecting element 712 along path 918 to a light sink or unused region of the housing 302. The deflecting element 712 shown in FIG. 9 accordingly enables optical stimulation of a fluorescent agent at the target site 700 with one region of the spectrum while blocking much of the stimulating light from travelling to the downstream front lens set 714.

It should be appreciated that the reflectivity and transmissivity characteristics of the deflecting element 712 can be changed to meet other light spectrum requirements. In some instances, the housing 302 may include a slot that enables the deflecting element 712 and/or the NUV light source 708c to be replaced based on the desired light reflectivity and transmissivity characteristics. It should also be appreciated that a first path internal to the deflecting element 712 between path 908 and path 910 and a second path internal to the deflecting element 712 between path 916 and path 918 are each angled to represent schematically the refraction of the light as it travels between air and the interior of the deflecting element 712. The angles shown are not meant to represent actual reflection angles.

D. Example Zoom Lenses

The example stereoscopic visualization camera 300 of FIGS. 7 and 8 includes one or more zoom lens to change a focal length and angle of view of the target site 700 to provide zoom magnification. In the illustrated example, the zoom lens includes the front lens set 714, a zoom lens assembly 716, and a lens barrel set 718. It should be appreciated that in other embodiments, the front lens set 714 and/or the lens barrel set 718 may be omitted. Alternatively, the zoom lens may include additional lens to provide further magnification and/or image resolution.

The front lens set 714 includes a right front lens 720 for the right optical path and a left front lens 722 for the left optical path. The lenses 720 and 722 may each include a positive converging lens to direct light from the deflecting element 712 to respective lenses in the zoom lens assembly 716. A lateral position of the lenses 720 and 722 accordingly defines a beam from the main objective assembly 702 and the deflecting element 712 that is propagated to the zoom lens assembly 716.

One or both of the lenses 720 and 722 may be adjustable radially to match optical axes of the left and right optical paths. In other words, one or both of the lenses 720 and 722 may be moved left-right and/or up-down in a plane incident to the optical path. In some embodiments, one or more of the lenses 720 and 722 may be rotated or tilted to reduce or eliminate image optical defects and/or spurious parallax. Moving either or both of the lenses 720 and 722 during zooming may cause the zoom repeat point ("ZRP") for each optical path to appear to remain stationary to a user. In addition to radial movement, one or both of the front lenses 720 and 722 may be moved axially (along the respective optical path) to match magnifications of the optical paths.

The example zoom lens assembly 716 forms an afocal zoom system for changing the size of a field-of-view (e.g., a linear field-of-view) by changing a size of the light beam propagated to the lens barrel set 718. The zoom lens assembly 716 includes a front zoom lens set 724 with a right front zoom lens 726 and a left front zoom lens 728. The zoom lens assembly 716 also includes a rear zoom lens set 730 with a right rear zoom lens 732 and a left rear zoom lens 734. The front zoom lenses 726 and 728 may be positive converging lenses while the rear zoom lenses 732 and 734 include negative diverging lenses.

The size of an image beam for each of the left and right optical paths is determined based on a distance between the front zoom lenses 726 and 728, the rear zoom lenses 732 and 734 and the lens barrel set 718. Generally, the size of the optical paths reduces as the rear zoom lenses 732 and 734 move toward the lens barrel set 718 (along the respective optical paths), thereby decreasing magnification. In addition, the front zoom lenses 726 and 728 may also move toward (or away from) the lens barrel set 718 (such as in a parabolic arc), as the rear zoom lenses 732 and 734 move toward the lens barrel set 718, to maintain the location of the focal plane on the target site 700, thereby maintaining focus.

The front zoom lenses 726 and 728 may be included within a first carrier (e.g., the front zoom set 724) while the rear zoom lenses 732 and 724 are included within a second carrier (e.g., the rear zoom set 730). Each of the carriers 724 and 730 may be moved on tracks (or rails) along the optical paths such that left and right magnification changes concurrently. In this embodiment, any slight differences in magnification between the left and right optical paths may be corrected by moving the right front lens 720 and/or the left front lens 722. Additionally or alternatively, a right lens barrel 736 and/or a left lens barrel 738 of the lens barrel set 718 may be moved axially.

In alternative embodiments, the right front zoom lens 726 may be moved axially separately from the left front zoom lens 728. In addition, the right rear zoom lens 732 may be moved axially separately from the left rear zoom lens 734. Separate movement may enable small magnification differences to be corrected by the zoom lens assembly 716, especially when the front lens set 714 and the lens barrel set 718 are stationary along the optical paths. Further, in some embodiments, the right front zoom lens 726 and/or the left front zoom lens 728 may be radially and/or rotationally adjustable (and/or tilted) to maintain an apparent location of a ZRP in the optical path. Additionally or alternatively, the right rear zoom lens 732 and/or the left rear zoom lens 734 may be radially and/or rotationally adjustable (and/or tilted) to maintain an apparent location of a ZRP in the optical path.

The example lens barrel set 718 includes the right lens barrel 736 and the left lens barrel 738, which are part of the afocal zoom system in addition with the zoom lens assembly 716. The lenses 736 and 738 may include positive converging lenses configured to straighten or focus a light beam from the zoom lens assembly 716. In other words, the lenses 736 and 738 focus the infinity-coupled output of the zoom lens assembly 716.

In some examples, the lens barrel set 718 is fixed radially and axially within the housing 302. In other examples, the lens barrel set 718 may be moveable axially along the optical path to provide increased magnification. Additionally or alternatively, each of the lenses 736 and 738 may be radially and/or rotationally adjustable (and/or tilted) to, for example, correct for differences in optical properties (from manufacturing or natural glass deviations) between the left and right lenses of the front lens set 714, the front zoom lens set 724, and/or the rear zoom lens set 730.

Altogether, the example front lens set 714, the zoom lens assembly 716, and the lens barrel set 718 are configured to achieve an optical zoom between 5× to about 20×, preferably at a zoom level that has diffraction-limited resolution. In some embodiments, the front lens set 714, the zoom lens assembly 716, and the lens barrel set 718 may provide higher zoom ranges (e.g., 25X to 100X) if image quality can be compromised. In these embodiments, the stereoscopic visualization camera 300 may output a message to an operator indicative that a selected optical range is outside of an optical range and subject to a reduction in image quality.

In some embodiments, the lenses of the front lens set 714, the zoom lens assembly 716, the lens barrel set 718, and/or the main objective assembly 702 may each be constructed as a doublet from multiple optical sub-elements using materials that balance each other's optical distortion parameters. The doublet construction reduces chromatic aberrations and optical aberrations. For example, the front working distance lens 408 and the rear working distance lens 702 may each be constructed as a doublet. In another example, the front lenses 720 and 722, the front zoom lenses 726 and 728, the rear zoom lenses 732 and 734, and the lens barrels 736 and 738 may each comprise a doublet lens.

In yet further embodiments, the lenses of the front lens set 714, the zoom lens assembly 716, the lens barrel set 718, and/or the main objective assembly 702 may be tuned differently and/or have different properties to provide two parallel optical paths with different capabilities. For example, right lenses in zoom lens assembly 716 may be selected to provide 5× to 10× optical zoom for the right optical path while left lenses in the zoom lens assembly 716 are selected to provide 15× to 20× optical zoom for the left optical path. Such a configuration may enable two different magnifications to be shown at the same time and/or on the same screen, though in a monoscopic view.

E. Example Filter

The example stereoscopic visualization camera 300 of FIGS. 7 and 8 includes one or more optical filters 740 (or filter assemblies) to selectively transmit desired wavelengths of light. FIG. 8 shows that a single filter 740 may be applied to the right and left optical paths. In other examples, each of the optical paths may have a separate filter. The inclusion of separate filters enables, for example, different wavelengths of light to be filtered from the left and right optical paths at the same time, which enables, for example, fluorescent images to be displayed in conjunction with visible light images.

FIG. 7 shows that the filter 740 includes a magazine that is rotated about its axis of rotation. In the illustrated embodiment, the filter 740 can accommodate three different optical filter pairs. However, in other embodiments, the filter 740 may include additional or fewer filter pairs. Generally, light received at the filter 740 from the target site 700 includes a broad spectrum of wavelengths. The lenses of the main objective assembly 702, the front lens set 714, the zoom lens assembly 716, and the lens barrel set 718 are configured to pass a relatively wide bandwidth of light including wavelengths of interest to an operator and undesirable wavelengths. In addition, downstream optical image sensors are sensitive to certain wavelengths. The example filter 740 accordingly passes and blocks certain portions of the light spectrum to achieve different desirable features.

As a magazine, the filter 740 comprises a mechanical device capable of changing positions at about four times per second. In other embodiments, the filter 740 may include a digital micro-mirror, which can change a light path's direction at video frame rates such as 60 times per second. In these other embodiments, each of the left and right optical paths would include a micro-mirror. The left and right micro-mirror may have synchronized or simultaneous switching.

In some embodiments, the filter 740 may be synchronized to the light sources 708 to realize "time-interleaved" multispectral imaging. For example, the filter 740 may include an infrared cut filter, near-infrared bandpass filter, and near-ultraviolet cut filter. The different filter types are selected to work with different spectra of the light sources 708 and the reflectivity and transmissivity characteristics of the deflecting element 712 to pass certain desired wavelengths of light at predetermined times.

In one mode, the filter 740 and the light sources 708 are configured to provide a visible light mode. In this mode, the visible light source 708a transmits light from the visible region onto the target site 700, some of which is reflected to the main objective assembly 702. The reflected light may include some light beyond the visible spectrum, which may affect optical image sensors. The visible light is reflected by the deflecting element 712 and passes through the front lens set 714, the zoom lens assembly 716, and the lens barrel set 718. In this example, the filter 740 is configured to apply the infrared cut filter or the near-ultraviolet cut filter to the optical paths to remove light outside the visible spectrum such that light only in the visible spectrum passes through to a final optical set 742 and an optical image sensor 744.

In another mode, filter 740 and the light sources 708 are configured to provide fluorescence light of a narrow wavelength to the optical sensor 744. In this mode, the NUV light source 708c transmits light from the deep-blue region of the spectrum to the target site 700. The deflecting element 712 allows the desired light of the deep-blue region to pass through while reflecting undesired light. The deep-blue light interacts with the target site 700 such that fluorescence light is emitted. In some examples, δ-Aminolaevulinic acid ("Sala") and/or Protoporphyrin IX is applied to the target site 700 to cause fluorescence light to be emitted when deep-blue light is received. The main objective assembly 702 receives the fluorescence light in addition to reflected deep-blue light and some visible light. The deep-blue light passes through the deflecting element 712 out of the right and left optical paths. Thus, only the visible light and fluorescence light pass through the front lens set 714, the zoom lens assembly 716, and the lens barrel set 718. In this example, the filter 740 is configured to apply the near-ultraviolet cut filter to the optical paths to remove light outside the desired fluorescence spectrum including visible light and any remaining NUV deep-blue light. Accordingly, only fluorescence light of a narrow wavelength reaches the optical image sensor 744, which enables the fluorescence light to be more easily detected and distinguished based on relative intensity.

In yet another mode, the filter 740 and the light sources 708 are configured to provide indocyanine green ("ICG") fluorescence light to the optical sensor 744. In this mode, the NIR light source 708b transmits light in the far-red region (which is also considered near-infrared) of the visible spectrum to the target site 700. In addition, the visible light source 708a transmits visible light to the target scene 700. The visible light and far-red light are absorbed by material with ICG at the target site, which then emits a highly stimulated fluorescence light in the further-red region. The main objective assembly 702 receives the fluorescence light in addition to reflected NIR light and visible light. The light is reflected by the deflecting element 712 to the front lens set 714, the zoom lens assembly 716, and the lens barrel set 718. In this example, the filter 740 is configured to apply the near-infrared bandpass filter to the optical paths to remove light outside the desired fluorescence spectrum including visible light and at least some of the NIR light. Accordingly, only fluorescence light in the further-red region reaches the optical image sensor 744, which enables the fluorescence light to be more easily detected and distinguished based on relatively intensity.

TABLE 1

| Light Source | Filter | Light Transmitted to Image Sensors |
|---|---|---|
| Visible | Infrared Cut Filter, Near-Ultraviolet Cut Filter | Visible Light |
| NUV | Near-Ultraviolet Cut Filter | Blue Visible and NIR Light |
| NIR and Visible | Near-Infrared Bandpass Filter | Further-Red Fluorescence |

Table 1 above shows a summary of the different possible combinations of lights sources and filters for causing light of a certain desired wavelength to reach the optical light sensor 744. It should be appreciated that other types of filters and/or light sources may be used to further increase the different types of light received at the image sensor 744. For instance, bandpass filters configured to pass light of a narrow wavelength may be used to correspond to certain biological stains or contrasts applied to the target site 700. In some examples, the filter 740 may include a cascade or more than one filter to enable light from two different ranges to be filtered. For example, a first filter 740 may apply an infrared cut filter and a near-ultraviolet cut filter such that only visible light of a desired wavelength range passes to the optical sensor 744.

In other embodiments, separate filters 740 may be used for the left and right optical paths. For example, a right filter may include an infrared cut filter while a left filter includes a near-infrared pass filter. Such a configuration enables viewing of the target site 700 in visible wavelengths simultaneously with IGC green fluorescence wavelengths. In another example, a right filter may include an infrared cut filter while a left filter includes a near-ultraviolet cut filter. In this configuration, the target site 700 may be shown in visible light simultaneously with SALA fluorescence light. In these other embodiments, the right and left image streams may still be combined into a stereoscopic view that provides a fluorescence view of certain anatomical structures combined with a view of the target site 700 in visible light.

F. Example Final Optical Element Set

The example stereoscopic visualization camera 300 of FIGS. 7 and 8 includes the final optical element set 742 to focus light received from the filter 740 onto the optical image sensor 744. The final optical element set 742 includes a right final optical element 745 and a left final optical element 747, which may each comprise a positive converging lens. In addition to focusing light, the optical elements 745 and 747 may be configured to correct minor aberrations in the right and left optical paths prior to the light reaching the optical image sensor 744. In some examples, the lenses 745 and 747 may be moveable radially and/or axially to correct magnification and/or focusing aberrations caused by the front lens set 714, the zoom lens assembly 716, and the lens barrel set 718. In an example, the left final optical element 747 may be moved radially while the right final optical element 745 is fixed to remove ZRP movement during magnification changes.

G. Example Image Sensors

The example stereoscopic visualization camera 300 of FIGS. 7 and 8 includes the image sensor 744 to acquire and/or record incident light that is received from the final optical element set 742. The image sensor 744 includes a right optical image sensor 746 to acquire and/or record light propagating along the right optical path and a left optical image sensor 748 to acquire and/or record light propagating along the left optical path. Each of the left and right optical image sensors 746 and 748 include, for example, complementary metal-oxide-semiconductor ("CMOS") sensing elements, N-type metal-oxide-semiconductor ("NMOS"), and/or semiconductor charge-coupled device ("CCD") sensing elements. In some embodiments, the left and right optical sensors 746 and 748 are identical and/or have the same properties. In other embodiments, the left and right optical sensors 746 and 748 include different sensing elements and/or properties to provide varying capability. For example, the right optical image sensor 746 (using a first color filter array) may be configured to be more sensitive to blue fluorescence light while the left optical image sensor 748 (using a second color filter array) is configured to be more sensitive to visible light.

Figure 10:
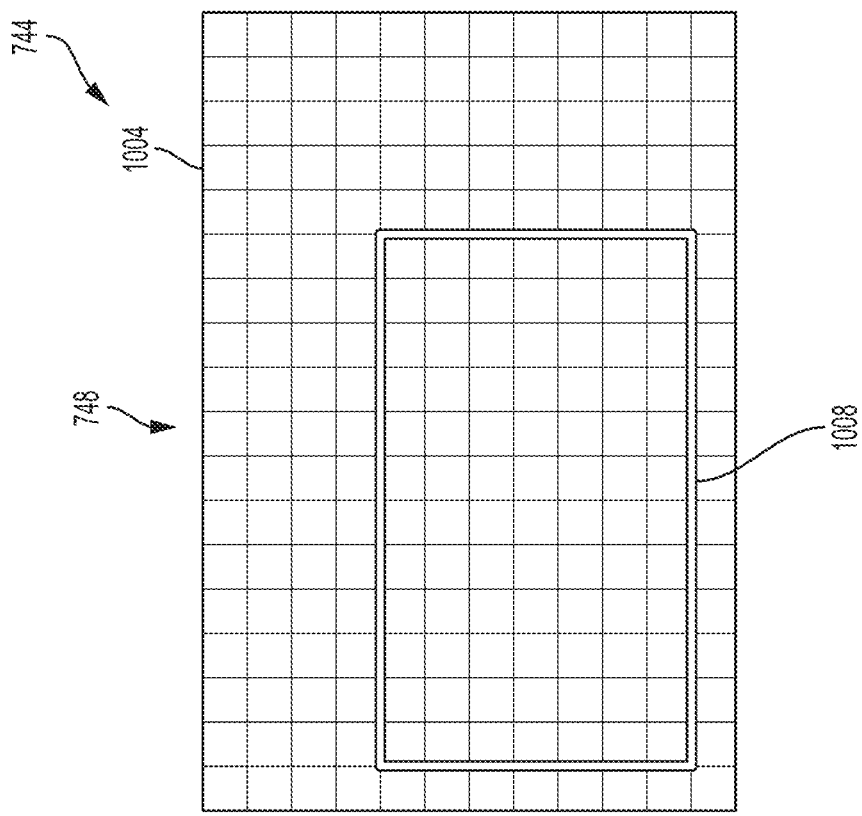
FIG. 10 shows a diagram of an example of a right optical image sensor and a left optical image sensor of the example stereoscopic visualization camera of FIGS. 7 and 8, according to an example embodiment of the present disclosure.
Figure 10:
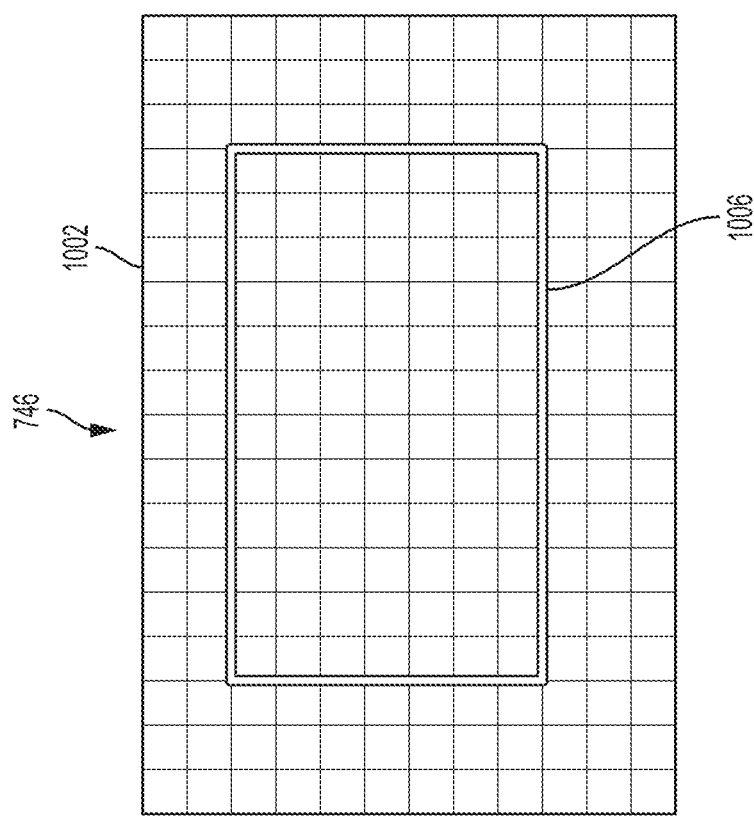

FIG. 10 shows an example of the right optical image sensor 746 and the left optical image sensor 748 of the image sensor 744, according to an example embodiment of the present disclosure. The right optical image sensor 746 includes a first two-dimensional grid or matrix 1002 of light-sensing elements (e.g., pixels). In addition, the left optical image sensor 748 includes a second two-dimensional pixel grid 1004 of light-sensing elements. Each of the pixels includes a filter that enables only light of a certain wavelength to pass, thereby contacting an underlying light detector. Filters for different colors are spread across the sensors 746 and 748 to provide light detection for all wavelengths across grids. The light detector may be sensitive to visible light, as well as additional ranges that are above and below the visible spectrum.

The light-sensing elements of the grids 1002 and 1004 are configured to record a range of wavelengths of light as a representation of the target site 700 that is in the field-of-view. Light incident on a light-sensing element causes an electrical change to accumulate. The electrical charge is read to determine an amount of light being received at the sensing element. In addition, since the filter characteristics of the sensing element are known to within manufacturing tolerances, the range of wavelengths of the received light is known. The representation of the target site 700 is directed onto the light-sensing elements such that the grids 1002 and 1004 for the respective optical image sensors 746 and 748 sample the target site 700 spatially. The resolution of the spatial sampling is a parameter that affects image quality and parity.

The number of pixels shown in the pixel grids 1002 and 1004 in FIG. 10 is not representative of the number of actual pixels in the optical image sensors 746 and 748. Instead, the sensors typically have a resolution between 1280×720 pixels and 8500×4500 pixels, preferably around 2048×1560 pixels. However, not all pixels of the grids 1002 and 1004 are selected for image transmission. Instead, a subset or pixel set of the grids 1002 and 1004 are selected for transmission. For example, in FIG. 10, pixel set 1006 is selected from the pixel grid 1002 for transmission as a right image and pixel set 1008 is selected from pixel grid 1004 for transmission as a left image. As illustrated, the pixel set 1006 does not need to be located in the same location as the pixel set 1008 in relation to respective pixel grids 1002 and 1004. The separate control of the pixel sets 1006 and 1008 enables left and right images to be aligned and/or corrected for image defects and/or spurious parallax such as moving ZRPs.

Selection of a pixel set from a pixel grid enables a portion of the pixel grid to be selected to compensate for image defects/spurious parallax and/or to more align the right and left optical images. In other words, the pixel set may be moved or adjusted (in real-time) with respect to the pixel grid to improve image quality by reducing or eliminating spurious parallax. Alternatively, either or both of the left and right views of the stereoscopic image can be moved virtually in the image processing pipeline (for example during rendering of the views for display) to accomplish the same effect. Rotational misalignment of the sensors can also be corrected virtually. A pixel set may also be moved across a pixel grid during use to provide an appearance of panning the field-of-view. In an example, a pixel set or window of 1920×1080 pixels may be selected from a pixel grid having 2048×1560 pixels. The location of the pixel window or set may be controlled by software/firmware and be moved during setup and/or use. The resolution of the optical image sensors 746 and 748 is accordingly specified based on a number of pixels in the length and width directions of the pixel set or window.

1. Color Sensing with the Example Image Sensors

As mentioned above, the optical sensing elements 746 and 748 include pixels with different filters to detect certain colors of light. For instance, some pixels are covered with filters that pass predominantly red light, some are covered with filters that pass predominantly green light, and some are covered with filters that pass predominantly blue light. In some embodiments, a Bayer pattern is applied to the pixel grids 1002 and 1004. However, it should be appreciated that in other embodiments, a different color pattern may be used that is optimized for certain wavelengths of light. For example, a green filter in each sensing region may be replaced with a broadband filter or a near-infrared filter, thereby extending the sensing spectrum.

The Bayer pattern is implemented by grouping two rows by two columns of pixels and covering one with a red filter, one with a blue filter, and two with a green filter, each in a checkerboard pattern. Thus the resolution of red and blue are each one quarter of the whole sensing region of interest while green resolution is half that of the whole sensing region of interest.

Green may be assigned to half the sensing region to cause the optical image sensors 746 and 748 to operate as a luminance sensor and mimic the human visual system. In addition, red and blue mimic chrominance sensors of the human visual system, but are not as critical as green sensing. Once an amount of red, green, and blue are determined for a certain region, other colors in the visible spectrum are determined by averaging the red, green, and blue values, as discussed in conjunction with de-Bayer program 1580a of FIG. 16 discussed below.

In some embodiments, the optical image sensors 746 and 748 may use stacked components to sense color rather than filters. For example, sensing elements may include red, green and blue sensing components stacked vertically inside a pixel's area. In another example, prisms split incident light into components using specially coated beamsplitters one or more times (typically at least two times resulting in three component colors, known as "3-chip") with sensing elements placed in each of the split beams' paths. Other sensor types use a different pattern such as replacing one of the green filters with a broadband filter or a near-infrared filter, thereby extending the sensing possibilities of the digital surgical microscope.

2. Sensing Light Outside the Visible Range with the Example Image Sensors

The example sensing element filters of the optical image sensors 746 and 748 are configured to also pass near-infrared light in a range that the sensing element can detect. This enables the optical image sensors 746 and 748 to detect at least some light outside of the visible range. Such sensitivity may decrease image quality in the visible part of the spectrum because it "washes out" the image, reducing contrast in many types of scenes and negatively affecting the color quality. As a result, the filter 740 may use the infrared cut filter to block near infrared wavelengths while passing the visible wavelengths to the optical image sensors 746 and 748.

However, such near-infrared sensitivity may be desirable. For example, a fluorescent agent, such ICG, can be introduced to the target site 700. ICG becomes excited or activated with visible or other wavelengths or light and emits fluorescence light in the near infrared range. As mentioned above, the NIR light source 708b provides NIR light and the visible light source 708a provides visible light to excite agents with ICG. Emitted light is further along the red spectrum, which may be passed through the filter 740 using a near-infrared bandpass or high-pass filter. The light from the red spectrum then is detected by the optical image sensors 746 and 748. By matching the spectral characteristics of the filter 740 to the expected behaviors of the light source 708 and the fluorescent agent, the agent and the biological structures, such as blood that contain the agent, can be differentiated at the target site 700 from other structures that do not contain the agent.

Note that in this example, the NIR light source 708b has a different primary wavelength from the near-infrared filter in the filter 740. Specifically, the NIR light source 708b has a primary wavelength around 780 nanometers ("nm") (around which the majority of the light's output spectrum exists). In contrast, the near-infrared filter of the filter 740 transmits light at wavelengths in a range of approximately 810 nm to 910 nm. The light from the NIR light source 708b and light passed through the filter 740 are both "near-infrared" wavelengths. However, the light wavelengths are separated so that the example stereoscopic visualization camera 300 can stimulate with the light source 708 and detect with the optical image sensor 744 while filtering the stimulation light. This configuration accordingly enables the use of fluorescent agents.

In another embodiment, agents can be excited in the blue, violet, and near-ultraviolet region and fluoresce light in the red region. An example of such an agent includes porphyrin accumulation in malignant gliomas caused by the introduction of SALA. In this example, it is necessary to filter out the blue light while passing the remainder of the spectrum. A near-ultraviolet cut filter is used for this situation. As in the case with "near-infrared" discussed above, the NUV light source 708c has a different primary wavelength from the near-ultraviolet cut filter in the filter 740.

H. Example Lens Carrier

Section IV(D) above mentions that at least some of the lenses of the front lens set 714, the zoom lens assembly 716, and/or the lens barrel set 718 may move in one or more carriers along rails. For example, the front zoom lens set 724 may comprise a carrier that moves front zoom lens 726 and 728 together axially.

Figure 11:
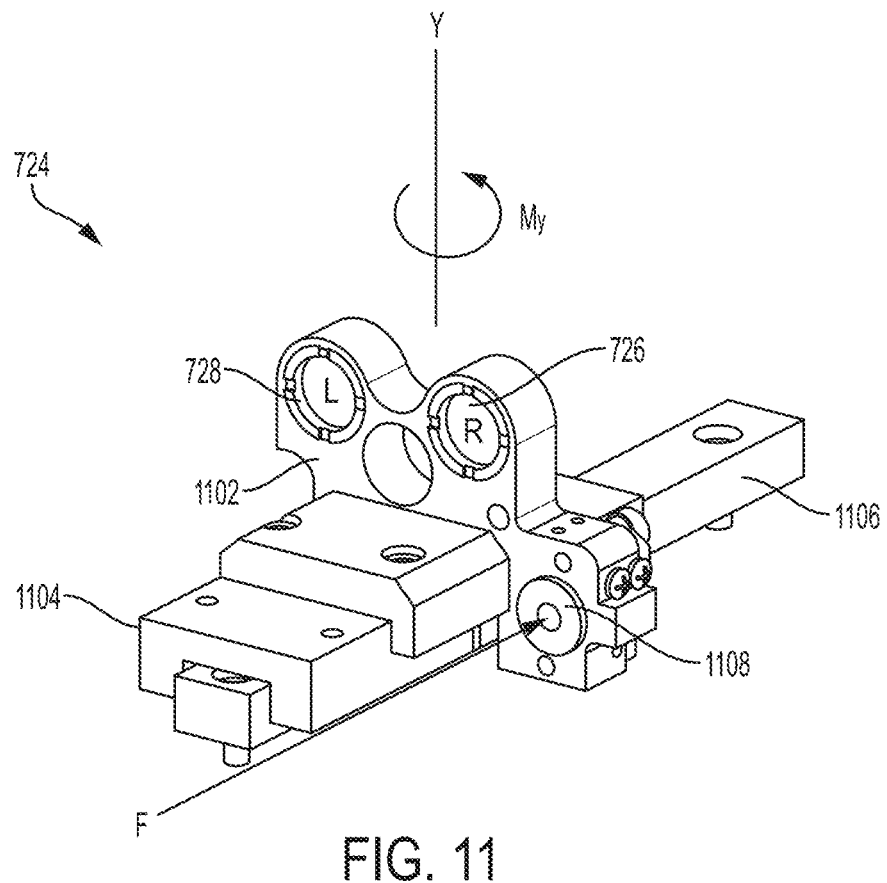
FIGS. 11 and 12 show diagrams of example carriers for optical elements of the example stereoscopic visualization camera of FIGS. 7 and 8, according to example embodiments of the present disclosure.
Figure 12:
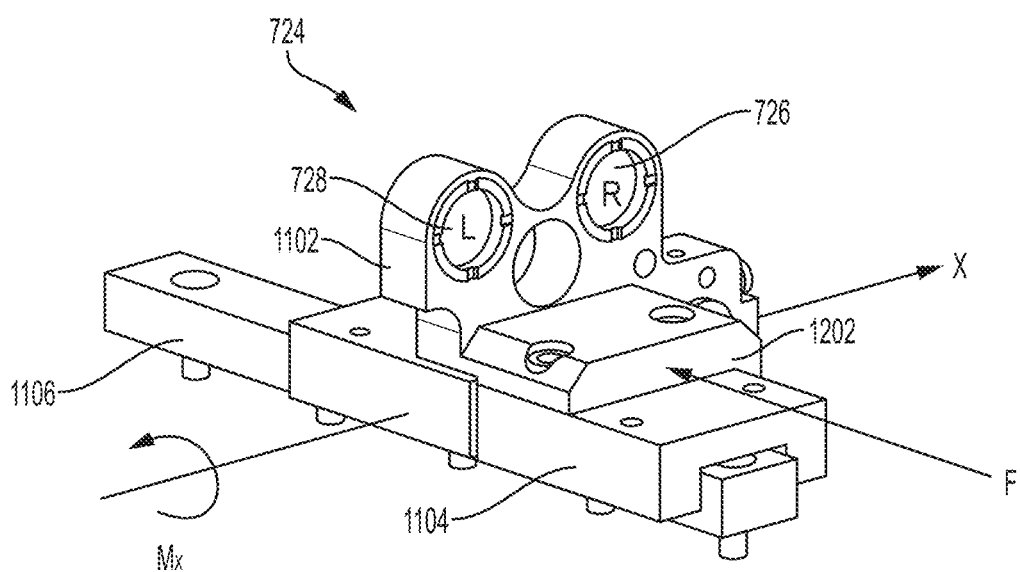

FIGS. 11 and 12 show diagrams of example carriers, according to example embodiments of the present disclosure. In FIG. 11, carrier 724 includes the right front zoom lens 726 and the left front zoom lens 728 within a support structure 1102. The carrier 724 includes a rail holder 1104 configured to moveably connect to rail 1106. A force 'F' is applied to an actuation section 1108 to cause the carrier 724 to move along the rail 1106. The force 'F' may be applied by a leadscrew or other linear actuation device. As illustrated in FIG. 11, the force 'F' is applied at an offset of the carrier 724. Friction between the rail 1106 and the carrier 724 generates a moment My that causes the support structure 1102 to move slightly around the Y-axis shown in FIG. 11. This slight movement may cause the right front zoom lens 726 and the left front zoom lens 728 to shift slightly in opposite directions causing spurious parallax, which is an error in a parallax between views of a stereoscopic image.

FIG. 12 shows another example of the carrier 724. In this example, force 'F' is applied symmetrically at center structure 1202, which is connected to the rail holder 1104 and the support structure 1102. The force 'F' generates a moment $M_x$ that causes the carrier 724 to rotate or move slightly around the X-axis shown in FIG. 12. The rotational movement causes the right front zoom lens 726 and the left front zoom lens 728 to shift in the same direction by the same degree of movement, thereby reducing (or eliminating) the onset of spurious parallax.

While FIGS. 11 and 12 show lenses 726 and 728 within one carrier, in other embodiments the lenses 726 and 728 may each be within a carrier. In these examples, each lens would be on a separate track or rail. Separate leadscrews may be provided for each of the lenses to provide independent axial movement along the respective optical path.

I. Example Flexure

Section IV(D) above mentions that at least some of the lenses of the front lens set 714, the zoom lens assembly 716, and/or the lens barrel set 718 may be moved radially, rotated, and/or tilted. Additionally or alternatively, the optical image sensors 746 and 748 may be moved axially and/or tilted with respect to their respective incident optical path. The axial and/or tilt movement may be provided by one or more flexures. In some examples, the flexures may be cascaded such that a first flexure provides motion in a first direction and separate flexure provides independent motion in a second direction. In another example, a first flexure provides tilt along a pitch axis and separate flexure provides tilt along a yaw axis.

Figure 13:
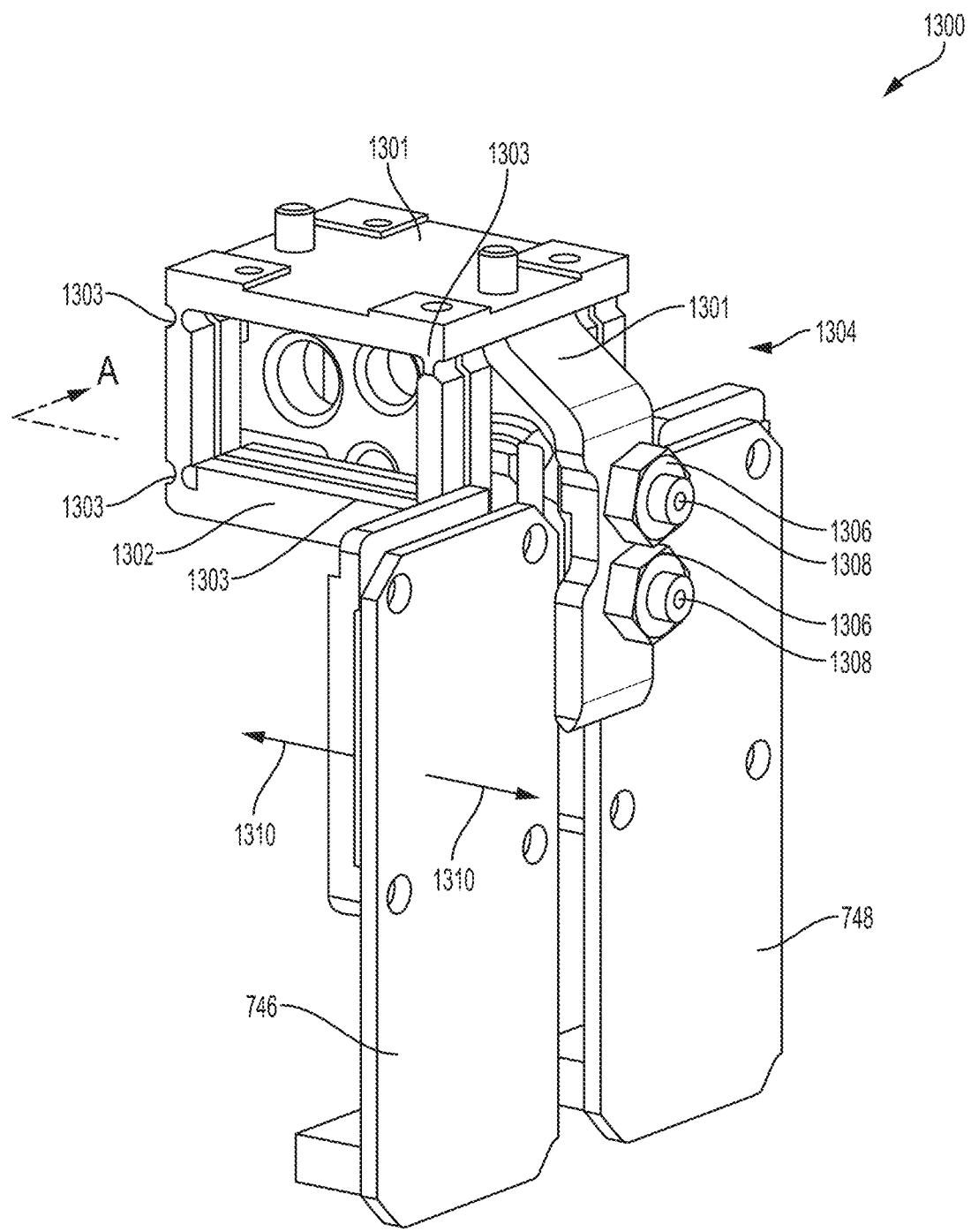
FIG. 13 shows a diagram of an example flexure of the example stereoscopic visualization camera of FIGS. 7 and 8, according to an example embodiment of the present disclosure.

FIG. 13 shows a diagram of an example dual flexure 1300, according to an example embodiment of the present disclosure. The flexure 1300 illustrated in FIG. 13 is for the optical image sensor 744 and is configured to independently move the right optical image sensor 746 and the left optical image sensor 748 along their respective optical axis for purposes of final focusing. The flexure 1300 includes a support beam 1301 for connection to the housing 302 of the example stereoscopic visualization camera 300 and to provide a rigid base for actuation. The flexure 1300 also includes a beam 1302 for each channel (e.g., sensor 746 and 748) that is rigid in all directions except for the direction of motion 1310. The beam 1302 is connected to flexing hinges 1303 that enable the beam 1302 to move in a direction of motion 1310, a parallelogram translation in this example.

An actuator device 1304 flexes the beam 1302 in the desired direction for a desired distance. The actuator device 1304 includes a push-screw 1306 and a pull screw 1308, for each channel, which apply opposite forces to the beam 1302 causing the flexing hinges 1303 to move. The beam 1302 may be moved inward, for example, by turning the push-screw 1306 to push on the beam 1302. The flexure 1300 illustrated in FIG. 13 is configured to independently move the right optical image sensor 746 and the left optical image sensor 748 axially along their optical axis.

After the beam 1302 is flexed into a desired position, a locking mechanism is engaged to prevent further movement, thereby creating a rigid column. The locking mechanism includes the push-screw 1306 and its respective concentric pull screw 1308, that when tightened, create large opposing forces that result in the rigid column of the beam 1302.

While the optical image sensors 746 and 748 are shown as being connected to the same flexure 1300, in other examples, the sensors may be connected to separate flexures. For example, returning to FIG. 8, the right optical image sensor 746 is connected to flexure 750 and the left optical image sensor 748 is connected to flexure 752. The use of the separate flexures 750 and 752 enables the optical image sensors 746 and 748 to be separately adjusted to, for example, align the left and right optical views and/or reduce or eliminate spurious parallax. Alternatively, the flexures may be omitted.

In addition, while FIG. 13 shows image sensors 746 and 748 connected to the flexure 1300, in other examples, the lenses of the front lens set 714, the zoom lens assembly 716, the lens barrel set 718, and/or the final optical element set 742 may be connected to alternative or additional flexures instead. In some instances, each of the right and left lenses of the front lens set 714, the zoom lens assembly 716, the lens barrel set 718, and/or the final optical element set 742 may be connected to a separate flexure 1300 to provide independent radial, rotational, and/or tilt adjustment.

The flexure 1300 may provide motion resolution of less than a micron. As a result of the very fine motion adjustment, images from the right and left optical paths may have an alignment accuracy of several or even one pixel for a 4K display monitor. Such accuracy is viewed on each display 512, 514 by overlaying the left and right views and observing both views with both eyes, rather than stereoscopically.

In some embodiments, the flexure 1300 can include the flexure disclosed in U.S. Pat. No. 5,359,474, titled "SYSTEM FOR THE SUB-MICRON POSITIONING OF A READ/WRITE TRANSDUCER," the entirety of which is incorporated herein by reference. In yet other embodiments, the lenses of the front lens set 714, the zoom lens assembly 716, the lens barrel set 718, and/or the final optical element set 742 may be stationary in a radial direction. Instead, a deflecting element (e.g., a mirror) with an adjustable deflection direction in an optical path may be used to steer the right and/or left optical paths to adjust alignment and/or spurious parallax. Additionally or alternatively, a tilt/shift lens may be provided in the optical path. For instance, a tilt of an optical axis may be controlled with an adjustable wedge lens. In further embodiments, lenses of the front lens set 714, the zoom lens assembly 716, the lens barrel set 718, and/or the final optical element set 742 may include dynamic lenses with parameters that can be changed electronically. For example, the lenses may include Varioptic liquid lenses produced by Invenios France SAS.

V. Example Processors of the Stereoscopic Visualization Camera

Figure 14:
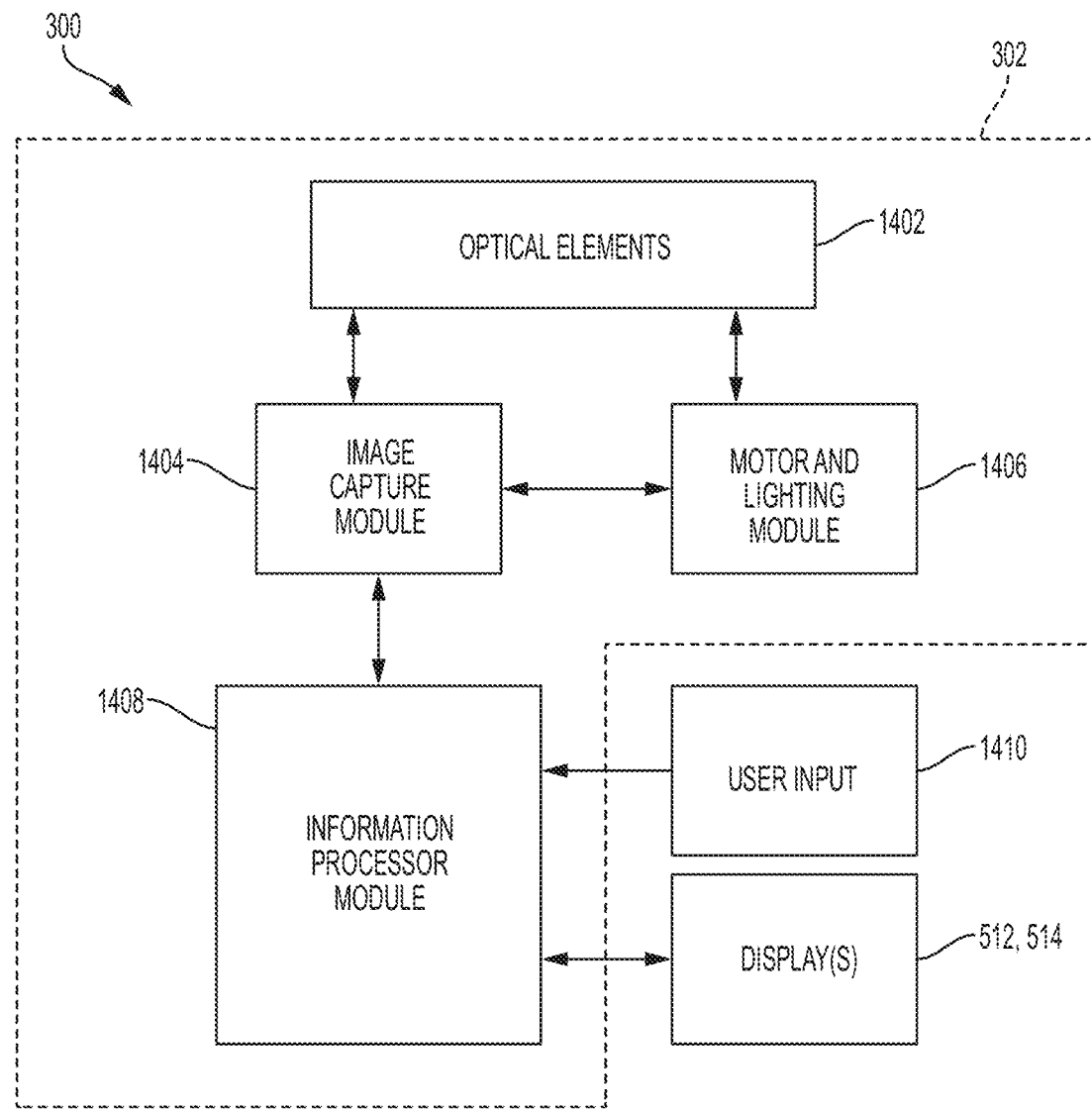
FIG. 14 shows a diagram of modules of the example stereoscopic visualization camera for acquiring and processing image data, according to an example embodiment of the present disclosure.

The example stereoscopic visualization camera 300 is configured to record image data from the right and left optical paths and output the image data to the monitor(s) 512 and/or 514 for display as a stereoscopic image. FIG. 14 shows a diagram of modules of the example stereoscopic visualization camera 300 for acquiring and processing image data, according to an example embodiment of the present disclosure. It should be appreciated that the modules are illustrative of operations, methods, algorithms, routines, and/or steps performed by certain hardware, controllers, processors, drivers, and/or interfaces. In other embodiments, the modules may be combined, further partitioned, and/or removed. Further, one or more of the modules (or portions of a module) may be provided external to the stereoscopic visualization camera 300 such as in a remote server, computer, and/or distributed computing environment.

In the illustrated embodiment of FIG. 14, the components 408, 702 to 750, and 1300 in FIGS. 7 to 13 are collectively referred to as optical elements 1402. The optical elements 1402 (specifically the optical image sensors 746 and 748) are communicatively coupled to an image capture module 1404 and a motor and lighting module 1406. The image capture module 1404 is communicatively coupled to an information processor module 1408, which may be communicatively coupled to an externally located user input device 1410 and one or more display monitors 512 and/or 514.

The example image capture module 1404 is configured to receive image data from the optical image sensors 746 and 748. In addition, the image capture module 1404 may define the pixel sets 1006 and 1008 within the respective pixel grids 1002 and 1004. The image capture module 1404 may also specify image recording properties, such as frame rate and exposure time.

The example motor and lighting module 1406 is configured to control one or more motors (or actuators) to change a radial, axial, and/or tilt position of one or more of the optical elements 1402. For instance, a motor or actuator may turn a drive screw to move the carrier 724 along the track 1106, as shown in FIGS. 11 and 12. A motor or actuator may also turn the push-screw 1306 and/or the pull screw 1308 of the flexure 1300 of FIG. 13 to adjust a radial, axial, or tilt position of a lens and/or optical image sensor. The motor and lighting module 1406 may also include drivers for controlling the light sources 708.

The example information processor module 1408 is configured to process image data for display. For instance, the information processor module 1408 may provide color correction to image data, filter defects from the image data, and/or render image data for stereoscopic display. The information processor module 1408 may also perform one or more calibration routines to calibrate the stereoscopic visualization camera 300 by providing instructions to the image capture module 1404 and/or the motor and lighting module 1406 to perform specified adjustments to the optical elements. The information processor module 1408 may further determine and provide in real-time instructions to the image capture module 1404 and/or the motor and lighting module 1406 to improve image alignment and/or reduce spurious parallax.

The example user input device 1410 may include a computer to provide instructions for changing operation of the stereoscopic visualization camera 300. The user input device 1410 may also include controls for selecting parameters and/or features of the stereoscopic visualization camera 300. In an embodiment, the user input device 1410 includes the control arms 304 of FIG. 3. The user input device 1410 may be hardwired to the information processor module 1408. Additionally or alternatively, the user input device 1410 is wirelessly or optically communicatively coupled to the information processor module 1408.

The example display monitors 512 and 514 include, for example, televisions and/or computer monitors configured to provide a three-dimensional viewing experience. For example, the display monitors may include the LG® 55LW5600 television. Alternatively, the display monitors 512 and 514 may include a laptop screen, tablet screen, a smartphone screen, smart-eyewear, a projector, a holographic display, etc.

The sections that follow describe the image capture module 1404, the motor and lighting module 1406, and the information processor module 1408 in more detail.

A. Example Image Capture Module

Figure 15:
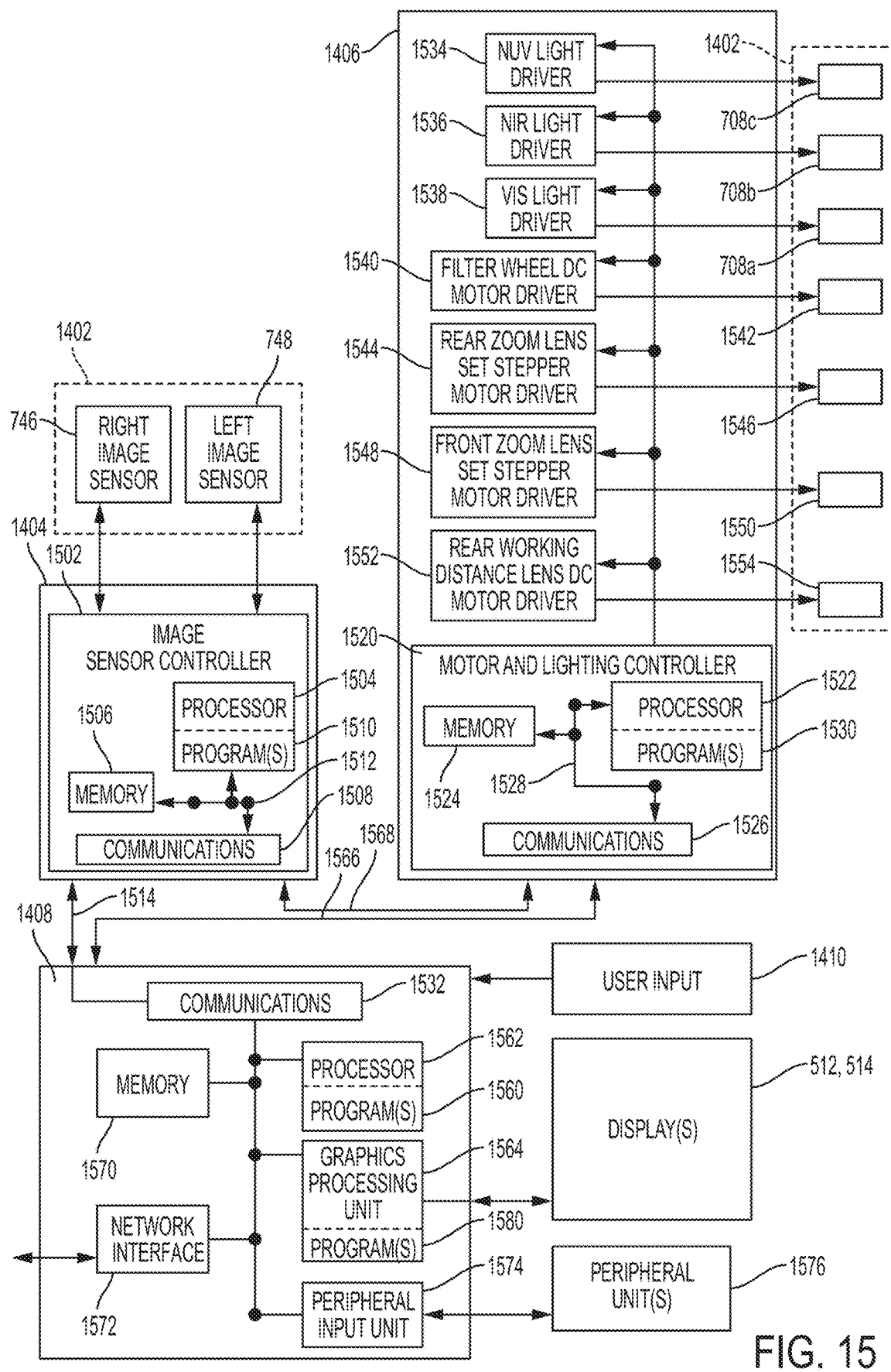
FIG. 15 shows a diagram of internal components of the modules of FIG. 14, according to an example embodiment of the present disclosure.

FIG. 15 shows a diagram of the image capture module 1404, according to an example embodiment of the present disclosure. The example image capture module 1404 includes an image sensor controller 1502, which includes a processor 1504, a memory 1506, and a communications interface 1508. The processor 1504, the memory 1506, and the communications interface 1508 may be communicatively coupled together via an image sensor controller bus 1512.

The processor 1504 is programmable with one or more programs 1510 that are persistently stored within the memory 1506. The programs 1510 include machine readable instructions, which when executed, cause the processor 1504 to perform one or more steps, routines, algorithms, etc. In some embodiments, the programs 1510 may be transmitted to the memory 1506 from the information processor module 1408 and/or from the user input device 1410. In other examples, the programs 1510 may be transmitted to the processor 1504 directly from the information processor module 1408 and/or from the user input device 1410.

The example image sensor controller 1502 is communicatively coupled to the right optical image sensor 746 and the left optical image sensor 748 of the optical elements 1402. The image sensor controller 1502 is configured to provide power to the optical image sensors 746 and 748 in addition to sending timing control data and/or programming data. In addition, the image sensor controller 1502 is configured to receive image and/or diagnostic data from the optical image sensors 746 and 748.

Each of the optical image sensors 746 and 748 contains programmable registers to control certain parameters and/or characteristics. One or more of the registers may specify a location of the pixel sets 1006 and 1008 within the respective pixel grids 1002 and 1004 of FIG. 10. The registers may store a value of a starting location with respect to an origin point or edge point of the pixel grids 1002 and 1004. The registers may also specify a width and height of the pixel sets 1006 and 1008 to define a rectangular region of interest. The image sensor controller 1502 is configured to read pixel data for pixels that are within the specified pixel sets 1006 and 1008. In some embodiments, the registers of the optical image sensors 746 and 748 may facilitate the designation of pixel sets of other shapes, such as circles, ovals, triangles, etc. Additionally or alternatively, the registers of the optical image sensors 746 and 748 may enable multiple pixel sets to be specified simultaneously for each of the pixel grids 1002 and 1004.

A light-sensing portion of the pixels of the pixel grids 1002 and 1004 is controlled by embedded circuitry, which specifies different modes of light-sensing. The modes include a reset mode, an integration mode, and a readout mode. During the reset mode, a charge storage component of a pixel is reset to a known voltage level. During the integration mode, the pixel is switched to an "on" state. Light that reaches a sensing area or element of the pixel causes a charge to accumulate in a charge storage component (e.g., a capacitor). The amount of stored electrical charge corresponds to the amount of light incident on the sensing element during the integration mode. During the readout mode, the amount of electrical charge is converted into a digital value and read out of the optical image sensors 746 and 748 via the embedded circuitry and transmitted to the image sensor controller 1502. To read every pixel, the charge storage component of each pixel in a given region is connected sequentially by switched internal circuitry to a readout circuit, which performs the conversion of the electrical charge from an analog value to digital data. In some embodiments, the pixel analog data is converted to 12-bit digital data. However, it should be appreciated that the resolution may be less or greater based on allowances for noise, settling time, frame rate, and data transmission speed. The digital pixel data of each pixel may be stored to a register.

The example processor 1504 of the image sensor controller 1502 of FIG. 15 is configured to receive pixel data (e.g., digital data indicative of an electrical charge stored in the pixel corresponding to an amount of incident light on an element of the pixel) from each of the pixels within the pixel sets 1006 and 1008. The processor 1504 forms a right image from the pixel data received from the right optical image sensor 746. In addition, the processor 1504 forms a left image from the pixel data received from the left optical image sensor 748. Alternatively, the processor 1504 forms only a portion (for example, one row or several rows) of each the left and right images before transmitting the data downstream. In some embodiments, the processor 1504 uses a register location to determine a location of each pixel within an image.

After the right and left images are created, the processor 1504 synchronizes the right and left images. The processor 1504 then transmits both of the right and left images to the communications interface 1508, which processes the images into a format for transmission to the information processor module 1408 via a communications channel 1514. In some embodiments, the communications channel 1514 conforms to the USB 2.0 or 3.0 standard and may comprise a copper or fiber optical cable. The communications channel 1514 may enable up to approximately 60 pairs (or more) of left and right images (having a stereoscopic resolution of 1920× 1080 and a data conversion resolution of 12-bits) per second to be transmitted per second. The use of a copper USB cable enables power to be provided from the information processor module 1408 to the image capture module 1404.

The sections below further describe features provided by the processor 1504 of the image sensor controller 1502 executing certain programs 1510 to acquire and/or process image data from the optical image sensors 746 and 748.

1. Exposure Example

The example processor 1504 may control or program an amount of time the optical image sensors 746 and 748 are in the integration mode, discussed above. The integration mode occurs for a time period referred to as an exposure time. The processor 1504 may set the exposure time by writing a value to an exposure register of the optical image sensors 746 and 748. Additionally or alternatively, the processor 1504 may transmit instructions to the optical image sensors 746 and 748 signaling the start and end of the exposure time. The exposure time may be programmable between a few milliseconds ("ms") to a few seconds. Preferably the exposure time is approximately the inverse of the frame rate.

In some embodiments, the processor 1504 may apply a rolling shutter method to the optical image sensors 746 and 748 to read pixel data. Under this method, the exposure time for a given row of pixels of the pixel sets 1006 and 1008 begins just after the pixels in that row have been read out and then reset. A short time later, the next row (which is typically physically most proximate to the row just set) is read, and accordingly reset with its exposure time restarted. The sequential reading of each pixel row continues until the last or bottom row of the pixel sets 1006 and 1008 have been read and reset. The processor 1504 then returns to the top row of the pixel sets 1006 and 1008 to read pixel data for the next image.

In another embodiment, the processor 1504 applies a global shutter method. Under this method, the processor 1504 implements readout and reset in a manner similar to the rolling shutter method. However, in this method integration occurs simultaneously for all pixels in the pixel sets 1006 and 1008. The global shutter method has the advantage of reducing defects in an image compared to the rolling shutter method since all of the pixels are exposed at the same time. In comparison, in the rolling shutter method, there is a small time delay between exposing the lines of the pixel set. Small defects can develop during the times between line exposures, especially between top lines and bottom lines where small changes at the target site 700 between reads can occur.

2. Dynamic Range Example

The example processor 1504 may execute one or more programs 1510 to detect light that is outside of a dynamic range of the optical image sensors 746 and 748. Generally, extremely bright light completely fills a charge storage region of a pixel, thereby resulting in lost image information regarding the exact brightness level. Similarly, extremely low light or lack of light fails to impart a meaningful charge in a pixel, which also results in lost image information. Images created from this pixel data accordingly do not accurately reflect the light intensity at target site 700.

To detect light that is outside the dynamic range, the processor 1504 may execute one of several high dynamic range ("HDR") programs 1510 including, for example, a multiple-exposure program, a multi-slope pixel integration program, and a multi-sensor image fusion program. In an example, the multiple-exposure program may utilize HDR features integrated or embedded with the optical image sensors 746 and 748. Under this method, the pixel sets 1006 and 1008 are placed into the integration mode for a normal expose time. The lines of the pixel sets 1006 and 1008 are read and stored in a memory at the optical image sensors 746 and 748 and/or the memory 1506 of the image sensor controller 1502. After the read is performed by the processor 1504, each line in the pixel sets 1006 and 1008 is turned on again for a second exposure time that is less than the normal exposure time. The processor 1504 reads each of the lines of pixels after the second exposure time and combines this pixel data with the pixel data from the normal exposure time for the same lines. The processor 1504 may apply tone-mapping to choose between (or combine) the pixel data from the normal-length and short-length exposure times and map the resulting pixel data to a range that is compatible with downstream processing and display. Using the multiple-exposure program, the processor 1504 is able to expand the dynamic range of the optical image sensors 746 and 748 and compress the resulting range of pixel data for display.

The processor 1510 may operate a similar program for relatively dark light. However, instead of the second exposure time being less than the normal time, the second exposure time is greater than the normal time, thereby providing the pixels more time to accumulate a charge. The processor 1510 may use tone-mapping to adjust the read pixel data to compensate for the longer exposure time.

3. Frame Rate Example

The example processor 1510 may control or specify a frame rate for the optical image sensors 746 and 748. In some embodiments, the optical image sensors 746 and 748 include on-board timing circuitry and programmable control registers to specify the number of times per second each of the pixels within the pixel sets 1006 and 1008 are to be cycled through the imaging modes discussed above. A frame or image is formed each time the pixel set progresses through the three modes. A frame rate is the number of times per second the pixels in the pixel sets 1006 and 1008 are integrated, read, and reset.

The processor 1510 may be synchronized with the optical image sensors 746 and 748 such that reads are conducted at the appropriate time. In other examples, the processor 1510 is asynchronous with the optical image sensors 746 and 748. In these other examples, the optical image sensors 746 and 748 may store pixel data after a local read to a temporary memory or queue. The pixel data may then be read periodically by the processor 1510 for right and left image synchronization.

The processing of frames or images in a time-sequential manner (e.g., creation of an image stream) provides an illusion of motion conveyed as a video. The example processor 1510 is configured to program a frame rate that provides the appearance of a smooth video to an observer. A frame rate that is too low makes any motion appear choppy or uneven. Movie quality above a maximum threshold frame rate is not discernable to an observer. The example processor 1510 is configured to generate approximately 20 to 70 frames per second, preferably between 50 and 60 frames per second for typical surgical visualization.

4. Sensor Synchronization Example

The example processor 1504 of FIG. 15 is configured to control the synchronization of the optical image sensors 746 and 748. The processor 1504 may, for instance, provide power simultaneously to the optical image sensors 746 and 748. The processor 1504 may then provide a clock signal to both of the optical image sensors 746 and 748. The clock signal enables the optical image sensors 746 and 748 to operate independently in a free-run mode but in a synchronized and/or simultaneous manner. Accordingly, the optical image sensors 746 and 748 record pixel data at nearly the same time. The example processor 1504 receives the pixel data from the optical image sensors 746 and 748, constructs at least a fraction of the images and/or frames and synchronizes the images and/or frames (or fraction thereof) to account for any slight timing mismatches. Typically, the lag between the optical image sensors 746 and 748 is less than 200 microseconds. In other embodiments, the processor 1504 may use a synchronization pin to simultaneously activate the optical image sensors 746 and 748 after, for example, each reset mode.

B. Example Motor and Lighting Module

The example stereoscopic visualization camera 300 of FIG. 15 includes the motor and lighting module 1406 to control one or more motors or actuators for moving lenses of the optical elements 1402 and/or controlling lighting output from the light sources 708. The example motor and lighting module 1406 includes a motor and lighting controller 1520 that contains a processor 1522, a memory 1524, and a communications interface 1526 that are communicatively coupled together via communication bus 1528. The memory 1524 stores one or more programs 1530 that are executable on the processor 1522 to perform control, adjustment, and/or calibration of the lenses of the optical elements 1402 and/or the light sources 708. In some embodiments, the programs 1530 may be transmitted to the memory 1524 from the information processor module 1408 and/or the user input device 1410.

The communications interface 1526 is communicatively coupled to the communications interface 1508 of the image capture module 1404 and a communications interface 1532 of the information processor module 1408. The communications interface 1526 is configured to receive command messages, timing signals, status messages, etc. from the image capture module 1404 and the information processor module 1408. For example, the processor 1504 of the image capture module 1404 may send timing signals to the processor 1522 to synchronize timing between lighting control and exposure time of the optical image sensors 746 and 748. In another example, the information processing module 1408 may send command messages instructing certain light sources 708 to be activated and/or certain lenses of the optical elements 1402 to be moved. The commands may be in response to input received from an operator via, for example, the user input device 1410. Additionally or alternatively, the commands may be in response to a calibration routine and/or real-time adjustment to reduce or eliminate image misalignment and/or defects such as spurious parallax.

The example motor and lighting module 1406 includes drivers that provide power to control motors for adjusting an axial and/or radial position of the lenses of the optical elements 1402 and/or the light output from the light sources 708. Specifically, the motor and lighting module 1406 includes a NUV light driver 1534 to transmit a NUV signal to the NUV light source 708c, a NIR light driver 1536 to transmit a NIR signal to the NIR light source 708b, and a visible light driver 1538 to transmit a visible light signal to the visible light source 708a.

In addition, the motor and lighting module 1406 includes a filter motor driver 1540 to transmit a filter motor signal to a filter motor 1542, which controls the filter 740 of FIGS. 7 and 8. The motor and lighting module 1406 includes a rear zoom lens motor driver 1544 to transmit a rear zoom lens motor signal to a rear zoom lens motor 1546, a front zoom lens motor driver 1548 to transmit a front zoom lens motor signal to a front zoom lens motor 1550, and a rear working distance lens motor driver 1552 to transmit a working distance lens motor signal to a working distance lens motor 1554. The motor and lighting module 1406 may also include a motor and/or actuator to move and/or tilt the deflecting element 712.

The rear zoom lens motor 1546 is configured to rotate a drive screw that causes carrier 730 to move axially along a track or rail. The front zoom lens motor 1550 is configured to rotate a drive screw that causes carrier 724 to move axially along the track 1106 shown in FIGS. 11 and 12. The working distance lens motor 1554 is configured to rotate a drive screw that causes the rear working distance lens 702 to move axially along a track or rail.

The drivers 1536, 1538, and 1540 may include any type of lighting driver, transformer, and/or ballast. The drivers 1536, 1538, and 1540 are configured to output a pulse width modulation ("PWM") signal to control an intensity of light output by the light sources 708. In some embodiments, the processor 1522 may control the timing of the drivers 1536, 1538, and 1540 to correspond to a timing for applying a certain filter using the filter motor driver 1540.

The example drivers 1540, 1544, 1548, and 1552 may include, for example stepper motor drivers and/or DC motor drivers. Likewise, the motors 1542, 1546, 1550, and/or 1554 may include a stepper motor, a DC motor, or other electrical, magnetic, thermal, hydraulic, or pneumatic actuator. The motors 1542, 1546, 1550, and/or 1554 may include, for example, a rotary encoder, a slotted optical switch (e.g., a photointerrupter), and/or a linear encoder to report an angular position of a shaft and/or axle for feedback reporting and control. Alternative embodiments may include voice-coil motors, piezoelectric motors, linear motors, with suitable drivers, and equivalents thereof.

To control the drivers 1534, 1536, 1538, 1540, 1544, 1548, and 1552, the processor 1522 is configured to use a program 1530 for converting a command message into a digital and/or analog signal. The processor 1522 transmits the digital and/or analog signal to the appropriate driver, which outputs an analog power signal, such as a PWM signal corresponding to the received signal. The analog power signal provides power to an appropriate motor or actuator causing it to rotate (or otherwise move) by a desired amount.

The processor 1522 may receive feedback from the drivers 1534, 1536, 1538, 1540, 1544, 1548, and 1552, the motors 1542, 1546, 1550, and/or 1554, and/or the light sources 708. The feedback corresponds to, for example, a lighting level or lighting output. Regarding the motors, the feedback corresponds to a position of a motor (or other actuator) and/or an amount of movement. The processor 1522 uses a program 1530 to translate the received signal into digital feedback to determine, for example, a radial, tilt, and/or axial position of a lens based on an angular position of the corresponding motor or actuator shaft. The processor 1522 may then transmit a message with the position information to the information processor module 1408 for display to a user and/or to track a position of the lenses of the optical elements 1402 for calibration.

In some embodiments, the motor and lighting module 1406 may include additional drivers to change an axial, tilt, and/or radial position of individual lenses within the optical elements 1402. For example, the motor and lighting module 1406 may include drivers that control motors for actuating flexures 750 and 752 for the optical image sensors 746 and 748 for tilting and/or radial/axial adjustment. Further, the motor and lighting module 1406 may include drivers that control motors (or actuators) for individually tilting and/or adjusting front lenses 720 and 722, the front zoom lenses 726 and 728, the rear zoom lenses 732 and 734, the lens barrels 736 and 738, and/or final optical elements 745 and 747 radially along an x-axis or y-axis and/or axially. Independent adjustment of the lenses and/or sensors enables, for example, the motor and lighting controller 1520 to remove image defects and/or align the left and right images.

The following sections describe how the processor 1552 executes one or more programs 1530 to change a working distance, zoom, filter position, lens position, and/or light output.

1. Working Distance Example

The example processor 1522 of the motor and lighting module 1406 of FIG. 15 is configured to adjust a working distance of the stereoscopic visualization camera 300. The working distance is set by adjusting a distance between the rear working distance lens 704 and the front working distance lens 408. The processor 1522 adjusts the distance by causing the rear working distance lens 704 to move relative to the front working distance lens 408. Specifically, the processor 1522 sends a signal to the rear working distance lens motor driver 1552, which activates the working distance lens motor 1554 for a predetermined time proportional to an amount the rear working distance lens 704 is to be moved. The working distance lens motor 1554 drives a leadscrew through threads attached to a sliding track that holds the rear working distance lens 704. The working distance lens motor 1554 causes the lens 704 to move a desired distance, thereby adjusting the working distance. The working distance lens motor 1554 may provide a feedback signal to the processor 1522, which determines if the rear working distance lens 704 was moved the desired amount. If the movement is less or more than desired, the processor 1522 may send instructions further refining the position of the rear working distance lens 704. In some embodiments, the information processor module 1408 may determine feedback control for the rear working distance lens 704.

To determine a position of the rear working distance lens 704, the processor 1522 may operate one or more calibration programs 1530. For example, upon activation, the processor 1522 may instruct the working distance lens motor 1554 to drive a leadscrew to move the rear working distance lens 704 along a track or rail until triggering a limit switch at one end of the motion range. The processor 1522 may designate this stop position as a zero-point for the encoder of the motor 1554. Having knowledge of the current position of the rear working distance lens 704 and the corresponding encoder value, the processor 1522 becomes capable of determining a number of shaft rotations to cause the rear working distance lens 704 to move to a desired position. The number of shaft rotations is transmitted in an analog signal to the working distance lens motor 1554 (via the driver 1552) to accordingly move the lens 704 to a specified position.

2. Zoom Example

The example processor 1522 of FIG. 15 is configured to execute one or more programs 1530 to change a zoom level of the stereoscopic visualization camera 300. As discussed above, zoom (e.g., magnification change) is achieved by changing positions of the front zoom set 724 and the rear zoom set 730 relative to each other and relative to the front lens set 714 and the lens barrel set 718. Similar to the calibration procedure described above for the rear working distance lens 704, the processor 1522 may calibrate positions of the sets 724 and 730 along tracks or rails. Specially, the processor 1522 sends instructions causing the rear zoom lens motor 1546 and the front zoom lens motor 1550 to move the sets 724 and 730 (e.g., carriers) along a rail (or rails) to a stop position at a limit switch. The processor 1522 receives encoder feedback from the motors 1546 and 1550 to determine an encoder value associated with the stop position for the sets 724 and 730. The processor 1522 may then zero-out the encoder value or use the known encoder value at the stop position to determine how much the motors 1546 and 1550 are to be activated to achieve a desired position for the sets 724 and 730 along the rail.

In addition to calibration for stop position, the processor 1522 may execute programs 1530 that define locations for sets 724 and 730 to achieve a desired zoom level. For example, a known pattern of distance settings versus a set of desired zoom values may be stored as a program 1530 (or a look-up table) during a calibration procedure. The calibration procedure may include placing a template within the target site 700 and instructing the processor 522 to move the sets 724 and 730 until a certain designated marker or character is a certain size in right and left images or frames. For example, a calibration routine may determine positions of the set 724 and 730 on a rail corresponding to when character "E" on a template at the target site 700 is displayed in right and left images as having a height of 10 pixels.

In some embodiments, the information processor module 1408 may perform the visual analysis and send instructions to the processor 1522 regarding desired movement for the sets 724 and 730 to zoom in or zoom out. In addition, the information processor 1408 may send instructions for moving the focal plane such that the target site 700 at the desired zoom level is in focus. The instructions may include, for example, instructions to move the rear working distance lens 704 and/or moving the sets 724 and 730 together and/or individually. In some alternative embodiments, the processor 1522 may receive calibration parameters for the rail position of the front zoom set 724 and the rear zoom set 730 at certain zoom levels from the user input device 1410 or another computer.

The example processor 1522 and/or the information processor module 1408 may send instructions such that an image remains in focus while magnification changes. The processor 1522, for example, may use a program 1530 and/or a look-up-table to determine how certain lenses are to be moved along an optical axis to retain focus on the target site 700. The programs 1530 and/or look-up-table may specify magnification levels and/or set points on a rail and corresponding lens adjustments needed to keep the focal plane from moving.

Table 2 below shows an example program 1530 or look-up-table that may be used by the processor 1522 to retain focus while changing magnification. The position of the front zoom lens set 724 and the rear zoom lens set 730 is normalized based on a length of a rail to stop positions for the respective sets 724 and 730. To decrease magnification, the rear zoom lens set is moved toward the lens barrel set 718, thereby increasing a position along a rail. The front zoom lens set 724 is also moved. However, its movement does not necessarily equal the movement of the rear zoom lens set 730. Instead, the movement of the front zoom lens set 724 accounts for changing a distance between the sets 724 and 730 to retain the position of the focal plane to maintain focus while changing magnifications. For example, to decrease a magnification level from 10× to 9×, the processor 1522 instructs the rear zoom lens set 730 to move from position 10 to position 11 along a rail. In addition, the processor 1522 instructs the front zoom lens set 724 to move from position 5 to position 4 along a rail (or same rail as the set 730). Not only have the sets 724 and 730 moved to change magnification, the sets 724 and 730 have moved relative to each other to retain focus.

TABLE 2

| Magnification | Front Zoom Lens Set Position | Rear Zoom Lens Set Position |
|---|---|---|
| 10X | 5 | 10 |
| 9X | 4 | 11 |
| 8X | 3 | 12 |
| 7X | 4.5 | 14 |
| 6X | 6 | 17 |
| 5X | 8 | 20 |

It should be appreciated that Table 2 provides an example of how the sets 724 and 730 may be moved. In other examples, Table 2 may include additional rows to account for more precise magnifications and/or positions of the sets 724 and 730. Additionally or alternatively, Table 2 may include a column for the rear working distance lens 704. For example, the rear working distance lens 704 may be moved instead of or in conjunction with the front zoom lens set 724 to retain focus. Further, Table 2 may include rows specifying positions for the sets 724 and 730 and the rear working distance lens 704 to retain focus during changes in working distance.

The values in Table 2 may be determined through calibration and/or received from a remote computer or the user input device 1410. During calibration, the information processor module 1408 may operate a calibration program 1560 that progresses through different magnifications and/or working distances. A processor 1562 at the information processor module 1408 may perform image processing of the images themselves or received pixel data to determine when a desired magnification is achieved using, for example, a template with predetermined shapes and/or characters. The processor 1562 determines if the received images are in-focus. Responsive to determining images are out of focus, the processor 1562 sends instructions to the processor 1522 to adjust the front zoom lens set 724 and/or the rear working distance lens set 704. The adjustment may include iterative movements in forward and reverse directions along an optical path until the processor 1562 determines images are in focus. To determine an image is in focus, the processor 1562 may perform, for example, image analysis searching for images where light fuzziness is minimal and/or analyzing pixel data for differences in light values between adjacent pixel regions (where greater differences correspond to more in focus images). After determining an image is in focus at a desired working distance and magnification, the processor 1562 and/or the processor 1522 may then record positions of the sets 724 and 730 and/or the rear working distance lens 704 and corresponding magnification level.

3. Filter Position Example

The example processor 1522 of the motor and lighting module 1406 of FIG. 15 is configured to move the filter 740 into the right and left optical paths based on received instructions. In some examples, the filter 740 may include a mirror array. In these examples, the processor 1522 sends instructions to the filter motor driver 1540 to actuate one or more motors 1542 to change positions of the mirrors. In some instances, the driver 1540 may send an electrical charge along one or more paths to the filter 740, causing certain mirror elements to switch to an on or off position. In these examples, the filter type selection is generally binary based on which mirrors to actuate.

In other examples, the filter 740 may include a wheel, turret, or ring with different types of filters such as an infrared cut filter, near-infrared bandpass filter, and near-ultraviolet cut filter. In these examples, the wheel is rotated by the filter motor 1542. The processor 1522 determines stop positions of the wheel corresponding to partitions between the different filters. The processor 1522 also determines rotary encoder value corresponding to each of the stop positions.

The processor 1522 may operate a calibration program 1530 and/or the processor 1562 may operate a calibration program 1560 to determine the stop positions. For example, the processor 1522 may rotate the filter 740 slowly, with the processor 1562 determining when light received at the pixels changes (using either image analysis or reading pixel data from the image capture module 1404). A change in a light value at the pixels is indicative of a change in the filter type being applied to the optical paths). In some instances, the processor 1522 may change which light sources 708 are activated to create further distinction at the pixels when a different filter type is applied.

4. Light Control and Filter Example

As disclosed above, the processor 1522 may control the light sources 708 in conjunction with the filter 740 to cause light of a desired wavelength to reach the optical image sensors 746 and 748. In some examples, the processor 1522 may control or synchronize timing between activation of one or more of the light sources 708 and one or more of the filters 740. To synchronize timing, a program 1530 may specify a delay time for activating a certain filter. The processor 1522 uses this program 1530 to determine when, for example a signal to activate the filter 740 is to be transmitted relative to sending a signal to turn on a light source 708. The scheduled timing ensures the appropriate filter 740 is applied when the specified light source 708 is activated. Such a configuration enables features highlighted by one light source 708 (such as fluorescence) to be shown on top of or in conjunction with features displayed under a second light source 708, such as white or ambient light.

In some instances, the light sources 708 may be switched as fast as the light filters 740 may be changed, thereby enabling images recorded in different lights to be shown in conjunction on top of each other. For example, veins or other anatomical structures that emit fluorescence (due to an administered dye or contrast agent) may be shown on top of an image under ambient lighting. In this example, the veins would be highlighted relative to the background anatomical features shown in visible light. In this instance, the processor 1562 and/or a graphics processing unit 1564 (e.g., a video card or graphics card) of the information processor module 1408 combines or overlays one or more images recorded during application of one filter with images recorded during application of a subsequent filter.

In some embodiments, the processor 1522 may activate multiple light sources 708 at the same time. The light sources 708 can be activated simultaneously or sequentially to "interleave" light of different wavelengths to enable different information to be extracted using appropriate pixels at the optical image sensors 746 and 748. Activating the light sources simultaneously may help illuminate dark fields. For example, some applications use UV light to stimulate fluorescence at a target site 700. However, UV light is perceived by an operator as being very dark. Accordingly, the processor 1522 may activate the visible light source 1538 periodically to add some visible light to the viewing field so that the surgeon can observe the field-of-view without overwhelming pixels that are sensitive to UV light but can also detect some visible light. In another example, alternating between light sources 708 avoids, in some instances, washing out pixels of the optical image sensors 746 and 748 that have overlapping sensitivity at the edges of their ranges.

5. Light Intensity Control

The example processor 1522 of FIG. 15 is configured to execute one or more programs 1530 to change an intensity of or a level of illumination provided by the light sources 708. It should be appreciated that the depth of field is dependent on the level of illumination at the target site 700. Generally, higher illumination provides a greater depth of field. The processor 1522 is configured to ensure an appropriate amount of illumination is provided for a desired depth of field without washing out or overheating the field-of-view.

The visible light source 708a is driven by the visible light driver 1538 and outputs light in the human-visible part of the spectrum as well as some light outside that region. The NIR light source 708b is driven by the NIR light driver 1536 and outputs light primarily at a wavelength that referred to as near-infrared. The NUV light source 708c is driven by the NUV light driver 1534 and outputs light primarily at a wavelength that is deep in the blue part of the visible spectrum, which is referred to as near-ultraviolet. The respective light drivers 1534, 1536, and 1538 are controlled by commands provided by the processor 1522. Control of the respective output spectra of the light sources 708 is achieved by PWM signal, where a control voltage or current is switched between a minimum (e.g., off) and maximum (e.g., on) value. The brightness of the light that is output from the light sources 708 is controlled by varying the switching rate as well as the percentage of time the voltage or current is at the maximum level per cycle in the PWM signal.

In some examples, the processor 1522 controls an output of the light sources 708 based on a size of the field-of-view or zoom level. The processor 1522 may execute a program 1530 that specifies for certain light sensitive settings that light intensity becomes a function of zoom. The program 1530 may include, for example a look-up-table that correlates a zoom level to a light intensity value. The processor 1522 uses the program 1530 to select the PWM signal for the light source 708 based on the selected magnification level. In some examples, the processor 1522 may reduce light intensity as the magnification increases to maintain the amount of light provided to the field-of-view per unit of area.

C. Example Information Processor Module

The example information processor module 1408 within the stereoscopic visualization camera 300 of FIG. 15 is configured to analyze and process images/frames received from the image capture module 1404 for display. In addition, the information processor module 1408 is configured to interface with different devices and translate control instructions into messages for the image capture module 1404 and/or the motor and lighting module 1406. The information processor module 1408 may also provide an interface for manual calibration and/or manage automatic calibration of the optical elements 1402.

As shown in FIG. 15, the information processor module 1408 is communicatively and/or electrically coupled to the image capture module 1404 and the motor and lighting module 1406. For example, the communications channel 1514 in addition to communications channels 1566 and 1568 may include USB 2.0 or USB 3.0 connections. As such, the information processor module 1408 regulates and provides power to the modules 1404 and 1406. In some embodiments, the information processor module 1408 converts 110-volt alternating current ("AC") power from a wall outlet into a 5, 10, 12, and/or 24 volt direct current ("DC") supply for the modules 1404 and 1406. Additionally or alternatively, the information processor module 1408 receives electrical power from a battery internal to the housing 302 of the stereoscopic visualization camera 300 and/or a battery at the cart 510.

The example information processor module 1408 includes the communications interface 1532 to communicate bidirectionally with the image capture module 1404 and the motor and lighting module 1406. The information processor module 1408 also includes the processor 1562 configured to execute one or more programs 1560 to process images/frames received from the image capture module 1404. The programs 1560 may be stored in a memory 1570. In addition the processor 1562 may perform calibration of the optical elements 1402 and/or adjust the optical elements 1402 to align right and left images and/or remove visual defects.

Figure 16:
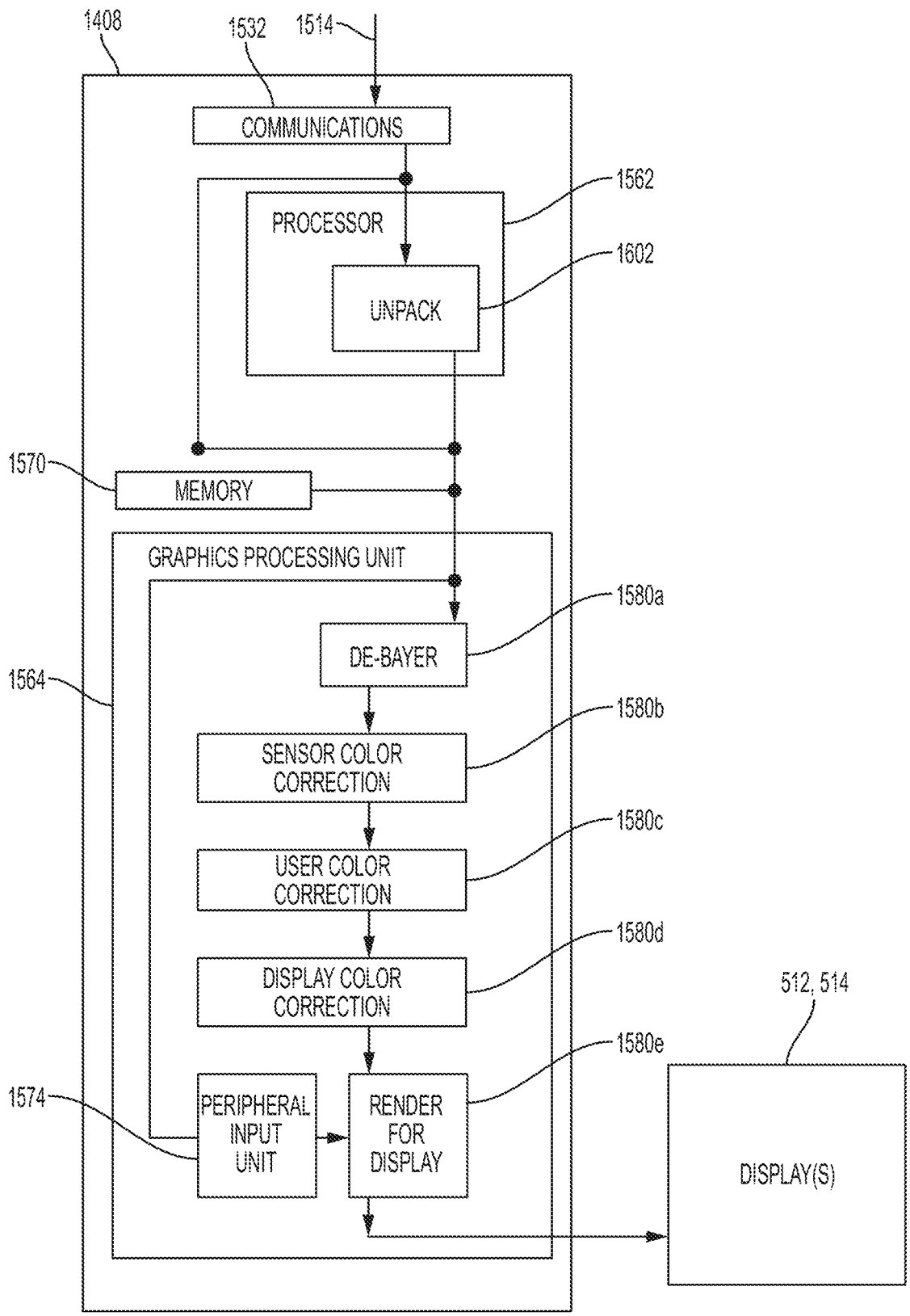
FIG. 16 shows a diagram of an information processor module of FIGS. 14 and 15, according to an example embodiment of the present disclosure.

To process images and/or frames into a rendered three-dimensional stereoscopic display, the example information processor module 1408 includes the graphics processing unit 1564. FIG. 16 shows a diagram of the graphics processing unit 1564, according to an example embodiment of the present disclosure. During operation, the processor 1562 receives images and/or frames from the image capture module 1404. An unpack routine 1602 converts or otherwise changes the images/frames from a format conducive for transmission across the communications channel 1514 into a format conducive for image processing. For instance, the images and/or frames may be transmitted across the communications channel 1514 in multiple messages. The example unpack routine 1602 combines the data from the multiple messages to reassemble the frames/images. In some embodiments, the unpack routine 1602 may queue frames and/or images until requested by the graphics processing unit 1564. In other examples, the processor 1562 may transmit each right and left image/frame pair after being completely received and unpacked.

The example graphics processing unit 1564 uses one or more programs 1580 (shown in FIG. 15) to prepare images for rendering. Examples of the programs 1580 are shown in FIGS. 15 and 16. The programs 1580 may be executed by a processor of the graphics processing unit 1564. Alternatively, each of the programs 1580 shown in FIG. 16 may be executed by a separate graphics processor, microcontroller, and/or application specific integrated circuit ("ASIC"). For example, a de-Bayer program 1580a is configured to smooth or average pixel values across neighboring pixels to compensate for a Bayer pattern applied to the pixel grids 1002 and 1004 of the right and left optical image sensors 746 and 748 of FIGS. 7 and 8. The graphics processing unit 1564 may also include programs 1580b, 1580c, and 1580d for color correction and/or white balance adjustment. The graphics processing unit 1564 also includes a renderer program 1580e for preparing color corrected images/frames for display on the display monitors 512 and 514. The graphics processing unit 1564 may further interact and/or include a peripheral input unit interface 1574, which is configured to combine, fuse, or otherwise include other images and/or graphics for presentation with the stereoscopic display of the target site 700. Further details of the programs 1580 and the information processor module 1408 more generally are discussed below.

The example information processor module 1408 may execute one or more programs 1562 to check for and improve latency of the stereoscopic visualization camera 300. Latency refers to the amount of time taken for an event to occur at the target site 700 and for that same event to be shown by the display monitors 512 and 514. Low latency provides a feeling that the stereoscopic visualization camera 300 is an extension of a surgeon's eyes while high latency tends to distract from the microsurgical procedure. The example processor 1562 may track how much time elapses between images being read from the optical image sensors 746 and 748 until the combined stereoscopic image based on the read images is transmitted for display. Detections of high latency may cause the processor 1562 to reduce queue times, increase the frame rate, and/or skip some color correction steps.

1. User Input Example

The example processor 1562 of the information processor module 1408 of FIG. 15 is configured to convert user input instructions into messages for the motor and lighting module 1406 and/or the image capture module 1402. User input instructions may include requests to change optical aspects of the stereoscopic visualization camera 300 including a magnification level, a working distance, a height of a focal plane (e.g., focus), a lighting source 708, and/or a filter type of the filter 740. The user input instructions may also include requests to perform calibration, including indications of an image being in focus and/or indications of image alignment, and/or indications of aligned ZRPs between left and right images. The user input instructions may further include adjustments to parameters of the stereoscopic visualization camera 300, such as frame rate, exposure time, color correction, image resolution, etc.

The user input instructions may be received from a user input device 1410, which may include the controls 305 of the control arm 304 of FIG. 3 and/or a remote control. The user input device 1410 may also include a computer, tablet computer, etc. In some embodiments, the instructions are received via a network interface 1572 and/or a peripheral input unit interface 1574. In other embodiments, the instructions may be received from a wired connection and/or a RF interface.

The example processor 1562 includes programs 1560 for determining an instruction type and determining how the user input is to be processed. In an example, a user may press a button of the control 305 to change a magnification level. The button may continue to be pressed until the operator has caused the stereoscopic visualization camera 300 to reach a desired magnification level. In these examples, the user input instructions include information indicative that a magnification level is to be, for example, increased. For each instruction received (or each time period in which a signal indicative of the instruction is received), the processor 1562 sends a control instruction to the motor and lighting processor 1406 indicative of the change in magnification. The processor 1522 determines from a program 1530 how much the zoom lens sets 724 and 730 are to be moved using, for example, Table 2. The processor 1522 accordingly transmits a signal or message to the rear zoom lens motor driver 1544 and/or the front zoom lens motor driver 1548 causing the rear zoom lens motor 1546 and/or the front zoom lens motor 1550 to move the rear zoom lens set 730 and/or the front zoom lens set 724 by an amount specified by the processor 1562 to achieve the desired magnification level.

It should be appreciated that in the above example, the stereoscopic visualization camera 300 provides a change based on user input but also makes automatic adjustments to maintain focus and/or a high image quality. For instance, instead of simply changing the magnification level, the processor 1522 determines how the zoom lens sets 724 and 730 are to be moved to also retain focus, thereby saving an operator from having to perform this task manually. In addition, the processor 1562 may, in real-time, adjust and/or align ZRPs within the right and left images as a magnification level changes. This may be done, for example, by selecting or changing locations of the pixel sets 1006 and 1008 with respect to pixel grids 1002 and 1004 of FIG. 10.

In another example, the processor 1562 may receive an instruction from the user input device 1410 to change a frame rate. The processor 1562 transmits a message to the processor 1504 of the image capture module 1404. In turn, the processor 1504 writes to registers of the right and left image sensors 746 and 748 indicative of the new frame rate. The processor 1504 may also update internal registers with the new frame rate to change a pace at which the pixels are read.

In yet another example, the processor 1562 may receive an instruction from the user input device 1410 to begin a calibration routine for ZRP. In response, the processor 1562 may execute a program 1560 that specifies how the calibration is to be operated. The program 1560 may include, for example, a progression or iteration of magnification levels and/or working distances in addition to a routine for verifying image quality. The routine may specify that for each magnification level, focus is to be verified in addition to ZRP. The routine may also specify how the zoom lens sets 724 and 730 and/or the rear working distance lens 704 are to be adjusted to achieve an in focus image. The routine may further specify how ZRP of the right and left images are to be centered for the magnification level. The program 1560 may store (to a look-up-table) locations of zoom lens sets 724 and/or the 730 and/or the rear working distance lens 704 in addition to locations of pixel sets 1006 and 1008 and the corresponding magnification level once image quality has been verified. Thus, when the same magnification level is requested at a subsequent time, the processor 1562 uses the look-up-table to specify positions for the zoom lens sets 724 and/or the 730 and/or the rear working distance lens 704 to the motor and lighting module 1406 and positions for the pixel sets 1006 and 1008 to the image capture module 1404. It should be appreciated that in some calibration routines, at least some of the lenses of the optical elements 1402 may be adjusted radially/rotationally and/or tilted to center ZRPs and/or align right and left images.

2. Interface Example

To facilitate communications between the stereoscopic visualization camera 300 and external devices, the example information processor module 1408 includes the network interface 1572 and the peripheral input unit interface 1574. The example network interface 1572 is configured to enable remote devices to communicatively couple to the information processor module 1408 to, for example, store recorded video, control a working distance, zoom level, focus, calibration, or other features of the stereoscopic visualization camera 300. In some embodiments, the remote devices may provide values or parameters for calibration look-up-tables or more generally, programs 1530 with calibrated parameters. The network interface 1572 may include an Ethernet interface, a local area network interface, and/or a Wi-Fi interface.

The example peripheral input unit interface 1574 is configured to communicatively couple to one or more peripheral devices 1576 and facilitate the integration of stereoscopic image data with peripheral data, such as patient physiological data. The peripheral input unit interface 1574 may include a Bluetooth® interface, a USB interface, an HDMI interface, SDI, etc. In some embodiments, the peripheral input unit interface 1574 may be combined with the network interface 1572.

The peripheral devices 1576 may include, for example, data or video storage units, patient physiological sensors, medical imaging devices, infusion pumps, dialysis machines, and/or tablet computers, etc. The peripheral data may include image data from a dedicated two-dimensional infrared-specialized camera, diagnostic images from a user's laptop computer, and/or images or patient diagnostic text from an ophthalmic device such as the Alcon Constellation® system and the WaveTec Optiwave Refractive Analysis (ORA™) system.

The example peripheral input unit interface 1574 is configured to convert and/or format data from the peripheral devices 1576 into an appropriate digital form for use with stereoscopic images. Once in digital form, the graphics processing unit 1564 integrates the peripheral data with other system data and/or the stereoscopic images/frames. The data is rendered with the stereoscopic images for display on the display monitors 512 and/or 514.

To configure the inclusion of peripheral data with the stereoscopic images, the processor 1562 may control an integration setup. In an example, the processor 1562 may cause the graphics processing unit 1564 to display a configuration panel on the display monitors 512 and/or 514. The configuration panel may enable an operator to connect a peripheral device 1576 to the interface 1574 and the processor 1562 to subsequently establish communications with the device 1576. The processor 1564 may then read which data is available or enable the operator to use the configuration panel to select a data directory location. Peripheral data in the directory location is displayed in the configuration panel. The configuration panel may also provide the operator an option to overlay the peripheral data with stereoscopic image data or display as a separate picture.

Selection of peripheral data (and overlay format) causes the processor 1562 to read and transmit the data to the graphics processing unit 1564. The graphics processing unit 1564 applies the peripheral data to the stereoscopic image data for presentation as an overlay graphic (such as fusing a preoperative image or graphic with a real-time stereoscopic image), a "picture-in-picture," and/or a sub-window to the side or on top of the main stereoscopic image window.

3. De-Bayer Program Example

The example de-Bayer program 1580a of FIG. 16 is configured to produce images and/or frames with values for red, green, and blue color at every pixel value. As discussed above, the pixels of the right and left optical image sensors 746 and 748 have a filter that passes light in the red wavelength range, the blue wavelength range, or the green wavelength range. Thus, each pixel only contains a portion of the light data. Accordingly, each image and/or frame received in the information processor module 1408 from the image capture module 1404 has pixels that contain either red, blue, or green pixel data.

The example de-Bayer program 1580a is configured to average the red, blue, and green pixel data of adjacent and/or neighboring pixels to determine more complete color data for each pixel. In an example, a pixel with red data and a pixel with blue data are located between two pixels with green data. The green pixel data for the two pixels is averaged and assigned to the pixel with red data and the pixel with blue data. In some instances, the averaged green data may be weighted based on a distance of the pixel with red data and the pixel with blue data from the respective green pixels. After the calculation, the pixels with originally only red or blue data now include green data. Thus, after the de-Bayer program 1580a is executed by the graphics processing unit 1564, each pixel contains pixel data for an amount of red, blue, and green light. The pixel data for the different colors is blended to determine a resulting color on the color spectrum, which may be used by the renderer program 1580e for display and/or the display monitors 512 and 514. In some examples, the de-Bayer program 1580a may determine the resulting color and store data or an identifier indicative of the color.

4. Color Correction Example

The example color correction programs 1580b, 1580c, and 1580d are configured to adjust pixel color data. The sensor color correction program 1580b is configured to account or adjust for variability in color sensing of the optical image sensors 746 and 748. The user color correction program 1580c is configured to adjust pixel color data based on perceptions and feedback of an operator. Further, the display color correction program 1580d is configured to adjust pixel color data based on a display monitor type.

To correct color for sensor variability, the example color correction program 1580b specifies a calibration routine that is executable by the graphics processing unit 1564 and/or the processor 1562. The sensor calibration includes placing a calibrated color chart, such as the ColorChecker® Digital SG by X-Rite, Inc. at the target site 700. The processor 1562 and/or the graphics processing unit 1564 executes the program 1580b, which includes sending instructions to the image capture module 1404 to record right and left images of the color chart. Pixel data from the right and left images (after being processed by the de-Bayer program 1580a) may be compared to pixel data associated with the color chart, which may be stored to the memory 1570 from a peripheral unit 1576 and/or a remote computer via the network interface 1572. The processor 1562 and/or the graphics processing unit 1564 determines differences between the pixel data. The differences are stored to the memory 1570 as calibration data or parameters. The sensor color correction program 1580b applies the calibration parameters to subsequent right and left images.

In some examples, the differences may be averaged over regions of pixels such that the program 1580b finds a best-fit of color correction data that can be applied globally to all of the pixels of the optical image sensors 746 and 748 to produce colors as close to the color chart as possible. Additionally or alternatively, the program 1580b may process user input instructions received from the user unit device 1410 to correct colors. The instructions may include regional and/or global changes to red, blue, and green pixel data based on operator preferences.

The example sensor color correction program 1580b is also configured to correct for white balance. Generally, white light should result in red, green, and blue pixels having equal values. However, differences between pixels can result from color temperature of light used during imaging, inherent aspects of the filter and sensing element of each of the pixels, and spectral filtering parameters of, for example, the deflecting element 712 of FIGS. 7 and 8. The example sensor color correction program 1580b is configured to specify a calibration routine to correct for the light imbalances.

To perform white balance, the processor 1562 (per instructions from the program 1580b) may display an instruction on the display monitor 512 and/or 514 for an operator to place a neutral card at the target site 700. The processor 1562 may then instruct the image capture module 1404 to record one or more images of the neutral card. After processing by the unpack routine 1602 and the de-Bayer program 1580a, the program 1580b determines regional and/or global white balance calibration weight values for each of the red, blue, and green data such that each of the pixels have substantially equal values of red, blue, and green data. The white balance calibration weight values are stored to the memory 1570. During operation, the graphics processing unit 1564 uses the program 1580b to apply the white balance calibration parameters to provide white balance.

In some examples, the program 1580b determines white balance calibration parameters individually for the right and left optical image sensors 746 and 748. Of these examples, the program 1580b may store separate calibration parameters for the left and right images. In other instances, the sensor color correction program 1580b determines a weighting between the right and left views such that color pixel data is nearly identical for the right and left optical image sensors 746 and 748. The determined weight may be applied to the white balance calibration parameters for subsequent use during operation of the stereoscopic visualization camera 300.

In some embodiments, the sensor color correction program 1580b of FIG. 16 specifies that the white balance calibration parameters are to be applied as a digital gain on the pixels of the right and left optical image sensors 746 and 748. For example, the processor 1504 of the image capture module 1404 applies the digital gain to pixel data read from each of the pixels. In other embodiments, the white balance calibration parameters are to be applied as an analog gain for each pixel's color sensing element.

The example sensor color correction program 1580b may perform white balancing and/or color correction when the different light sources 708 and/or filter types of the filter 740 are activated. As a result, the memory 1570 may store different calibration parameters based on which light source 708 is selected. Further, the sensor color correction program 1580b may perform white balancing and/or color correction for different types of external light. An operator may use the user input device 1410 to specify characteristics and/or a type of the external light source. This calibration enables the stereoscopic visualization camera 300 to provide color correction and/or white balance for different lighting environments.

The example program 1580b is configured to perform calibration on each of the optical image sensors 746 and 748 separately. Accordingly, the program 1580b applies different calibration parameters to the right and left images during operation. However, in some examples, calibration may only be performed on one sensor 746 or 748 with the calibration parameters being used for the other sensor.

The example user color correction program 1580c is configured to request operator-provided feedback regarding image quality parameters such as brightness, contrast, gamma, hue, and/or saturation. The feedback may be received as instructions from the user input device 1410. Adjustments made by the user are stored as user calibration parameters in the memory 1570. These parameters are subsequently applied by the user color correction program 1580*c* to right and left optical images after color correction for the optical image sensors 746 and 748.

The example display color correction program 1580*d* of FIG. 16 is configured to correct image color for a display monitor using, for example, the Datacolor™ Spyder color checker. The program 1580*d*, similar to the program 1580*b*, instructs the image capture module 1404 to record an image of a display color template at the target scene 700. The display color correction program 1580*d* operates a routine to adjust pixel data to match an expected display output stored in a look-up-table in the memory 1570. The adjusted pixel data may be stored as display calibration parameters to the memory 1570. In some examples, a camera or other imaging sensor may be connected to the peripheral input unit interface 1574, which provides images or other feedback regarding color recorded from the display monitors 512 and 514, which is used to adjust the pixel data.

5. Stereoscopic Image Display Example

The example renderer program 1580*e* of the graphics processing unit 1564 of FIG. 16 is configured to prepare right and left images and/or frames for three-dimensional stereoscopic display. After the pixel data of the right and left images is color corrected by the programs 1580*b*, 1580*c*, and 1580*d*, the renderer program 1580*e* is configured to draw left-eye and right-eye data into a format suitable for stereoscopic display and place the final rendered version into an output buffer for transmission to one of the display monitors 512 or 514.

Generally, the renderer program 1580*e* receives a right image and/or frame and a left image and/or frame. The renderer program 1580*e* combines the right and left images and/or frames into a single frame. In some embodiments, the program 1580*e* operates a top-bottom mode and condenses the left image data in height by half. The program 1580*e* then places the condensed left image data in a top half of the combined frame. Similarly, the program 1580*e* condenses the right image data in height by half and places the condensed right image data in a bottom half of the combined frame.

In other embodiments, the renderer program 1580*e* operates a side-by-side mode where each of the left and right images are condensed in width by half and combined in a single image such that the left image data is provided on a left half of the image while right image data is provided on a right half of the image. In yet an alternative embodiment, the renderer program 1580*e* operates a row-interleaved mode where every other line in the left and right frames is discarded. The left and right frames are combined together to form a complete stereoscopic image.

The example renderer program 1580*e* is configured to render combined left and right images separately for each connected display monitor. For instance, if both the display monitors 512 and 514 are connected, the renderer program 1580*e* renders a first combined stereoscopic image for the display monitor 512 and a second combined stereoscopic image for the display monitor 514. The renderer program 1580*e* formats the first and second combined stereoscopic images such that they are compatible with the type and/or screen size of the display monitors and/or screen.

In some embodiments, the renderer program 1580*e* selects the image processing mode based on how the display monitor is to display stereoscopic data. Proper interpretation of stereoscopic image data by the brain of an operator requires that the left eye data of the stereoscopic image be conveyed to the operator's left eye and the right eye data of the stereoscopic image be conveyed to the operator's right eye. Generally, display monitors provide a first polarization for left eye data and a second opposing polarization for the right eye data. Thus, the combined stereoscopic image must match the polarization of the display monitor.

Figure 17:
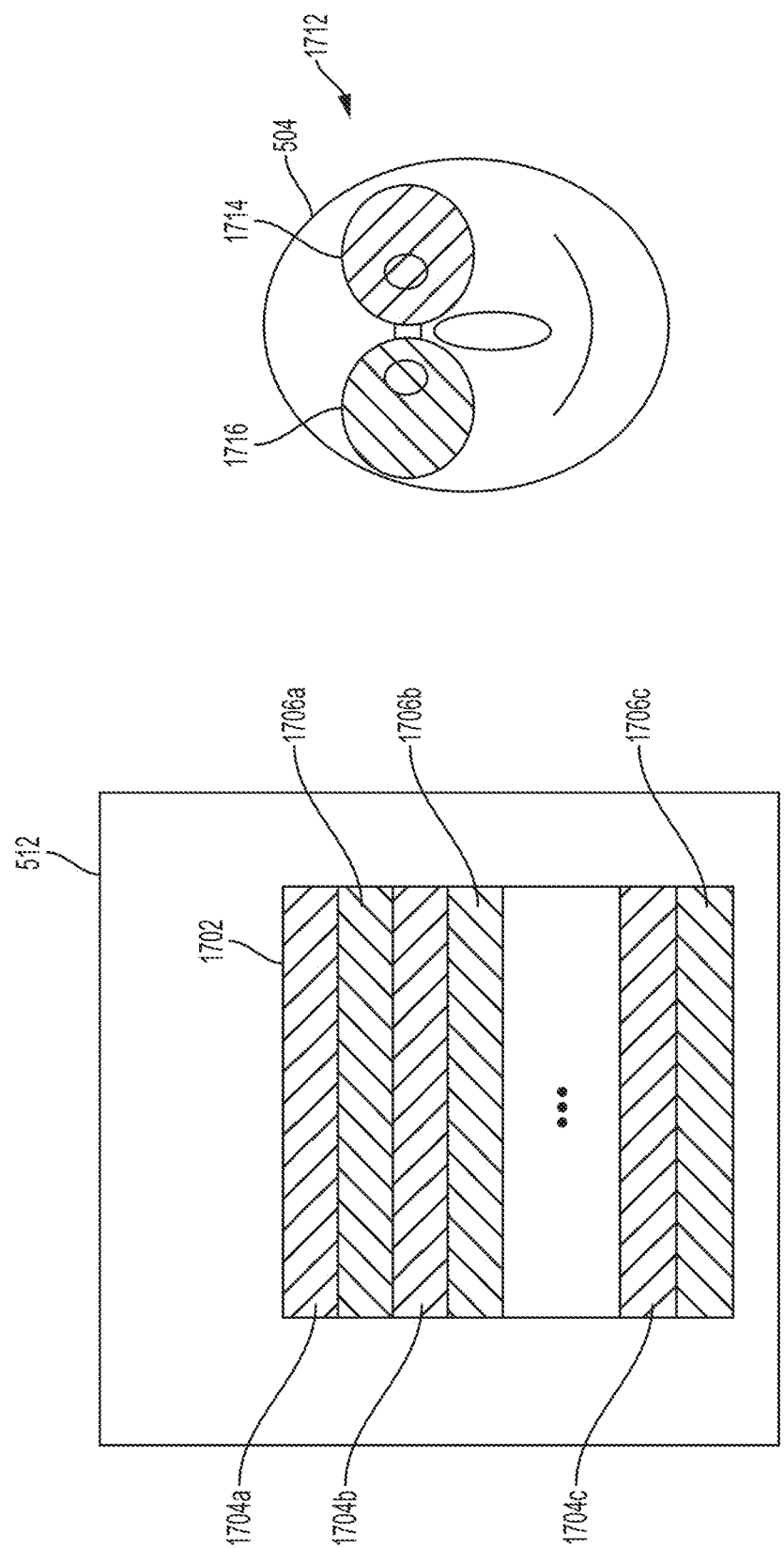
FIG. 17 shows an example of a display monitor, according to an example embodiment of the present disclosure.

FIG. 17 shows an example of the display monitor 512, according to an example embodiment of the present disclosure. The display monitor 512 may be, for example, the LG® 55LW5600 three-dimensional television with a screen 1702. The example display monitor 512 uses a polarization film on the screen 1702 such that all odd rows 1704 have a first polarization and all even rows 1706 have an opposing polarization. For compatibility with the display monitor 512 shown in FIG. 17, the renderer program 1580*e* would have to select the row-interleaved mode such that the left and right image data are on alternating lines. In some instances, the renderer program 1580*e* may request (or otherwise receive) display characteristics of the display monitor 512 prior to preparing the stereoscopic image.

To view the stereoscopic image displayed on the screen 1702, the surgeon 504 (remember him from FIG. 5) wears glasses 1712 that include a left lens 1714 that comprises a first polarization that matches the first polarization of the rows 1704. In addition, the glasses 1712 include a right lens 1716 that comprises a second polarization that matches the second polarization of the rows 1706. Thus, the left lens 1714 only permits a majority of the light from the left image data from the left rows 1704 to pass through while blocking a majority of the light from the right image data. In addition, the right lens 1716 permits a majority of the light from the right image data from the right rows 1706 to pass through while blocking a majority of the light from the left image data. The amount of light from the "wrong" view that reaches each respective eye is known as "crosstalk" and is generally held to a value low enough to permit comfortable viewing. Accordingly, the surgeon 504 views left image data recorded by the left optical image sensor 748 in a left eye while viewing right image data recorded by the right optical image sensor 746 in a right eye. The surgeon's brain fuses the two views together to create a perception of three-dimensional distance and/or depth. Further, the use of such a display monitor is advantageous for observing the accuracy of the stereoscopic visualization camera 300. If the surgeon or operator does not wear glasses, then both left and right views are observable with both eyes. If a planar target is placed at the focal plane, the two images will be theoretically aligned. If misalignment is detected, a re-calibration procedure can be initiated by the processor 1562.

The example renderer program 1580*e* is configured to render the left and right views for circular polarization. However, in other embodiments, the renderer program 1580*e* may provide a stereoscopic image compatible with linear polarization. Regardless of which type of polarization is used, the example processor 1562 may execute a program 1560 to verify or check a polarity of the stereoscopic images being output by the renderer program 1580*e*. To check polarity, the processor 1562 and/or the peripheral input unit interface 1574 inserts diagnostic data into the left and/or right images. For example, the processor 1562 and/or the peripheral input unit interface 1574 may overlay "left" text onto the left image and "right" text onto the right image. The processor 1562 and/or the peripheral input unit interface 1574 may display a prompt instructing an operator to close one eye at a time while wearing the glasses 1712 to confirm the left view is being received at the left eye and the right view is being received at the right eye. The operator may provide confirmation via the user input device 1410 indicating whether the polarization is correct. If the polarization is not correct, the example renderer program 1580e is configured to reverse locations where the left and right images are inserted into the combined stereoscopic image.

In yet other embodiments, the example renderer program 1580e is configured to provide for frame sequential projection instead of creating a combined stereoscopic image. Here, the renderer program 1580e renders the left images and or frames time-sequentially interleaved with the right images and/or frames. Accordingly the left and right images are alternately presented to the surgeon 504. In these other embodiments, the screen 1702 is not polarized. Instead, the left and right lenses of the glasses 1712 may be electronically or optically synchronized to their respective portion of a frame sequence, which provides corresponding left and right views to a user to discern depth.

In some examples, the renderer program 1580e may provide certain of the right and left images for display on separate display monitors or separate windows on one display monitor. Such a configuration may be especially beneficial when lenses of right and left optical paths of the optical elements 1402 are independently adjustable. In an example, a right optical path may be set a first magnification level while a left optical path is set at a second magnification level. The example renderer program 1580e may accordingly display a stream of images from the left view on the display monitor 512 and a stream of images from the right view on the display monitor 514. In some instances, the left view may be displayed in a first window on the display monitor 512 while the right view is displayed in a second window (e.g., a picture-in-picture) of the same display monitor 512. Thus, while not stereoscopic, the concurrent display of the left and right images provides useful information to a surgeon.

In another example, the light sources 708 and the filter 740 may be switched quickly to generate alternating images with visible light and fluorescent light. The example renderer program 1580e may combine the left and right views to provide a stereoscopic display under different lighting sources to highlight, for example, a vein with a dye agent while showing the background in visible light.

In yet another example, a digital zoom may be applied to the right and/or left optical image sensor 746 or 748. Digital zoom generally affects the perceived resolution of the image and is dependent on factors such as the display resolution and the preference of the viewer. For example, the processor 1504 of the image capture module 1404 may apply digital zooming by creating interpolated pixels synthesized and interspersed between the digitally-zoomed pixels. The processor 1504 may operate a program 1510 that coordinates the selection and interpolation pixels for the optical image sensors 746 and 748. The processor 1504 transmits the right and left images with digital zoom applied to the information processor module 1408 for subsequent rendering and display.

In some embodiments, the processor 1504 receives instructions from the processor 1562 that a digital zoom image is to be recorded between images without digital zoom to provide a picture-in-picture (or separate window) display of a digital zoom of a region of interest of the target site 700. The processor 1504 accordingly applies digital zooming to every other read from the pixel grids 1002 and 1004. This enables the renderer program 1580e to display simultaneously a stereoscopic full resolution image in addition to a digitally-zoomed stereoscopic image. Alternatively, the image to be zoomed digitally is copied from the current image, scaled, and placed during the render phase in the proper position overlaid atop the current image. This alternatively configuration avoids the "alternating" recording requirement.

6. Calibration Example

The example information processor module 1408 of FIGS. 14 to 16 may be configured to execute one or more calibration programs 1560 to calibrate, for example, a working distance and/or magnification. For example, the processor 1562 may send instructions to the motor and lighting module 1406 to perform a calibration step for mapping a working distance (measured in millimeters) from the main objective assembly 702 to the target site 700 to a known motor position of the working distance lens motor 1554. The processor 1562 performs the calibration by sequentially moving an object plane in discrete steps along the optical axis and re-focusing the left and right images, while recording encoder counts and the working distance. In some examples, the working distance may be measured by an external device, which transmits the measured working distance values to the processor 1562 via the peripheral input unit interface 1574 and/or an interface to the user input device 1410. The processor 1562 may store the position of the rear working distance lens 704 (based on position of the working distance lens motor 1554) and the corresponding working distance.

The example processor 1562 may also execute a program 1560 to perform magnification calibration. The processor 1562 may set the optical elements 1402, using the motor and lighting module 1406 to select magnification levels. The processor 1562 may record positions of the optical elements 1402, or corresponding motor positions with respect to each magnification level. The magnification level may be determined by measuring a height in an image of an object of a known size. For example, the processor 1562 may measure an object as having a height of 10 pixels and use a look-up-table to determine that a 10 pixel height corresponds to a 5× magnification.

To match the stereoscopic perspectives of two different imaging modalities it is often desirable to model them both as if they are simple pinhole cameras. The perspective of a 3D computer model, such as a MM brain tumor, can be viewed from user-adjustable directions and distances (e.g. as if the images are recorded by a synthesized stereoscopic camera). The adjustability can be used to match the perspective of the live surgical image, which must therefore be known. The example processor 1562 may calibrate one or more of these pinhole camera parameters such as, for example, a center of projection ("COP") of the right and left optical image sensors 746 and 748. To determine center of projection, the processor 1562 determines a focus distance from the center of projection to an object plane. First, the processor 1562 sets the optical elements 1402 at a magnification level. The processor 1562 then records measurements of a height of an image at three different distances along the optical axis including at the object plane, a distance d less than the object plane distance, and a distance d greater than the object plane distance. The processor 1562 uses an algebraic formula for similar triangles at the two most extreme positions to determine the focus distance to the center of projection. The processor 1562 may determine focus distances at other magnifications using the same method or by determining a ratio between the magnifications used for calibration. The processor may use a center of projection to match the perspective of an image of a desired fusion object, such as an MM tumor model, to a live stereoscopic surgical image. Additionally or alternatively, existing camera calibration procedures such as OpenCV calibrateCamera may be used to find the above-described parameters as well as additional camera information such as a distortion model for the optical elements 1402.

The example processor 1562 may further calibrate the left and right optical axes. The processor 1562 determines an interpupillary distance between the left and right optical axes for calibration. To determine the interpupillary distance, the example processor 1562 records left and right images where pixel sets 1006 and 1008 are centered at the pixel grids 1002 and 1004. The processor 1562 determines locations of ZRPs (and/or distances to a displaced object) for the left and right images, which are indicative of image misalignment and degree of parallax. In addition, the processor 1562 scales the parallax and/or the distance based on the magnification level. The processor 1562 then determines the interpupillary distance using a triangulation calculation taking into account the degree of parallax and/or the scaled distance to the object in the display. The processor 1562 next associates the interpupillary distance with the optical axis at the specified magnification level as a calibration point.

VI. Image Alignment and Spurious Parallax Adjustment Embodiment

Similar to human vision, stereoscopic images comprise right views and left views that converge at a point of interest. The right and left views are recorded at slightly different angles from the point of interest, which results in parallax between the two views. Items in the scene in front of or behind the point of interest exhibit parallax such that distance or depth of the items from the viewer can be deduced. The accuracy of the perceived distance is dependent on, for example, the clarity of the viewer's eyesight. Most humans exhibit some level of imperfection in their eyesight, resulting in some inaccuracies between the right and left views. However, they are still able to achieve stereopsis, with the brain fusing the views with some level of accuracy.

When left and right images are recorded by a camera instead of being viewed by a human, the parallax between the combined images on a display screen produces stereopsis, which provides an appearance of a three-dimensional stereoscopic image on a two-dimensional display. Errors in the parallax can affect the quality of the three-dimensional stereoscopic image. The inaccuracy of the observed parallax in comparison to a theoretically perfect parallax is known as spurious parallax. Unlike humans, cameras do not have brains that automatically compensate for the inaccuracies.

If spurious parallax becomes significant, the three-dimensional stereoscopic image may be unviewable to the point of inducing vertigo, headaches, and nausea. There are many factors that can affect the parallax in a microscope and/or camera. For instance, optical channels of the right and left views may not be exactly equal. The optical channels may have unmatched focus, magnification, and/or misalignment of points of interest. These issues may have varying severity at different magnifications and/or working distances, thereby reducing efforts to correct through calibration.

Figure 2:
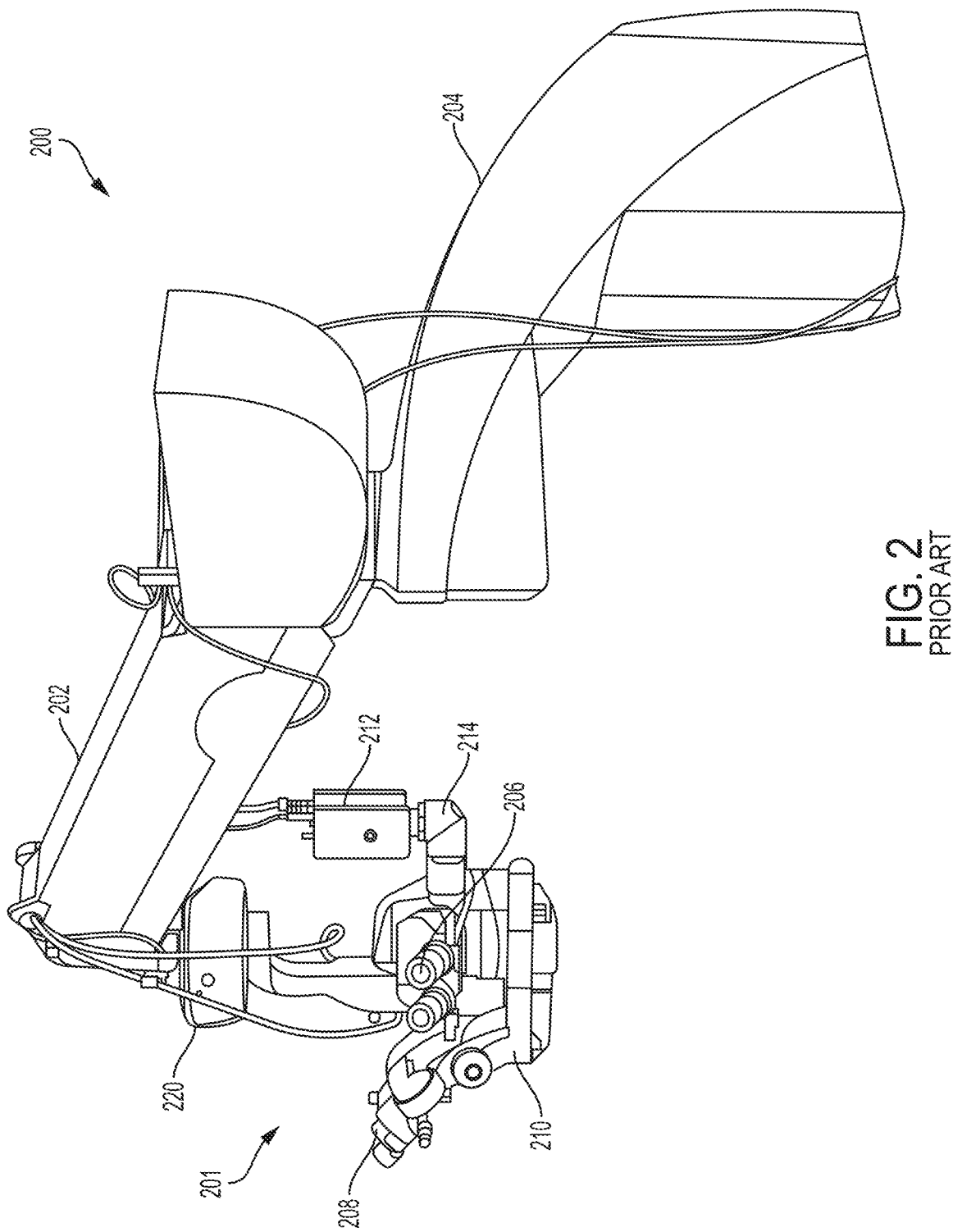
FIG. 2 shows a diagram of a prior art surgical microscope.

Known surgical microscopes, such as the surgical microscope 200 of FIG. 2 are configured to provide an adequate view through the oculars 206. Often, the image quality of optical elements of known surgical microscopes is not sufficient for stereoscopic cameras. The reason for this is because manufacturers of surgical microscopes assume the primary viewing is through oculars. Any camera attachment (such as the camera 212) is either monoscopic and not subject to spurious parallax or stereoscopic with low image resolution where spurious parallax is not as apparent.

International standards, such as ISO 10936-1:2000, *Optics and optical instruments—Operation microscopes—Part 1: Requirements and test methods*, have been developed to provide specification limits for image quality of surgical microscopes. The specification limits are generally set for viewing through the oculars of a surgical microscope and do not consider three-dimensional stereoscopic display. For example, regarding spurious parallax, ISO 10936-1:2000 specifies that the difference in vertical axes between the left and right views should be less than 15 arc-minutes. Small angular deviations of axes are often quantified in arc-minutes, which corresponds to 1/60 of a degree, or arc-seconds, which corresponds to 1/60 of an arc-minute. The 15 arc-minute specification limit corresponds to a 3% difference between left and right views for a typical surgical microscope with a working distance of 250 mm and a field-of-view of 35 mm (which has an angular field-of-view of 8°).

The 3% difference is acceptable for ocular viewing where a surgeon's brain is able to overcome the small degree of error. However, this 3% difference produces noticeable differences between left and right views when viewed stereoscopically on a display monitor. For example, when the left and right views are shown together, a 3% difference results in an image that appears disjointed and difficult to view for extended periods of time.

Another issue is that known surgical microscopes may satisfy the 15 arc-minute specification limit at only one or a few magnification levels and/or only individual optical elements may satisfy a certain specification limit. For example, individual lenses are manufactured to meet certain criteria. However, when the individual optical elements are combined in an optical path, small deviations from the standard may be amplified rather than cancelled. This can be especially pronounced when five or more optical elements are used in an optical path including a common main objective lens. In addition, it is very difficult to perfectly match optical elements on parallel channels. At most, during manufacture, the optical elements of a surgical microscope are calibrated only at one or a few certain magnification levels to meet the 15 arc-minute specification limit. Accordingly, the error may be greater between the calibration points despite the surgical microscope allegedly meeting the ISO 10936-1:2000 specifications.

In addition, the ISO 10936-1:2000 specification permits larger tolerances when additional components are added. For example, adding second oculars (e.g., the oculars 208) increases the spurious parallax by 2 arc-minutes. Again, while this error may be acceptable for viewing through oculars 206 and 208, image misalignment becomes more pronounced when viewed stereoscopically through the camera.

In comparison to known surgical microscopes, the example stereoscopic visualization camera 300 disclosed herein is configured to automatically adjust at least some of the optical elements 1402 to reduce or eliminate spurious parallax. Embedding the optical elements within the stereoscopic visualization camera 300 enables fine adjustments to be made automatically (sometimes in real-time) for three-dimensional stereoscopic display. In some embodiments, the example stereoscopic visualization camera 300 may provide an accuracy of 20 to 40 arc-seconds, which is close to a 97% reduction in optical error compared to the 15 arc-minute accuracy of known surgical microscopes.

The improvement in accuracy enables the example stereoscopic visualization camera 300 to provide features that are not capable of being performed with known stereoscopic microscopes. For example, many new microsurgical procedures rely on accurate measurements in a live surgical site for optimal sizing, positioning, matching, directing, and diagnosing. This includes determining a size of a vessel, an angle of placement of a toric Intra Ocular Lens ("IOL"), a matching of vasculature from a pre-operative image to a live view, a depth of a tumor below an artery, etc. The example stereoscopic visualization camera 300 accordingly enables precise measurements to be made using, for example, graphical overlays or image analysis to determine sizes of anatomical structures.

Known surgical microscopes require that a surgeon place an object of a known size (such as a micro-ruler) into the field-of-view. The surgeon compares the size of the object to surrounding anatomical structure to determine an approximate size. However, this procedure is relatively slow since the surgeon has to place the object in the proper location, and then remove it after the measurement is performed. In addition, the measurement only provides an approximation since the size is based on the surgeon's subjective comparison and measurement. Some known stereoscopic cameras provide graphical overlays to determine size. However, the accuracy of these overlays is reduced if spurious parallax exists between the left and right views.

A. ZRP as a Source of Spurious Parallax

Figure 18:
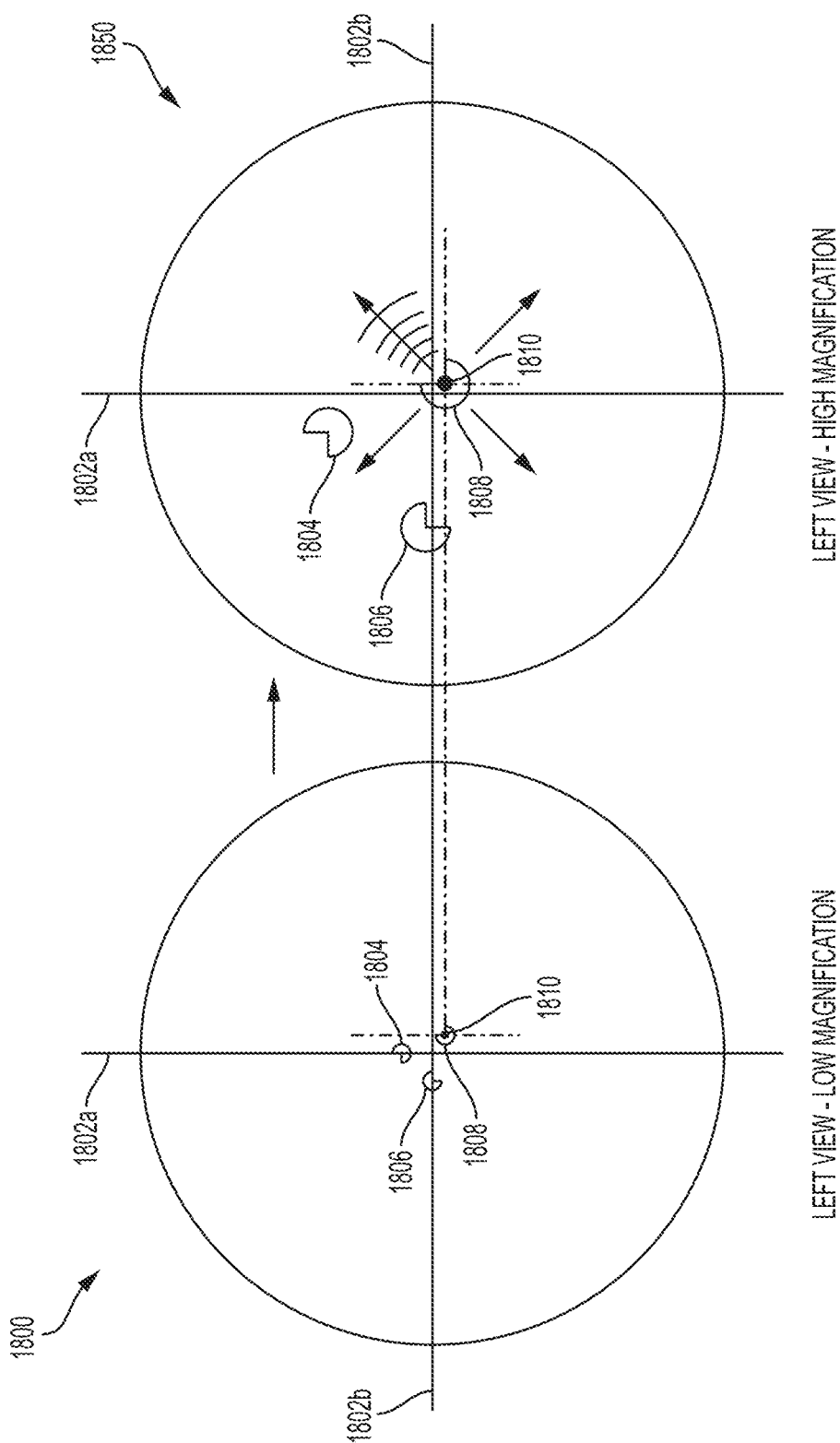
FIGS. 18 to 21 show diagrams illustrative of spurious parallax between right and left optical paths.
Figure 19:
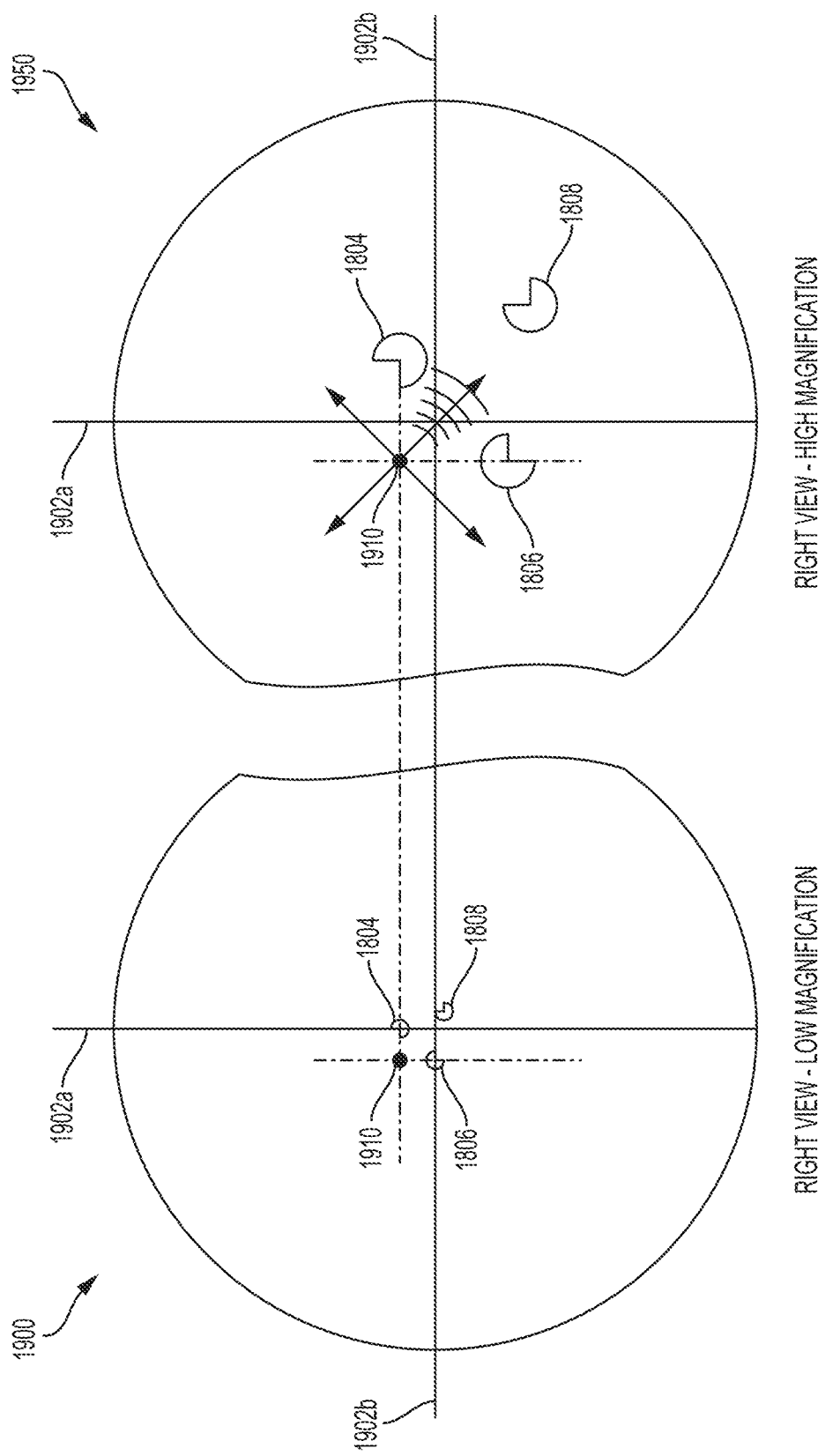

ZRP inaccuracy provides a significant source of error between left and right images resulting in spurious parallax. ZRP, or zoom repeat point, refers to a point in a field-of-view that remains in a same location as a magnification level is changed. FIGS. 18 and 19 show examples of ZRP in a left and right field-of-view for different magnification levels. Specifically, FIG. 18 shows a left field-of-view 1800 for a low magnification level and a left field-of-view 1850 for a high magnification level. In addition, FIG. 19 shows a right field-of-view 1900 for a low magnification level and a right field-of-view 1950 for a high magnification level.

It should be noted that FIGS. 18 and 19 show crosshairs 1802 and 1902 to provide an exemplary point of reference for this disclosure. The crosshairs 1802 include a first crosshair 1802a positioned along a y-direction or y-axis and a second crosshair 1802b positioned along an x-direction or x-axis. Additionally, crosshairs 1902 include a first crosshair 1902a positioned along a y-direction or y-axis and a second crosshair 1902b positioned along an x-direction or x-axis. In actual implementation, the example stereoscopic visualization camera 300 by default typically does not include or add crosshairs to the optical path unless requested by an operator.

Ideally, the ZRP should be positioned at a central location or origin point. For example, the ZRP should be centered in the crosshairs 1802 and 1902. However, inaccuracies in the optical elements 1402 and/or slight misalignments between the optical elements 1402 cause the ZRP to be located away from the center of the crosshairs 1802 and 1902. The degree of spurious parallax corresponds to how far each of the ZRPs of the left and right views is located away from the respective centers in addition to ZRPs being misaligned between the left and right views. Moreover, inaccuracies in the optical elements 1402 may cause the ZRP to drift slightly as magnification changes, thereby further causing a greater degree of spurious parallax.

FIG. 18 shows three crescent-shaped objects 1804, 1806, and 1808 in the field-of-views 1800 and 1850 of the target site 700 of FIG. 7. It should be appreciated that the field-of-views 1800 and 1850 are linear field-of-views with respect to the optical image sensors 746 and 748. The objects 1804, 1806, and 1808 were placed in the field-of-view 1800 to illustrate how spurious parallax is generated from left and right image misalignment. The object 1804 is positioned above crosshair 1802b along crosshair 1802a. The object 1806 is positioned along crosshair 1802b and to the left of the crosshair 1802a. The object 1808 is positioned slightly below the crosshair 1802b and to the right of the crosshair 1802a. A ZRP 1810 for the left field-of-view 1800 is positioned in a notch of the object 1808.

The left field-of-view 1800 is changed to the left field-of-view 1850 by increasing the magnification level (e.g., zooming) using the zoom lens assembly 716 of the example stereoscopic visualization camera 300. Increasing the magnification causes the objects 1804, 1806, and 1808 to appear to expand or grow, as shown in the field-of-view 1850. In the illustrated example, the field-of-view 1850 is approximately 3× the magnification level of the field-of-view 1800.

Compared to the low magnification field-of-view 1800, the objects 1804, 1806, and 1808 in high magnification field-of-view 1850 have increased in size by about 3× while also moving apart from each other by 3X with respect to the ZRP 1810. In addition, the positions of the objects 1804, 1806, and 1808 have moved relative to the crosshairs 1802. The object 1804 is now shifted to the left of the crosshair 1802a and shifted slightly further from the crosshair 1802b. In addition, the object 1806 is now shifted further to the left of crosshair 1802a and slightly above the crosshair 1802b. Generally, the object 1808 is located in the same (or nearly the same) position with respect to the crosshairs 1802, with the ZRP 1810 being located in the exact same (or nearly the same) position with respect to the crosshairs 1802 and the object 1806. In other words, as magnification increases, the objects 1804, 1806, and 1808 (and anything else in the field-of-view 1850) appear to move away and outward from the ZRP 1810.

The same objects 1804, 1806, and 1808 are shown in the right field-of-views 1900 and 1950 illustrated in FIG. 19. However, the location of the ZRP is different. Specifically, Z R P 1910 is located above crosshair 1902b and to the left of crosshair 1902a in the right field-of-views 1900 and 1950. Thus, the ZRP 1910 is located at a different location than the ZRP 1810 in the left field-of-views 1800 and 1850. In the illustrated example, it is assumed that the left and right optical paths are perfectly aligned at the first magnification level. Accordingly, the objects 1804, 1806, and 1808 shown in the right field-of-view 1900 in the same location as the same objects 1804, 1806, and 1808 in the left field-of-view 1800. Since the left and right views are aligned, no spurious parallax exists.

However, in the high magnification field-of-view 1950, the objects 1804, 1806, and 1808 expand and move away from the ZRP 1910. Given the location of the ZRP 1910, the object 1804 moves or shifts to the right and the object 1806 moves or shifts downward. In addition, the object 1808 moves downward and to the right compared to its location in the field-of-view 1900.

Figure 20:
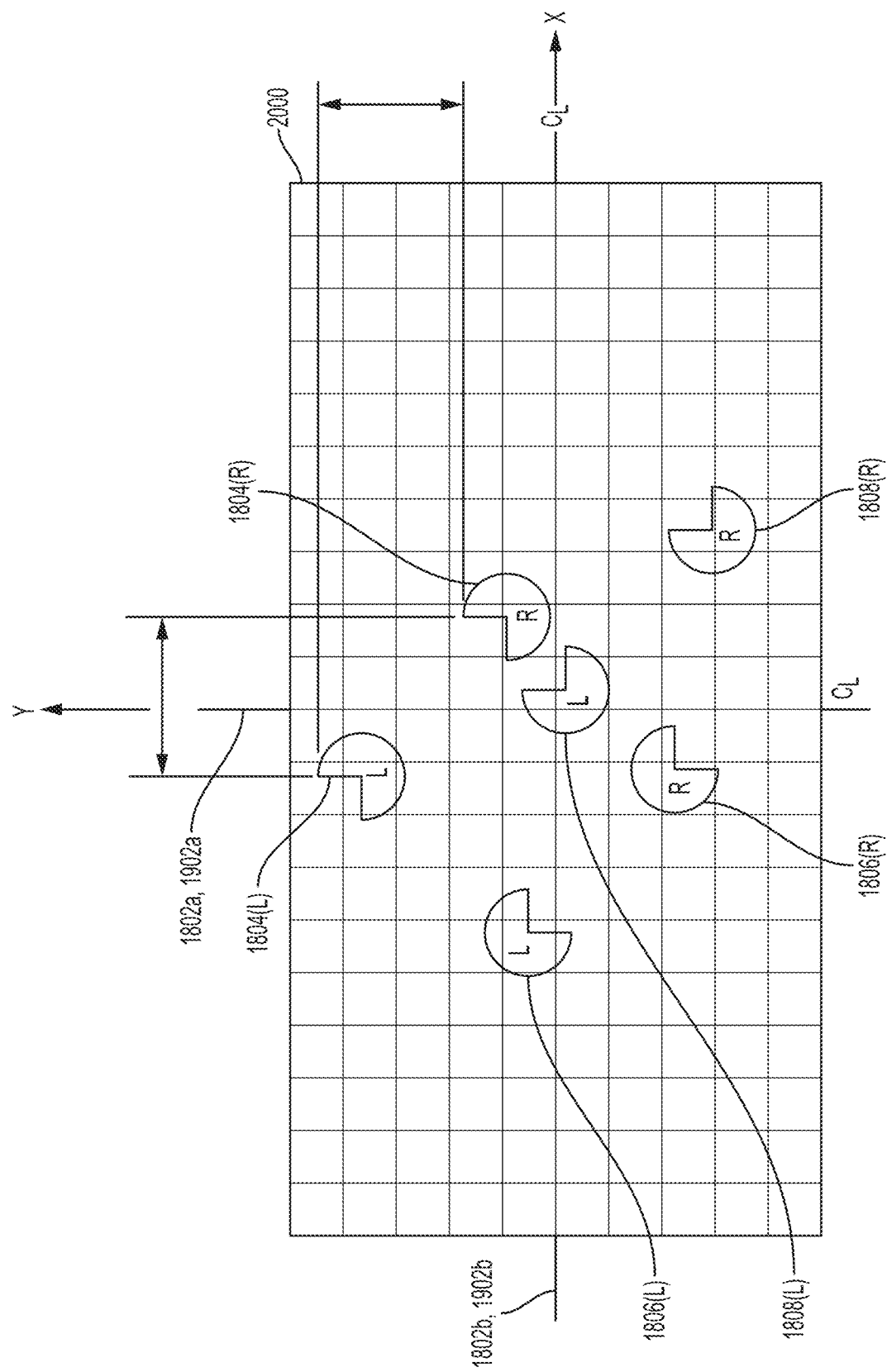

FIG. 20 shows a pixel diagram comparing the high magnification left field-of-view 1850 to the high magnification right field-of-view. A grid 2000 may represent locations of the objects 1804(L), 1806(L), and 1808(L) on the pixel grid 1004 of the left optical image sensor 748 overlaid with locations of the objects 1804(R), 1806(R), and 1808(R) on the pixel grid 1002 of the left optical image sensor 746. FIG. 20 clearly shows that the objects 1804, 1806, and 1808 are in different positions for the left and right field-of-views 1850 and 1950. For example, the object 1804(R) is located to the right of crosshair 1902a and above crosshair 1902b while the same object 1804(L) is located to the left of cross hair 1802a and further above cross hair 1802b.

The difference in positions of the objects 1804, 1806, and 1808 corresponds to spurious parallax, which is created by deficiencies in the optical alignment of the optical elements 1402 that produce ZRPs 1810 and 1910 in different locations. Assuming no distortion or other imaging errors, the spurious parallax shown in FIG. 20 is generally the same for all points within the image. When viewed through oculars of a surgical microscope (such as microscope 200 of FIG. 2), the difference in location of the objects 1804, 1806, and 1808 may not be noticeable. However, when viewed on the display monitors 512 and 514 in a stereoscopic image, the differences become readily apparent and can result in headaches, nausea, and/or vertigo.

Figure 21:
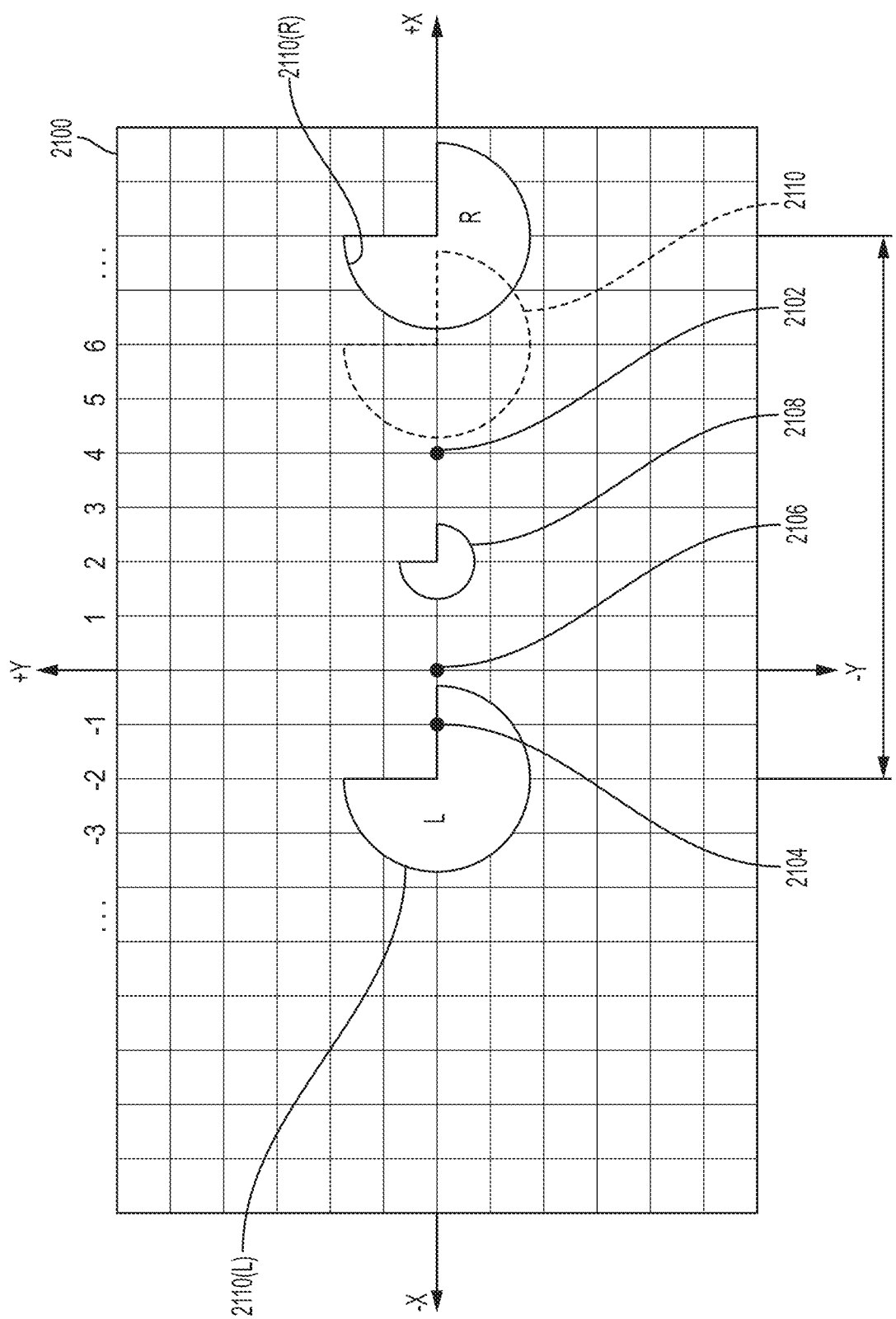

FIG. 21 shows a diagram illustrative of spurious parallax with respect to left and right ZRPs. The diagram includes a pixel grid 2100 that includes overlays of the right and left pixel grids 1002 and 1004 of FIG. 10. In this illustrated example, a left ZRP 2102 for the left optical path is located at +4 along the x-axis and 0 along the y-axis. In addition, a right ZRP 2104 for the right optical path is located at −1 along the x-axis and 0 along the y-axis. An origin 2106 is shown at the intersection of the x-axis and the y-axis.

In this example, object 2108 is aligned with respect to the left and right images at a first low magnification. As magnification is increased by 3×, the object 2108 increased in size and moved away from the ZRPs 2102 and 2104. Outlines object 2110 shows a theoretical location of the object 2108 at the second higher magnification based on the ZRPs 2102 and 2104 being aligned with the origin 2106. Specifically, a notch of the object 2108 at the first magnification level is at location +2 along the x-axis. With 3× magnification, the notch moves 3X along the x-axis such that the notch is located at +6 along the x-axis at the higher magnification level. In addition, since the ZRPs 2102 and 2104 would be theoretically aligned at the origin 2106, the object 2110 would be aligned between the left and right views (shown in FIG. 21 as a single object given the overlay).

However, in this example, misalignment of the left and right ZRPs 2102 and 2104 causes the object 2110 to be misaligned between the left and right views at higher magnification. Regarding the right optical path, the right ZRP 2104 is located at −1 along the x-axis such that it is 3 pixels away from the notch of the object 2108 at low magnification. When magnified 3×, this difference becomes 9 pixels, which is shown as object 2110(R). Similarly, the left ZRP 2102 is located at +4 pixels along the x-axis. At 3× magnification, the object 2108 moves from being 2 pixels away to 6 pixels away, which is shown as object 2110(L) at −2 along the x-axis.

The difference in positions of the object 2110(L) and the object 2110(R) corresponds to the spurious parallax between the left and right views at the higher magnification. If the right and left views were combined into a stereoscopic image for display, the location of the object 2110 would be misaligned at each row if the renderer program 1850e uses a row-interleaved mode. The misalignment would be detrimental to generating stereopsis and may produce an image that appears blurred or confusing to an operator.

B. Other Sources of Spurious Parallax

While ZRP misalignment between left and right optical paths is a significant source of spurious parallax, other sources of error also exist. For example, spurious parallax may result from non-equal magnification changes between the right and left optical paths. Differences in magnification between parallel optical paths may result from slight variances in the optical properties or characteristics of the lenses of the optical elements 1402. Further, slight differences may result from positioning if each of the left and right front zoom lenses 726 and 728 and each of the left and right rear zoom lenses 736 and 738 of FIGS. 7 and 8 are independently controlled.

Referring back to FIGS. 18 and 19, differences in magnification change produce differently sized objects and different spacing between the objects for the left and right optical paths. If, for example, the left optical path has a higher magnification change, then the objects 1804, 1806, and 1808 will appear larger and move a greater distance from the ZRP 1810 compared to the objects 1804, 1806, and 1808 in the right field-of-view 1950 in FIG. 19. The difference in the location of the objects 1804, 1806, and 1808, even if the ZRPs 1810 and 1910 are aligned, results in spurious parallax.

Another source of spurious parallax results from unequal focusing of the left and right optical paths. Generally, any difference in focus between left and right views may cause a perceived diminishment in image quality and potential confusion over whether the left or right view should predominate. If the focus difference is noticeable, it can result in an Out-Of-Focus ("OOF") condition. OOF conditions are especially noticeable in stereoscopic images where left and right views are shown in the same image. In addition, OOF conditions are not easily correctable since re-focusing an out-of-focus optical path usually results in the other optical path becoming unfocused. Generally, a point needs to be determined where both optical paths are in focus, which may include changing positions of left and right lenses along an optical path and/or adjusting a working distance from the target site 700.

Figure 22:
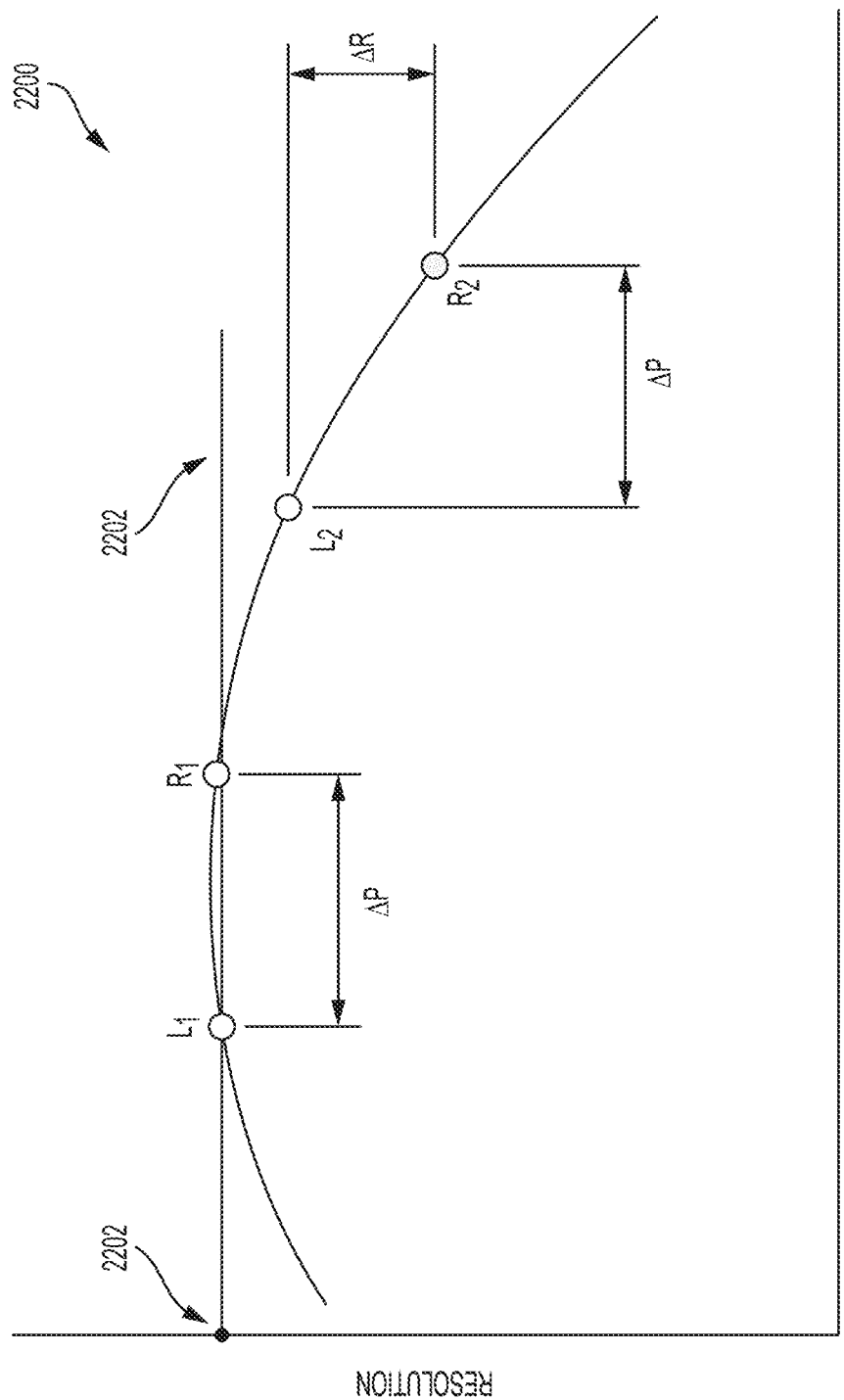
FIG. 22 shows a diagram illustrative of an out-of-focus condition in relation to a position of two parallel lenses for respective right and left optical paths.

FIG. 22 shows a diagram illustrative of how an OOF condition develops. The diagram relates perceived resolution (e.g., focus) to a lens position relative to an optimal resolution section 2202. In this example the left rear zoom lens 734 is at position L1 while the right rear zoom lens 732 is at position R1. At position L1 and R1, the rear zoom lenses 732 and 734 are in a range of optimal resolution 2202 such that the left and right optical paths have matched focus levels. However, there is a difference in the positions of L1 and R1, corresponding to distance ΔP. At a later time, the working distance 706 is changed such that a point is out-of-focus. In this example, both rear zoom lenses 732 and 734 move the same distance to locations L2 and R2 such that distance ΔP does not change. However, the position change results in a significant change in resolution ΔR such that the left rear zoom lens 734 has a higher resolution (e.g., better focus) that the right rear zoom lens 732. The resolution ΔR corresponds to the OOF condition, which results in spurious parallax from misalignment of focus between the right and left optical paths.

Yet another source of spurious parallax can result from imaging objects that are moving at the target site 700. The spurious parallax results from small synchronization errors between exposures of the right and left optical image sensors 746 and 748. If the left and right views are not recorded simultaneously, then the object appears to be displaced or misaligned between the two views. The combined stereoscopic image shows the same object at two different locations for the left and right views.

Moreover, another source of spurious parallax involves a moving ZRP point during magnification. The examples discussed above in Section IV(A) assume that the ZRPs of the left and right views do not move in the x-direction or the y-direction. However, the ZRPs may shift during magnification if the zoom lenses 726, 728, 732, and/or 734 do not move exactly parallel with the optical path or axis (e.g., in the z-direction). As discussed above in reference to FIG. 11, the carrier 724 may shift or rotate slightly when a force is applied to the actuation section 1108. This rotation may cause the left and right ZRPs to move slightly when a magnification level is changed.

In an example, during a magnification change, the carrier 730 moves in a single direction while the carrier 724 moves in the same direction for a portion of the magnification change and in an opposite direction for a remaining portion of the magnification change for focus adjustment. If the axis of motion of the carrier 724 is tilted or rotated slightly with respect to the optical axis, the ZRP of the left and/or right optical paths will shift in one direction for the first portion followed by a shift in a reverse direction for the second portion of the magnification change. In addition, since the force is applied unequally, the right and left front zoom lenses 726 and 728 may experience varying degrees of ZRP shift between the left and right optical paths. Altogether, the change in position of the ZRP results in misaligned optical paths, thereby producing spurious parallax.

C. Reduction in Spurious Parallax Facilitates Incorporating Digital Graphics and Images with a Stereoscopic View As surgical microscopes become more digitalized, designers are adding features that overlay graphics, images, and/or other digital effects to the live-view image. For example, guidance overlays, fusion of stereoscopic Magnetic Resonance Imaging ("MRI") images, and/or external data may be combined with images recorded by a camera, or even displayed within oculars themselves. Spurious parallax reduces the accuracy of the overlay with the underlying stereoscopic image. Surgeons generally require, for example, that a tumor visualized via MRI be placed as accurately as possible, often in three dimensions, within a fused live surgical stereoscopic view. Otherwise, the preoperative tumor image provides little information to the surgeon, thereby detracting from the performance.

For example, a surgical guide may be aligned with a right view image while misaligned with the left view. The misaligned surgical guide between the two views is readily apparent to the operator. In another example, a surgical guide may be aligned separately with left and right views in the information processor module 1408 prior to the graphics processing unit 1564 creating the combined stereoscopic image. However, misalignment between the left and right views creates misalignment between the guides, thereby reducing the effectiveness of the guides and creating confusion and delay during the microsurgical procedure.

Figure 23:
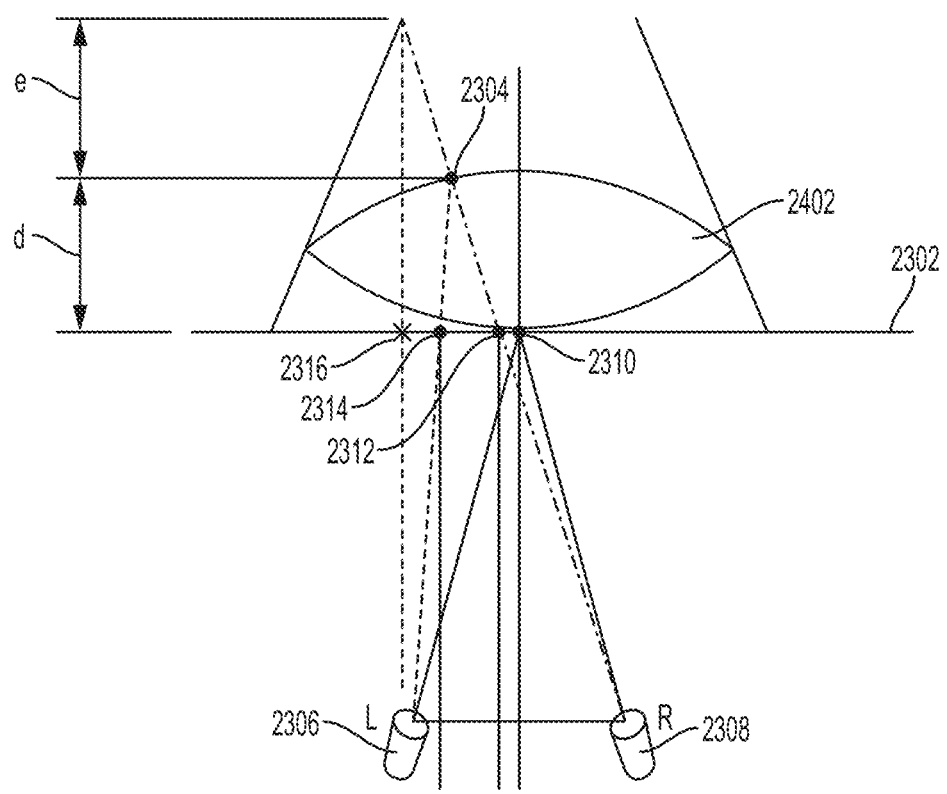
FIGS. 23 and 24 show diagrams illustrative of how spurious parallax causes digital graphics and/or images to lose accuracy when fused to a stereoscopic image.
Figure 24:
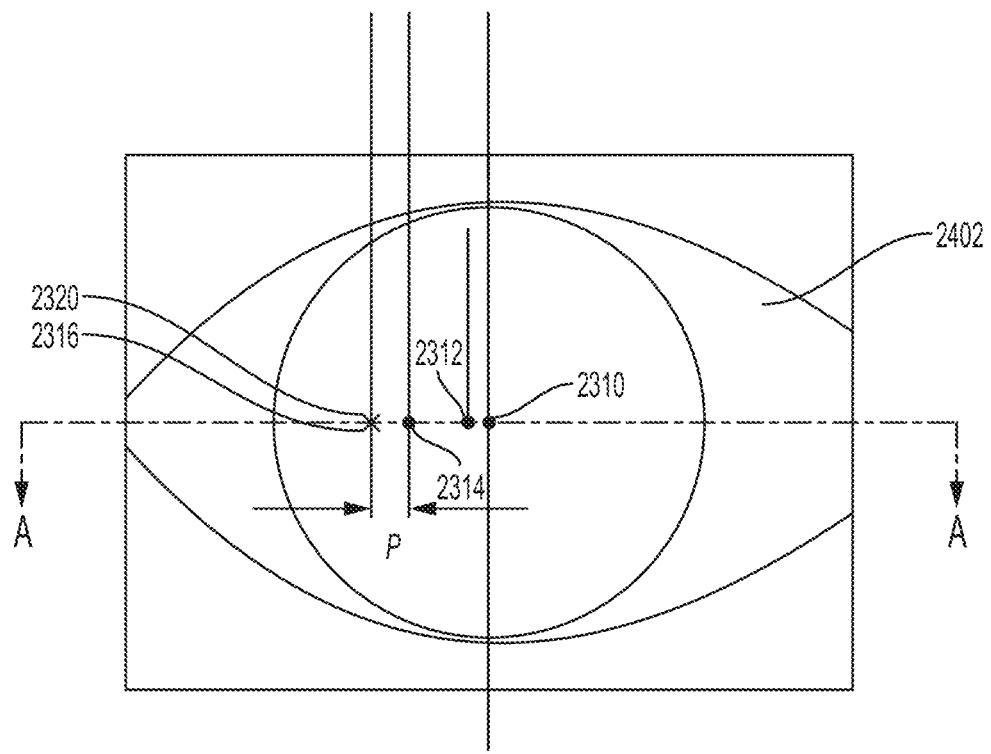

U.S. Pat. No. 9,552,660, titled "IMAGING SYSTEM AND METHODS DISPLAYING A FUSED MULTIDIMENSIONAL RECONSTRUCTED IMAGE," (incorporated herein by reference) discloses how preoperative images and/or graphics are visually fused with a stereoscopic image. FIGS. 23 and 24 show diagrams that illustrate how spurious parallax causes digital graphics and/or images to lose accuracy when fused to a stereoscopic image. FIG. 24 shows a front view of a patient's eye 2402 and FIG. 23 shows a cross-sectional view of the eye along plane A-A of FIG. 24. In FIG. 23, the information processor module 1408 is instructed to determine a caudal distance d from a focus plane 2302 to, for example, an object of interest 2304 on a posterior capsule of the eye 2402. The information processor module 1408 operates a program 1560 that specifies, for example, that the distance d is determined by a triangulation calculation of image data from the left and right views of the eye 2402. A view 2306 is shown from a perspective of the left optical image sensor 748 and a view 2308 is shown from a perspective of the right optical image sensor 746. The left and right views 2306 and 2308 are assumed to be coincident with an anterior center 2310 of the eye 2402. In addition, the left and right views 2306 and 2308 are two-dimensional views of the object 2304 projected onto a focal plane 2302 as theoretical right projection 2312 and theoretical left projection 2314. In this example, processor 1562 determines the distance d to the object of interest 2304 by calculating an intersection of an extrapolation of the theoretical right projection 2312 and an extrapolation of the theoretical left projection 2314 using a triangulation routine.

However, in this example spurious parallax exists, which causes an actual left projection 2316 to be located to the left of the theoretical left projection 2314 by a distance P, as shown in FIGS. 23 and 24. The processor 1562 uses the actual left projection 2316 and the right projection 2312 to determine a distance to an intersection 2320 of an extrapolation of the right projection 2312 and an extrapolation of the actual left projection 2316 using the triangulation routine. The distance of the intersection point 2320 is equal to the distance d plus an error distance e. The spurious parallax accordingly results in an erroneous distance calculation using data taken from a stereoscopic image. As shown in FIGS. 23 and 24, even a small degree of spurious parallax may create a significant error. In the context of a fused image, the erroneous distance may result in an inaccurate placement of a tumor three-dimensional visualization for fusion with a stereoscopic image. The inaccurate placement may delay the surgery, hinder the performance of the surgeon, or cause the entire visualization system to be disregarded. Worse yet, a surgeon may rely on the inaccurate placement of the tumor image and make a mistake during the microsurgery procedure.

D. The Example Stereoscopic Visualization Camera Reduces or Eliminates Spurious Parallax The example stereoscopic visualization camera 300 of FIGS. 3 to 16 is configured to reduce or eliminate visual defects, spurious parallax, and/or misaligned optical paths that typically result in spurious parallax. In some examples, the stereoscopic visualization camera 300 reduces or eliminates spurious parallax by aligning ZRPs of the left and right optical paths to the respective centers of pixel sets 1006 and 1008 of the right and left optical image sensors 746 and 748. Additionally or alternatively, the stereoscopic visualization camera 300 may align the optical paths of the left and right images. It should be appreciated that the stereoscopic visualization camera 300 may perform actions to reduce spurious parallax during calibration. Additionally, the stereoscopic visualization camera 300 may reduce detected spurious parallax in real-time during use.

Figure 25:
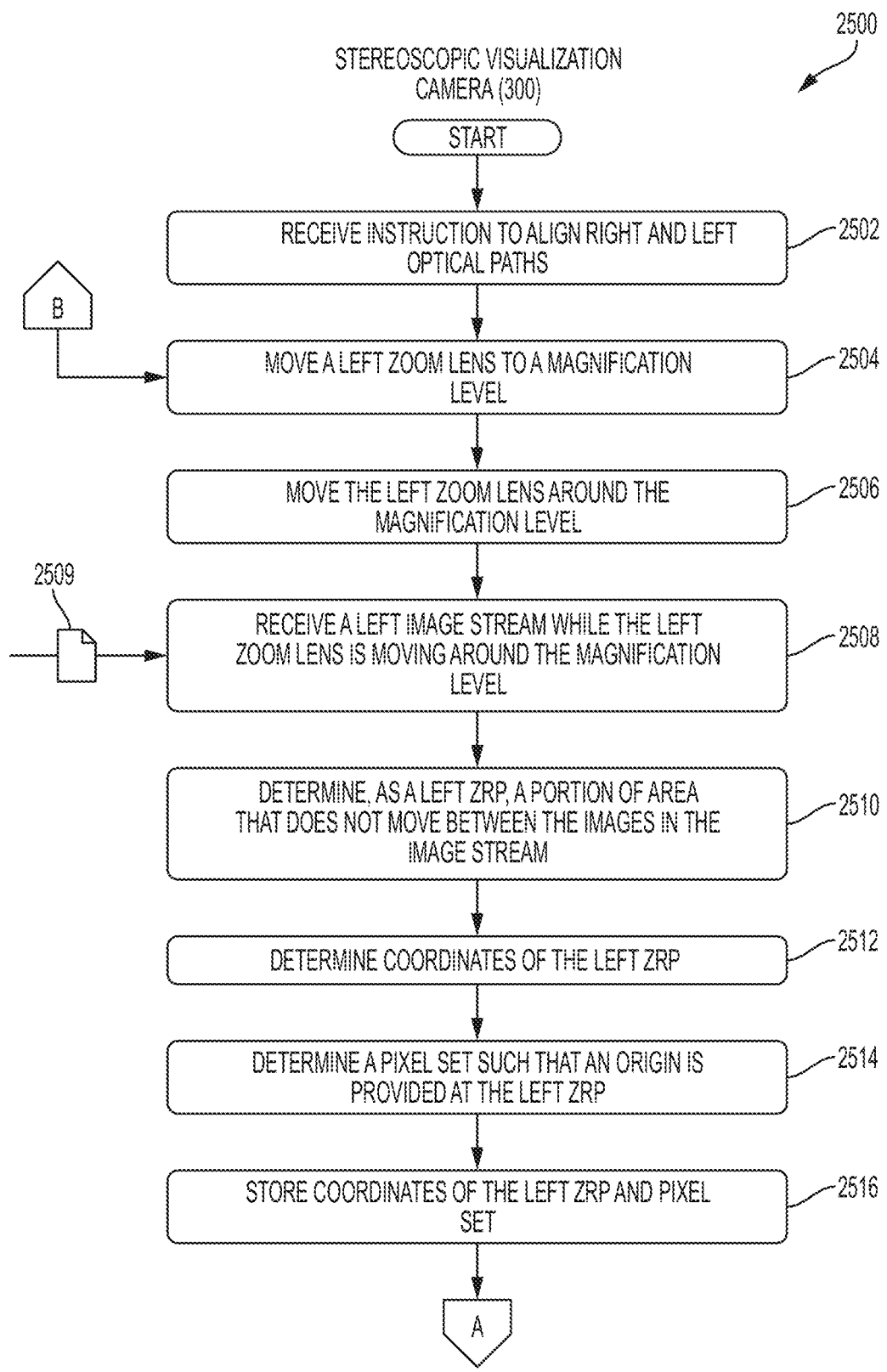
FIGS. 25 and 26 illustrate a flow diagram showing an example procedure to reduce or eliminate spurious parallax, according to an example embodiment of the present disclosure.
Figure 26:
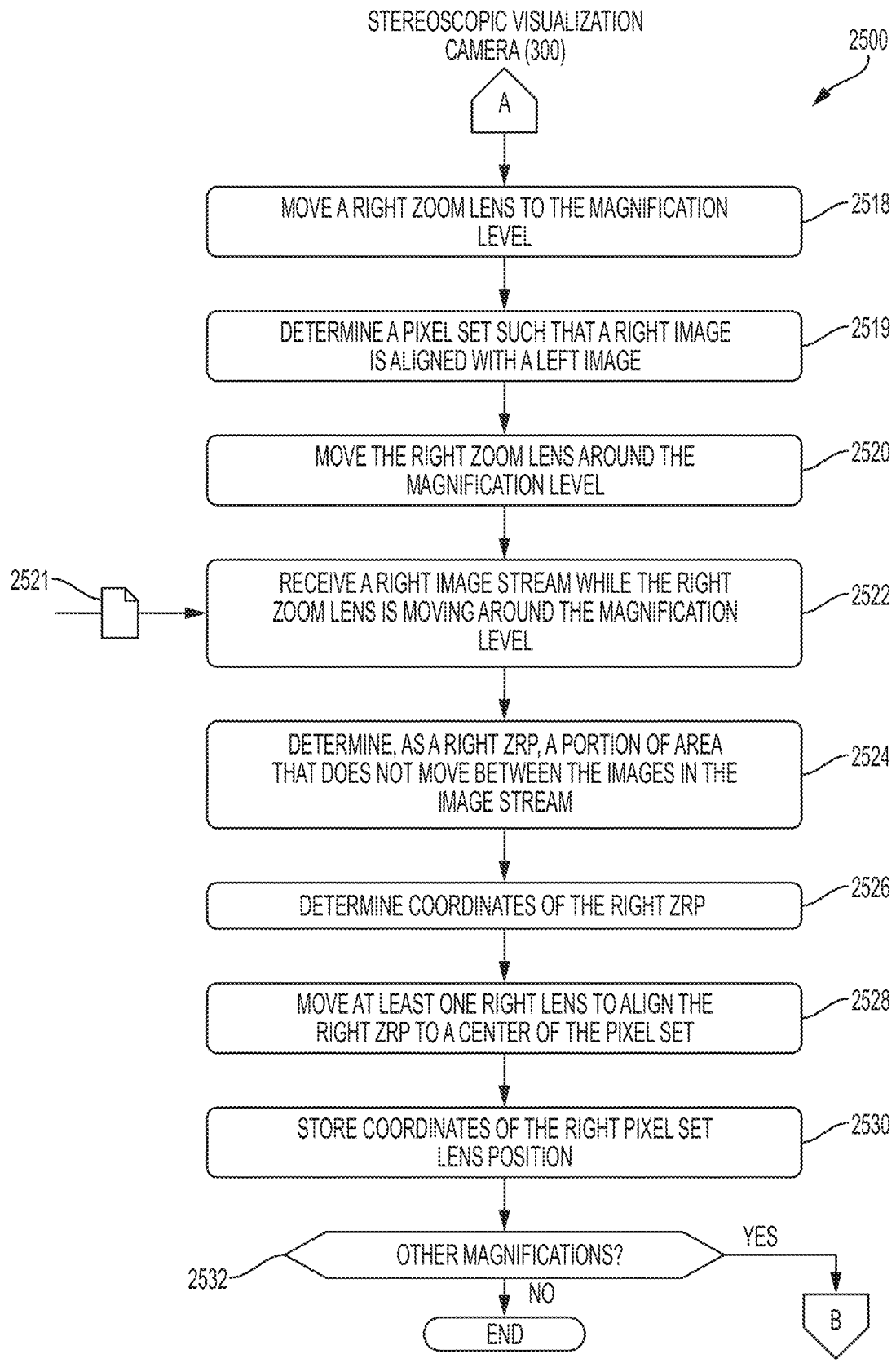

FIGS. 25 and 26 illustrate a flow diagram showing an example procedure 2500 to reduce or eliminate spurious parallax, according to an example embodiment of the present disclosure. Although the procedure 2500 is described with reference to the flow diagram illustrated in FIGS. 25 and 26, it should be appreciated that many other methods of performing the steps associated with the procedure 2500 may be used. For example, the order of many of the blocks may be changed, certain blocks may be combined with other blocks, and many of the blocks described are optional. Further, the actions described in procedure 2500 may be performed among multiple devices including, for example the optical elements 1402, the image capture module 1404, the motor and lighting module 1406, and/or the information processor module 1408 of the example stereoscopic visualization camera 300. For example, the procedure 2500 may be performed by one of the programs 1560 of the information processor module 1408.

The example procedure 2500 begins when the stereoscopic visualization camera 300 receives an instruction to align right and left optical paths (block 2502). The instructions may be received from the user input device 1410 in response to an operator requesting that the stereoscopic visualization camera 300 perform a calibration routine. In other examples, the instructions may be received from the information processor module 1408 after determining right and left images are misaligned. The information processor module 1408 may determine images are not aligned by executing a program 1560 that overlays right and left images and determines differences in pixel values, where greater differences over large areas of pixels are indicative of misaligned images. In some examples, the program 1560 may compare the pixel data of the left and right images without performing an overlay function, where, for example, left pixel data is subtracted from right pixel data to determine a severity of misalignment.

After receiving instructions to reduce spurious parallax, the example stereoscopic visualization camera 300 locates a ZRP of one of the left or right optical path. For illustrative purposes, procedure 2500 includes the ZRP of the left optical path being determined first. However, in other embodiments, the procedure 2500 may determine the ZRP of the right optical path first. To determine the left ZRP, the stereoscopic visualization camera 300 moves at least one zoom lens (e.g., the left front zoom lens 728 and/or the left rear zoom lens 734) to a first magnification level along a z-direction of the left optical path (block 2504). In instances where the front zoom lenses 726 and 728 are connected to the same carrier 724 and the rear zoom lenses 732 and 734 are connected to the same carrier 730, the movement of the left lenses causes the right lenses to also move. However, only movement of the left lenses is considered during this section of the procedure 2500.

At the first magnification level, the stereoscopic visualization camera 300 causes the left zoom lens to move along the z-direction (block 2506). The movement may include, for example, back-and-forth movement around the first magnification level. For example, if the first magnification level is 5×, the movement may be between 4× and 6×. The movement may also include movement in one direction, such as from 5× to 4×. During this movement, the stereoscopic visualization camera 300 may adjust one or more other lenses to maintain focus of the target site 700. At block 2508, during the movement of the left zoom lens, the stereoscopic visualization camera 300 records a stream or a sequence of images and/or frames 2509 of the target site 700 using, for example, the left optical image sensor 748. The images 2509 are recorded using an oversized pixel set 1008 configured to encompass an origin of the pixel grid 1004 and potential locations of the left ZRP.

The example processor 1562 of the information processor module 1408 analyzes the image stream to locate a portion of area that does not move in an x-direction or a y-direction between the images (block 2510). The portion of the area may include one or a few pixels and corresponds to the left ZRP. As discussed above, during a magnification change, objects move away from the ZRP or move towards the ZRP. Only objects at the ZRP remain constant in position with respect to the field-of-view as magnification changes. The processor 1562 may calculate deltas between the stream of images for each pixel using pixel data. An area with the smallest delta across the image stream corresponds to the left ZRP.

The example processor 1562 of the information processor module 1408 next determines coordinates of a portion of the area that does not move between the image stream (e.g., determines a location of the left ZRP) with respect to the pixel grid 1004 (block 2512). In other examples, the processor 1562 of the information processor module 1408 determines a distance between the origin and the portion of the area corresponding to the left ZRP. The distance is used to determine a position of the left ZRP on the pixel grid 1004. Once the location of the left ZRP is determined, the processor 1562 of the information processor module 1408 determines a pixel set (e.g., the pixel set 1008) for the left optical image sensor 748 such that the left ZRP is located at a center (within one pixel) of the pixel set (block 2514). At this point, the left ZRP is centered within the left optical path.

In some examples, blocks 2504 to 2514 may be performed iteratively by re-selecting the pixel set until the left ZRP is within a pixel of the origin and spurious parallax is minimized. After the pixel grid is determined, the processor 1562 of the information processor module 1408 stores at least one of coordinates of the pixel set and/or coordinates of the left ZRP to the memory 1570 as a calibration point (block 2516). The processor 1562 of the information processor module 1408 may associate the first magnification level with the calibration point such that the same pixel set is selected when the stereoscopic visualization camera 300 returns to the first magnification level.

Figure 27:
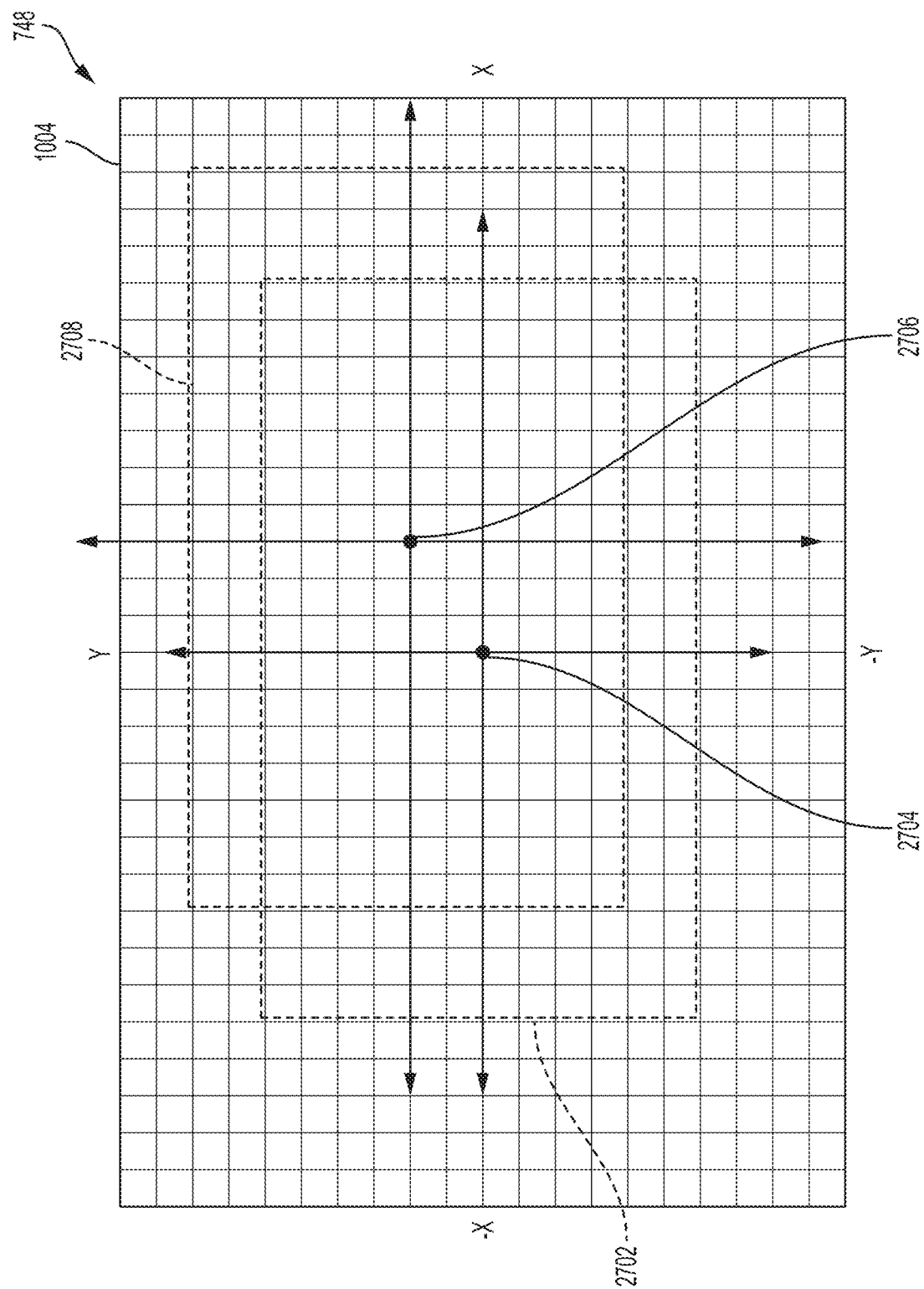
FIG. 27 shows a diagram illustrative of how a zoom repeat point is adjusted with respect to a pixel grid of an optical image sensor, according to an example embodiment of the present disclosure.

FIG. 27 shows a diagram illustrative of how the left ZRP is adjusted with respect to the pixel grid of the left optical image sensor 748. Initially, an initial (e.g., oversized) pixel set 2702 is selected, which is centered on origin 2704. The pixel set 2702 is large enough to record potential ZRPs in the image stream. In this illustrated example, a left ZRP 2706 is located above and to the right of the origin 2704. The processor 1562 of the information processor module 1408 determines pixel set 2708 based on a location of the left ZRP 2706 such that the left ZRP 2706 is located or positioned at a center of the pixel set 2708.

After the left ZRP is determined and aligned with an origin of a pixel set in FIG. 25, the example procedure 2500 aligns the left and right images in FIG. 26. To align the images, the example processor 1562 compares pixel data from left and right images recorded after the left ZRP is aligned with the origin. In some embodiments, the processor 1562 overlays the left and right images to determine differences using, for example, a subtraction and/or template method. The processor 1562 selects or determines a pixel set for the right optical path such that the resulting right images align or coincide with the left images (block 2519).

The example processor 1562, in the illustrated embodiment, determines the right ZRP. The steps are similar to steps discussed in blocks 2504 to 2512 for the left ZRP. For example, at block 2518 the stereoscopic visualization camera 300 moves a right zoom lens to the first magnification level. In some embodiments, the magnification level for the right lens is different than the magnification level used for determining the left ZRP. The example processor 1562 of the information processor module 1408 then moves the right zoom lens around the magnification level and receives a stream of images 2521 from the right optical image sensor 746 during the movement (blocks 2520 and 2522). The example processor 1562 of the information processor module 1408 determines the right ZRP from the right stream of images by locating a portion of an area that does not move between the images (block 2524). The processor 1562 next determines coordinates of the right ZRP and/or a distance between a center of an aligned pixel set 1006 to the right ZRP (block 2526).

The processor 1562 then instructs the motor and lighting module 1406 to move at least one lens in the right optical path in at least one of an x-direction, a y-direction, and/or a tilt-direction to align the right ZRP with the center of the aligned pixel set 1006 using, for example, the distance or coordinates of the right ZRP (block 2528). In other words, the right ZRP is moved to coincide with the center of the aligned pixel set 1006. In some examples, the right front lens 720, the right lens barrel 736, the right final optical element 745, and/or the right image sensor 746 is moved (using for example a flexure) in the x-direction, the y-direction and/or a tilt-direction with respect to the z-direction of the right optical path. The degree of movement is proportional to the distance of the right ZRP from the center of the pixel set 1006. In some embodiments, the processor 1562 digitally changes properties of the right front lens 720, the right lens barrel 736, and/or the right final optical element 745 to have the same effect as moving the lenses. The processor 1562 may repeat steps 2520 to 2528 and/or use subsequent right images to confirm the right ZRP is aligned with the center of the pixel set 1006 and/or to iteratively determine further lens movements needed to align the right ZRP with the center of the pixel set.

The example processor 1562 stores coordinates of the right pixel set and/or the right ZRP to the memory 1570 as a calibration point (block 2530). The processor 1562 may also store to the calibration point a position of the right lens that was moved to align the right ZRP. In some examples, the calibration point for the right optical path is stored with the calibration point for the left optical path in conjunction with the first magnification level. Thus, the processor 1562 applies the data within the calibration point to the optical image sensors 746 and 748 and/or radial positioning of one or more optical elements 1402 when the stereoscopic visualization camera 300 is subsequently set to the first magnification level.

In some examples, the procedure 2500 may be repeated for different magnification levels and/or working distances. Accordingly, the processor 1562 determines if ZRP calibration is needed for another magnification level or working distance (block 2532). If another magnification level is to be selected, the procedure 2500 returns to block 2504 in FIG. 25. However, if another magnification level is not needed, the example procedure ends.

Each of the calibration points may be stored in a look-up-table. Each row in the table may correspond to a different magnification level and/or working distance. Columns in the look-up-table may provide coordinates for the left ZRP, the right ZRP, the left pixel set, and/or the right pixel set. In addition, one or more columns may specify relevant positions (e.g., radial, rotational, tilt, and/or axial positions) of the lenses of the optical elements 1402 to achieve focus at the magnification level in addition to aligned right and left images.

The procedure 2500 accordingly results in the right ZRP and the left ZRP in addition to views of the target site to be aligned to pixel grids of the respective optical image sensors 746 and 748 as well as to each other in a three-dimensional stereoscopic image. In some instances, the left and right images and the corresponding ZRPs have an accuracy and alignment to within one pixel. Such accuracy may be observable on the display 514 or 514 by overlaying left and right views (e.g., images from the left and right optical paths) and observing both views with both eyes, rather than stereoscopically.

It should be appreciated that in some examples, a right pixel set is first selected such that the right ZRP is aligned with or coincident with an origin of the pixel set. Then, the right and left optical images may be aligned by moving one or more right and/or left lenses of the optical elements 1402. This alternative procedure still provides right and left ZRPs that are centered and aligned between each other and with respect to the optical image sensors 746 and 748.

The procedure 2500 ultimately reduces or eliminates spurious parallax in the stereoscopic visualization camera 300 throughout a full optical magnification range by ensuring left and right ZRPs remain aligned and the right and left images remain aligned. In other words, the dual optics of the right and left optical image sensors 746 and 748 are aligned such that parallax at a center of an image between the left and right optical paths is approximately zero at the focal plane. Additionally, the example stereoscopic visualization camera 300 is par focal across the magnification range, and par central across magnification and working distance ranges since the ZRP of each optical path has been aligned to a center of the respective pixel set. Accordingly, changing only the magnification will maintain a focus of the target site 700 in both optical image sensors 746 and 748 while being trained on the same center point.

The above procedure 2500 may be performed at calibration before a surgical procedure is performed and/or upon request by an operator. The example procedure 2500 may also be performed prior to image registration with a pre-operative microsurgical image and/or surgical guidance graphics. Further, the example procedure 2500 may be performed in real-time automatically during operation of the stereoscopic visualization camera 300.

1. Template Matching Example

Figure 28:
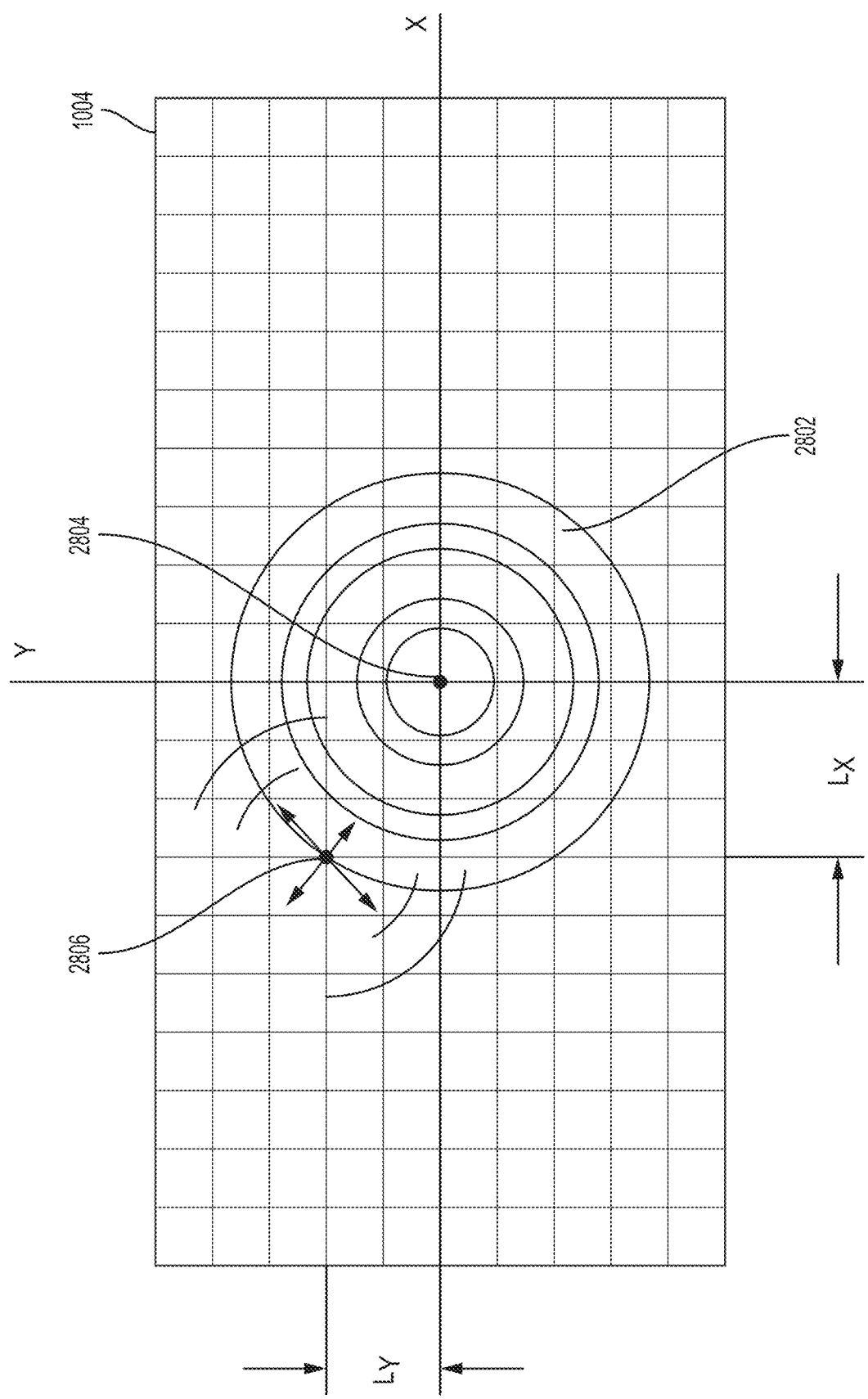
FIGS. 28 to 32 show diagrams illustrative of a template matching program to locate a zoom repeat point, according to an example embodiment of the present disclosure.

In some embodiments, the example processor 1562 of the information processor module 1408 is configured to use a program 1560 in conjunction with one or more templates to determine a position of the right ZRP and/or the left ZRP. FIG. 28 shows a diagram illustrative of how the processor 1562 uses a target template 2802 to determine a location of a left ZRP. In this example, FIG. 28 shows a first left image including the template 2802 aligned with an origin 2804 or center of the left pixel grid 1004 of the left optical image sensor 748. The template 2802 may be aligned by moving the stereoscopic visualization camera 300 to the appropriate location. Alternatively, the template 2802 may be moved at the target site 700 until aligned. In other examples, template 2802 may include another pattern that does not need alignment with a center of the pixel grid 1004. For example, the template may include a graphical wave pattern, a graphical spirograph pattern, a view of a surgical site of a patient and/or a grid having visually distinguishable features with some degree of non-periodicity in both the x and y-directions. The template is configured to prevent a subset of a periodic image from being perfectly aligned onto the larger image in a plurality of locations, which makes such templates unsuitable for matching. A template image that is suitable for template matching is known as a "template match-able" template image.

The template 2802 shown in FIG. 28 is imaged at a first magnification level. A left ZRP 2806 is shown with respect to the template 2802. The ZRP 2806 has coordinates of $L_x$, $L_y$ with respect to the origin 2804. However, at this point in time, the processor 1562 has not yet identified the left ZRP 2806.

Figure 29:
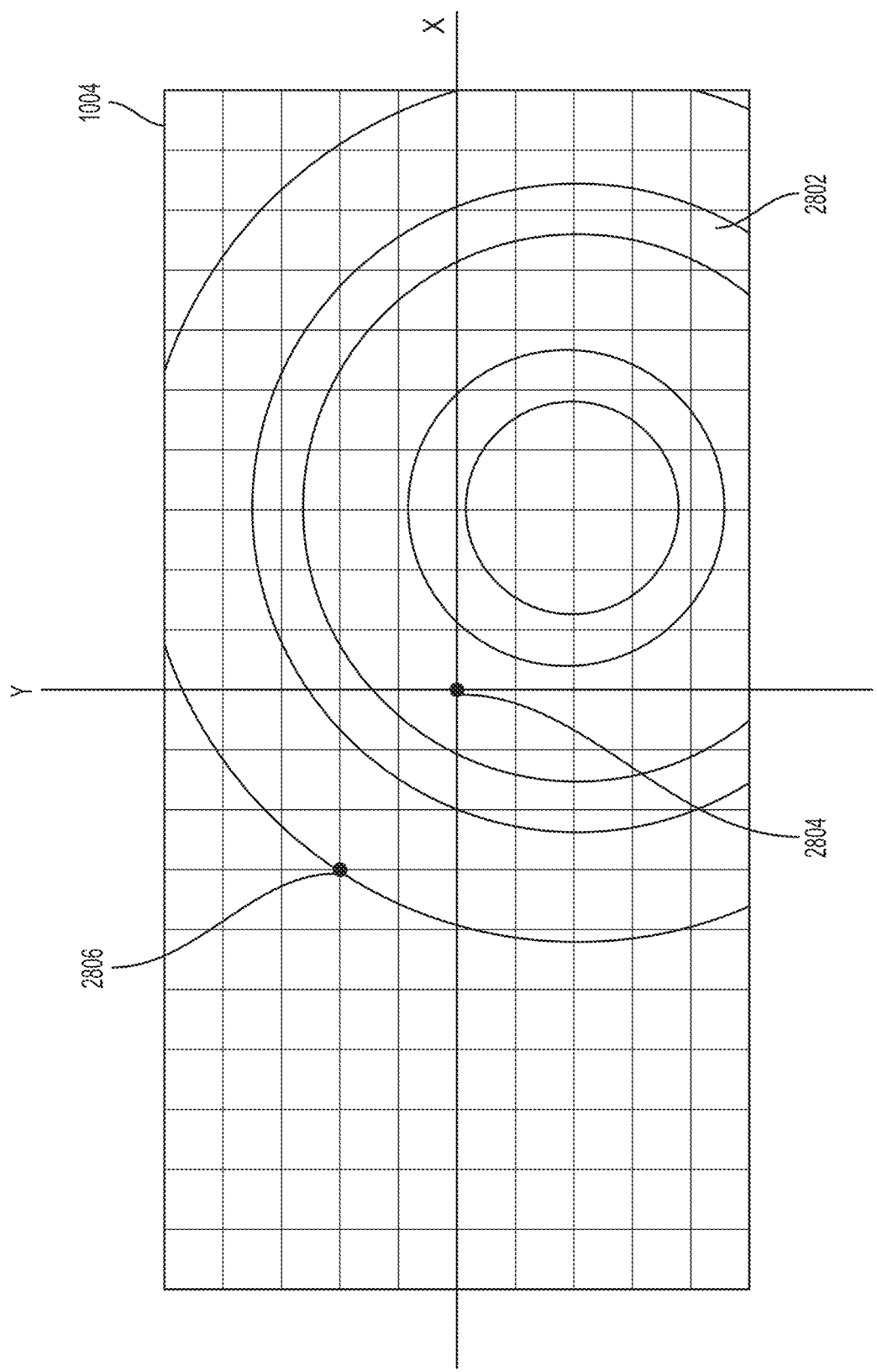

To locate the ZRP 2806, the processor 1562 causes a left zoom lens (e.g., the left front zoom lens 728 and/or the left rear zoom lens 734) to change magnification from the first magnification level to a second magnification level, specifically in this example, from 1× to 2×. FIG. 29 shows a diagram of a second left image including the target 2802 on the pixel grid 1004 with the magnification level doubled. From the first magnification level to the second magnification level, portions of the target 2802 increase in size and expand uniformly away from the left ZRP 2806, which remains stationary with respect to the first and second images. In addition, a distance between the origin 2804 of the pixel grid 1004 and the left ZRP 2806 remains the same.

Figure 30:
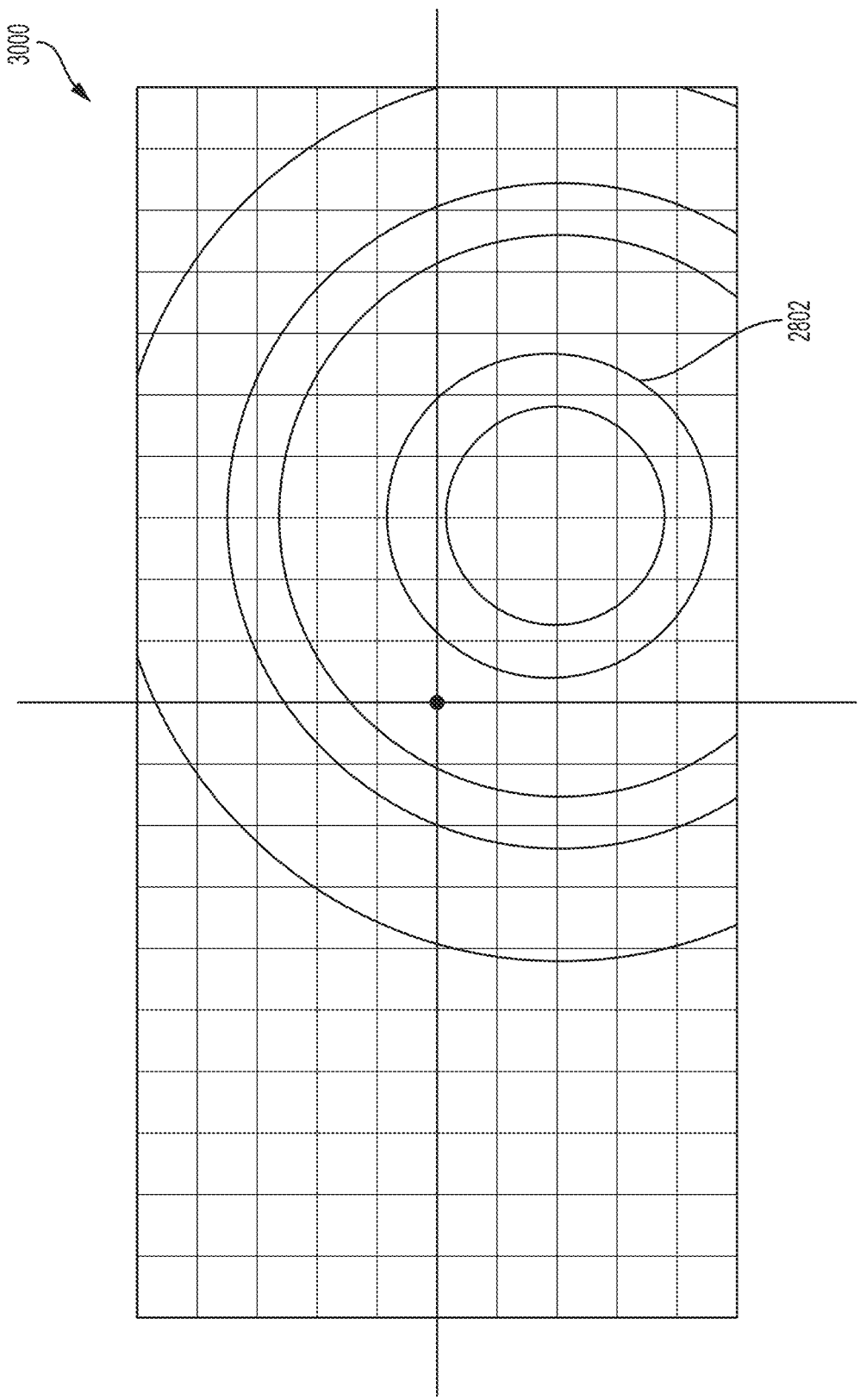

The example processor 1562 synthesizes a digital template image 3000 from the second image shown in FIG. 29. To create the digital template image, the processor 1562 copies the second image shown in FIG. 29 and scales the copied image by the reciprocal of the magnification change from the first to the second magnification. For example, if the magnification change from the first image to the second image was by a factor of 2, then the second image is scaled by ½. FIG. 30 shows a diagram of the digital template image 3000, which includes the template 2802. The template 2802 in the digital template image 3000 of FIG. 30 is scaled to be the same size as the template 2802 in the first left image shown in FIG. 28.

Figure 31:
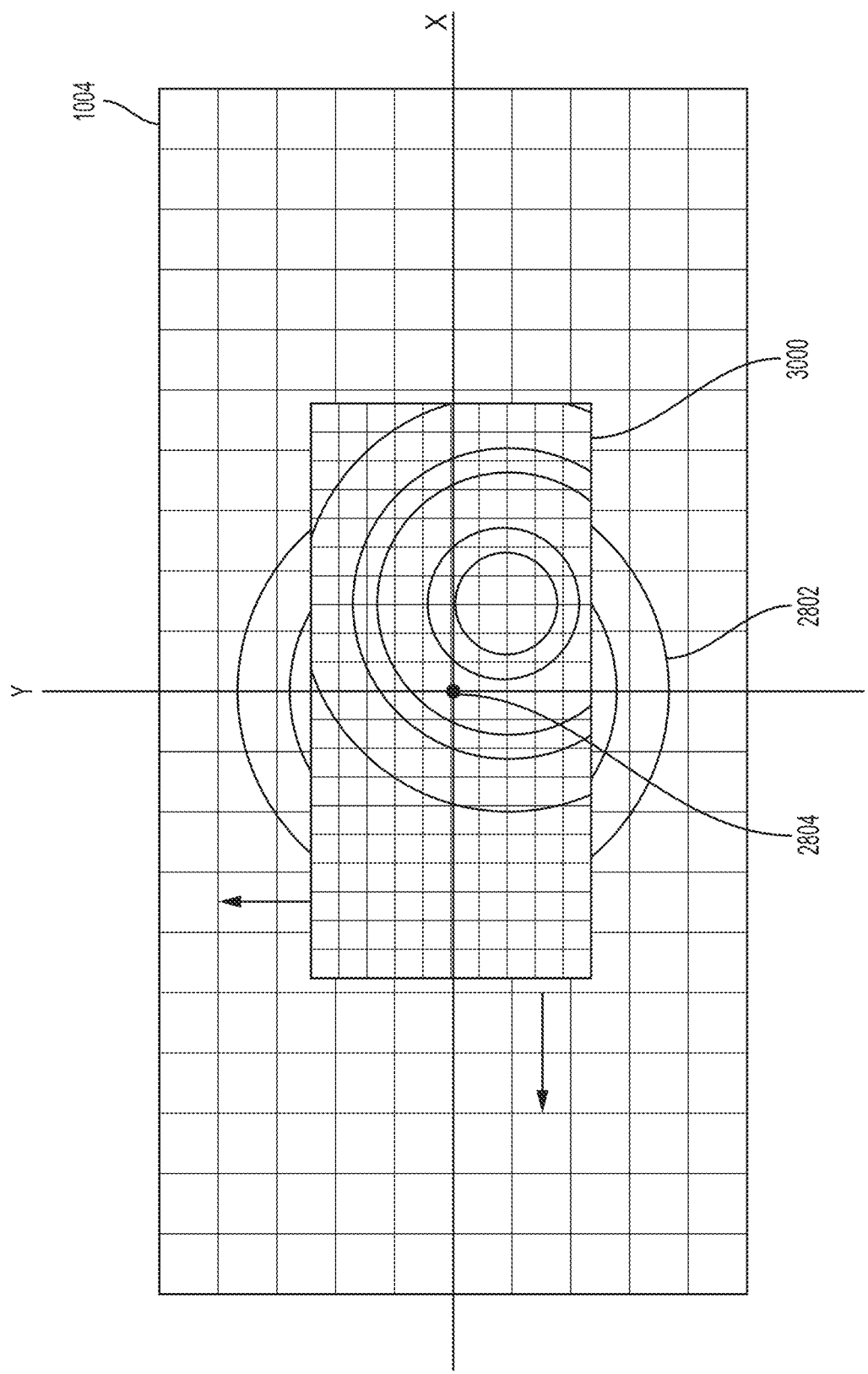

The example processor 1562 uses the digital template image 3000 to locate the left ZRP 2806. FIG. 31 shows a diagram that shows the digital template image 3000 superimposed on top of the first left image (or a subsequent left image recorded at the first magnification level) recorded in the pixel grid 1004. The combination of the digital template image 3000 with the first left image produces a resultant view, as illustrated in FIG. 31. Initially the digital template image 3000 is centered at the origin 2804 of the pixel grid 1004.

The example processor 1562 compares the digital template image 3000 to the underlying template 2802 to determine if they are aligned or matched. The example processor 1562 then moves the digital template image 3000 one or more pixels either horizontally or vertically and performs another comparison. The processor 1562 iteratively moves the digital template image 3000 compiling a matrix of metrics for each location regarding how close the digital template image 3000 matches the underlying template 2802. The processor 1562 selects the location in the matrix corresponding to the best matching metric. In some examples, the processor 1562 uses the OpenCV™ Template Match function.

Figure 32:
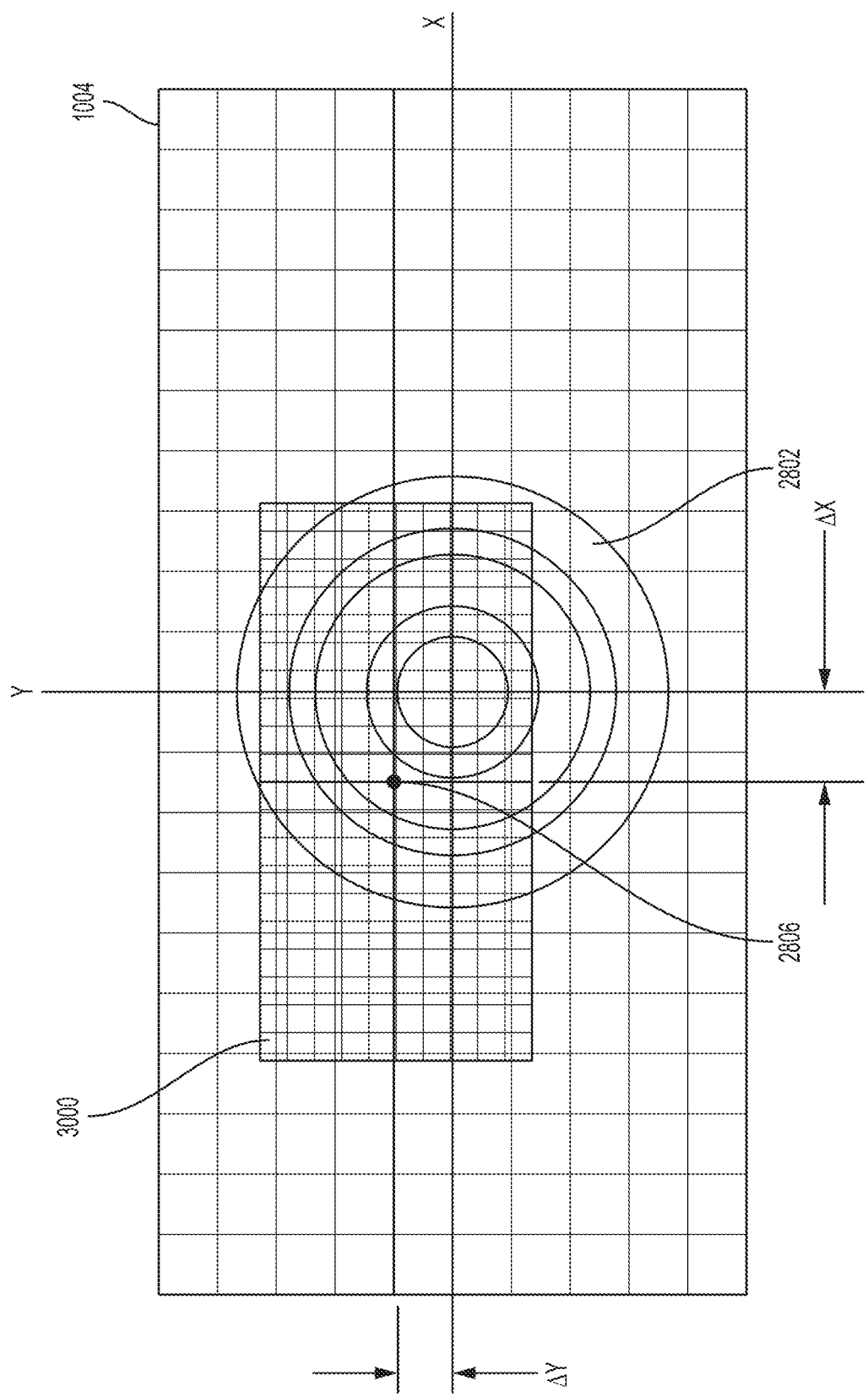

FIG. 32 shows a diagram with the digital template image 3000 aligned with the template 2802. The distance that the digital template image 3000 was moved to achieve optimal matching is shown as Δx and Δy. Knowing the digital template image 3000 was synthesized at a scale of M1/M2 (the first magnification level divided by the second magnification level), the processor 1562 determines the coordinates ($L_x$, $L_y$) of the left ZRP 2806 using Equations (1) and (2) below.

$$L_x = \Delta x/(M1/M2) \quad\quad \text{Equation (1)}$$

$$L_y = \Delta y/(M1/M2) \quad\quad \text{Equation (2)}$$

After the coordinates ($L_x$, $L_y$) of the left ZRP 2806 are determined, the example processor 1562 selects or determines a pixel subset with an origin that is aligned or coincides with the left ZRP 2806, as discussed above in conjunction with procedure 2500 of FIGS. 25 and 26. In some embodiments, the processor 1562 may use template matching iteratively to converge on a highly accurate ZRP position and/or pixel subset. Further, while the above example discussed locating the left ZRP, the same template matching procedure can be used to locate the right ZRP.

In some embodiments, the above-described template matching program 1560 may be used to align the left and right images. In these embodiments, left and right images are recorded at a magnification level. Both the images may include, for example, the target template 2802 of FIG. 28. A portion of the right image is selected and overlaid with the left image. The portion of the right image is then shifted around the left image by one or more pixels horizontally and/or vertically. The example processor 1562 performs a comparison at each location of the portion of the right image to determine how close a match exists with the left image. Once an optimal location is determined, a pixel set 1006 of the right pixel grid 1002 is determined such that the right image is generally coincident with the left image. The location of the pixel set 1006 may be determined based on how much the portion of the right image was moved to coincide with the left image. Specifically, the processor 1562 uses an amount of movement in the x-direction, the y-direction, and/or the tilt-direction to determine corresponding coordinates for the right pixel set 1006.

2. Right and Left Image Alignment Example

In some embodiments, the example processor 1562 of the information processor module 1408 of FIGS. 14 to 16 displays an overlay of right and left images on the display monitor 512 and/or 514. The processor 1562 is configured to receive user feedback for aligning the right and left images. In this example each pixel data for the right and left images is precisely mapped to a respective pixel of the display monitor 512 using, for example, the graphics processing unit 1564. The display of overlaid left and right images makes any spurious parallax readily apparent to an operator. Generally, with no spurious parallax, the left and right images should almost exactly align.

If an operator detects spurious parallax, the operator may actuate controls 305 or the user input device 1410 to move either the right or left image for alignment with the other of the right and left image. Instructions from the controls 305 may cause the processor 1562 to accordingly adjust the location of the left or right pixel set in real-time, such that subsequent images are displayed on the display monitor 512 reflective of the operator input. In other examples, the instructions may cause the processor 1562 to change a position of one or more of the optical elements 1402 via radial adjustment, rotational adjustment, axial adjustment, or tilting. The operator continues to provide input via controls 305 and/or the user input device 1410 until the left and right images are aligned. Upon receiving a confirmation instruction, the processor 1562 stores a calibration point to a look-up-table reflective of the image alignment at the set magnification level.

Additionally or alternatively, the template match method described above may be used to perform image alignment while focused on a planar target that is approximately orthogonal to a stereo optical axis of the stereoscopic visualization camera 300. Moreover, the template match method may be used to align the left and right views in real-time whenever a "template match-able" scene is in view of both the left and right optical paths. In an example, a template image is copied from a subset of, for instance, the left view, centered upon or near the center of the view. Sampling from the center for an in-focus image ensures that a similar view of the target site 700 will be present in the other view (in this example the right view). For out-of-focus images, this is not the case such that in the current embodiment this alignment method is performed only after a successful auto-focus operation. The selected template is then matched in the current view (or a copy thereof) of the other view (in this example the right view) and only a y-value is taken from the result. When the views are aligned vertically, the y-value of the template match is at or near zero pixels. A non-zero y-value indicates vertical misalignment between the two views and a correction using the same value of y is applied either to select the pixel readout set of the first view or a correction using the negated value of y is applied to the pixel readout set of the other view. Alternatively, the correction can be applied in other portions of the visualization pipeline, or split between pixel readout set(s) and said pipeline.

In some examples, the operator may also manually align a right ZRP with an origin of the pixel grid 1002. For instance, after determining a location of the right ZRP, the processor 1562 (and/or the peripheral input unit interface 1574 or graphics processing unit 1564) causes the right ZRP to be highlighted graphically on a right image displayed by the display monitor 512. The processor 1562 may also display a graphic indicative of the origin of the pixel grid 1002. The operator uses controls 305 and/or the user input device 1410 to steer the right ZRP to the origin. The processor 1562 uses instructions from the controls 305 and/or the user input device 1410 to accordingly move one or more of the optical elements 1402. The processor 1562 may provide a stream of right images in real-time in addition to graphically displaying the current location of the right ZRP and origin to provide the operator updated feedback regarding positioning. The operator continues to provide input via controls 305 and/or the user input device 1410 until the right ZRP is aligned. Upon receiving a confirmation instruction, the processor 1562 stores a calibration point to a look-up-table reflective of positions of the optical elements 1402 at the set magnification level.

3. Comparison of Alignment Error

The example stereoscopic visualization camera 300 produces less alignment error between right and left images compared to known digital surgical microscopes with stereoscopic cameras. The analysis discussed below compares spurious parallax generated by ZRP misalignment for a known digital surgical microscope with camera and the example stereoscopic visualization camera 300. Initially, both cameras are set at a first magnification level with a focal plane positioned on a first position of a patient's eye. Equation (3) below is used to determine working distance ("WD") from each camera to the eye.

$$WD = (IPD/2)/\tan(\alpha) \qquad \text{Equation (3)}$$

In this equation, IPD corresponds to the interpupillary distance, which is approximately 23 mm. In addition, α is one-half of an angle between, for example, the right optical image sensor 746 and the left optical image sensor 748, which is 2.50° in this example. The convergence angle is two times this angle, which is 5°, in this example. The resulting working distance is 263.39 mm.

The cameras are zoomed in to a second magnification level and triangulated on a second position of the patient's eye. In this example the second position is at the same physical distance from the camera as the first position, but presented at the second magnification level. The change in magnification generates spurious horizontal parallax due to misalignment of one or both of the ZRPs with respect to a center of a sensor pixel grid. For the known camera system, the spurious parallax is determined to be, for example, 3 arc-minutes, which corresponds to 0.05°. In Equation (3) above, the 0.05° value is added to α, which produces a working distance of 258.22 mm. The difference in working distance is 5.17 mm (263.39 mm-258.22 mm), which corresponds to the error of the known digital surgical microscope with camera attachment.

In contrast, the example stereoscopic visualization camera 300 is capable of automatically aligning ZRPs to be within one pixel of a center of a pixel set or grid. If the angular field-of-view is 5° and recorded with a 4k image sensor used in conjunction with a 4k display monitor, the one pixel accuracy corresponds to 0.00125° (5°/4000) or 4.5 arc-seconds. Using Equation (3) above, the 0.00125° value is added to α, which produces a working distance of 263.25 mm. The difference in working distance for the stereoscopic visualization camera 300 is 0.14 mm (263.39 mm-263.25 mm). When compared to the 5.17 mm error of the known digital surgical microscope, the example stereoscopic visualization camera 300 reduces alignment error by 97.5%.

In some embodiments, the stereoscopic visualization camera 300 may be more accurate at higher resolutions. In the example above, the resolution is about 4.5 arc-seconds for a 5° field-of-view. For an 8K ultra-high definition system (with 8000 pixels in each of 4000 rows) with a field-of-view of 2°, the resolution of the stereoscopic visualization camera 300 is approximately 1 arc-second. This means that ZRP of the left and right views may be aligned to one pixel or 1 arc-second. This is significantly more precise than known digital microscope systems that have spurious parallax on the order of arc-minutes.

4. Reduction of Other Sources of Spurious Parallax

The above-examples discuss how the example stereoscopic visualization camera 300 reduces spurious parallax as a result of misaligned ZRPs and/or left and right images themselves. The stereoscopic visualization camera 300 may also be configured to reduce other sources of spurious parallax. For example, the stereoscopic visualization camera 300 may reduce spurious parallax due to motion by simultaneously clocking the right and left optical image sensors 746 and 748 to record images at substantially the same instant.

The example stereoscopic visualization camera 300 may also reduce spurious parallax due to dissimilar magnification between the left and right optical paths. For example, the stereoscopic visualization camera 300 may set the magnification level based on the left optical path. The stereoscopic visualization camera 300 may then make automatic adjustments so that the magnification of the right image matches the left. The processor 1562, for example, may use image data to calculate control parameters, for example by measuring a number of pixels between certain features common in the left and right images. The processor 1562 may then equalize the magnification levels of the left and right images by digital scaling, inserting interpolative pixels, and/or deleting extraneous pixels. The example processor 1562 and/or the graphics processing unit 1564 may re-render the right image such that the magnification is matched to the left image. Additionally or alternatively, the stereoscopic visualization camera 300 may include independent adjustment of the left and right optical elements 1402. The processor 1562 may separately control the left and right optical elements 1402 to achieve the same magnification. In some examples, the processor 1562 may first set, for example, the left magnification level then separately adjust the right optical elements 1402 to achieve the same magnification level.

The example stereoscopic visualization camera 300 may further reduce spurious parallax due to dissimilar focus. In an example, the processor 1562 may execute a program 1560 that determines a best focus for each optical path for a given magnification and/or working distance. The processor 1562 first performs a focusing of the optical elements 1402 at a point of best resolution. The processor 1562 may then check the OOF condition at a suitable non-object-plane location and match the focus for the left and right images. The processor 1562 next re-checks the focus at best resolution and adjusts the focus iteratively until both left and right optical elements 1402 focus equally well both on and away from an object plane.

The example processor 1562 may measure and verify optimal focus by monitoring a signal relating to the focus of one or both of the right and left images. For example, a "sharpness" signal is generated by the graphics processing unit 1564 for the left and right images simultaneously and/or in synchronization. The signal changes as focus changes and may be determined from an image-analysis program, an edge detection analysis program, a bandwidth of Fourier transforms of pattern intensity program, and/or a modulation transfer function ("MTF") measurement program. The processor 1562 adjusts a focus of the optical elements 1402 while monitoring for a maximum signal indicative of a sharp image.

To optimize the OOF condition, the processor 1562 may monitor sharpness signals for both the left and right images. If the focus is moved off of the object plane and the signal related to, for example, the left image increases but the signal related to the right image decreases, the processor 1562 is configured to determine the optical elements 1402 are moving out of focus. However, if the signals related to both the right and left images are relatively high and approximately equal, the processor 1562 is configured to determine the optical elements 1402 are properly positioned for focusing.

5. Benefits of Low Spurious Parallax

The example stereoscopic visualization camera 300 has a number of advantages over known digital surgical microscopes as a result of the low spurious parallax between right and left images. For example, almost perfectly aligned left and right images produce an almost perfect stereoscopic display for a surgeon, thereby reducing eye fatigue. This allows the stereoscopic visualization camera 300 to be used as an extension of a surgeon's eyes rather than a cumbersome tool.

In another example, precisely aligned left and right images allow accurate measurements of the surgical site to be digitally taken. For instance, a size of a patient's ocular lens capsule may be measured such that a properly-sized IOL can be determined and accurately implanted. In another instance, a motion of a moving blood vessel may be measured such that an infrared fluorescein overlay can be accurately placed in a fused image. Here, the actual motion velocity is generally not of interest to the surgeon but critical for the placement and real-time adjustment of the overlaid image. Properly matched scale, registration, and perspective of the overlaid images are all important to provide an accurately-fused combined live stereoscopic image and an alternate-mode image.

In some examples, the processor 1562 may enable an operator to draw measurement parameters on the display monitor 512. The processor 1562 receives the drawn coordinates on a screen and accordingly translates the coordinates to the stereoscopic image. The processor 1562 may determine measurement values by scaling the drawn ruler on the display monitor 512 to a magnification level shown in the stereoscopic images. The measurements made by the processor 1562 include point-to-point measurements of two or three locations displayed in the stereoscopic display, point-to-surface measurements, surface characterization measurements, volume determination measurements, velocity verification measurements, coordinate transformations, instrument and/or tissue tracking, etc.

VII. Fluorescence Visualization Embodiment

As discussed above in connection with FIGS. 7, 8, 14, and 15 the example stereoscopic visualization camera 300 includes one or more lighting sources including a visible light source 708a, a near-infrared ("NIR") light source 708b, and a near-ultraviolet ("NUV") light source 708c. The stereoscopic visualization camera 300 also includes a filter assembly 740 that can accommodate three different optical filter pairs. For example, the filter assembly 740 can include an infrared cut filter, a near-infrared bandpass filter, and a near-ultraviolet cut filter. The different filter types are selected to work with different spectra of the light sources 708 and the reflectivity and transmissivity characteristics of the deflecting element 712 to pass certain desired wavelengths of light at predetermined times. Synchronization between the light sources 708 and the filter 740 may be performed by the motor and lighting controller 1520 and/or the processor 1562 of FIG. 15.

In some examples, each of the light sources 708 may be provided by a single LED, two LEDs, three, LEDs, etc. The NUV light source 708c may include, for example, three 405 nm LEDs. The drivers 1534, 1536, and 1538 of FIG. 15 are configured to provide a constant current source and adjust light intensity via pulse width modulation. In some examples, each of the light sources 708 may consume nine watts of power, three watts for each LED.

Figure 33:
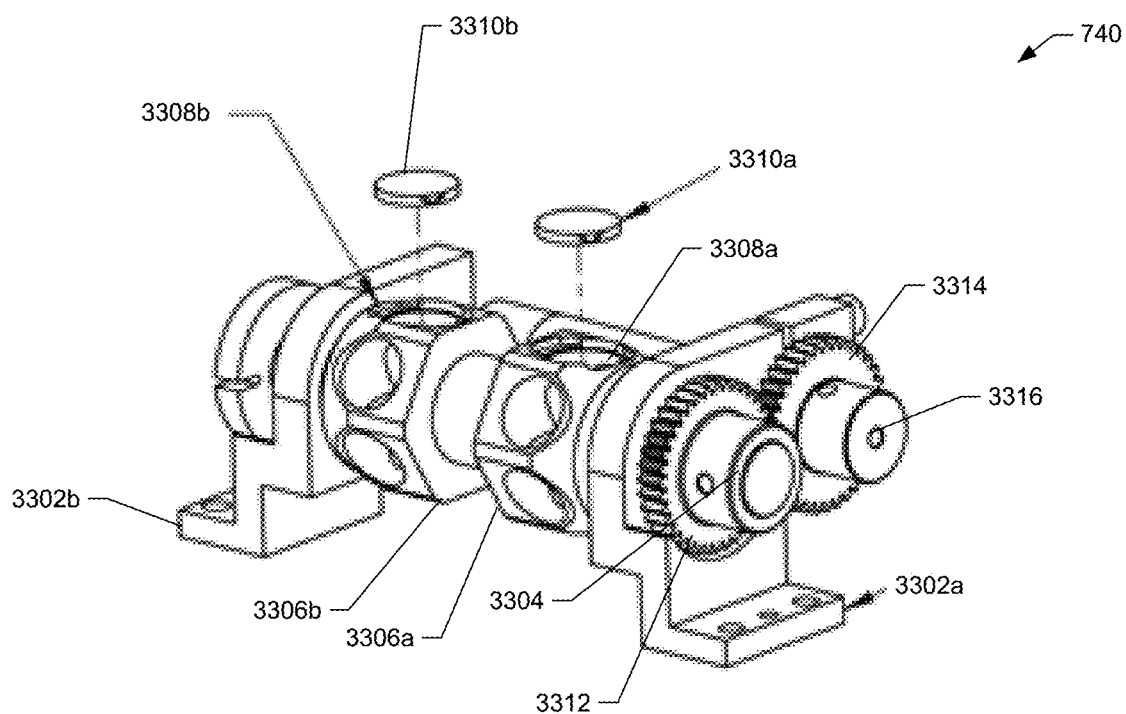
FIGS. 33 and 34 show diagrams of a filter assembly of FIGS. 7 and 8, according to example embodiments of the present disclosure.

FIG. 33 shows a diagram of the filter assembly 740 of FIGS. 7 and 8, according to an example embodiment of the present disclosure. The filter assembly 740 includes a first support section 3302a and a second support section 3302b. Each of the sections 3302 is configured to mechanically couple to the housing 302 or other internal structure of the stereoscopic visualization camera 300. The support sections 3302 are configured to retain an axle 3304 therebetween. A center portion of the axle 3304, located between the support sections 3302, is configured to include or support filter magazines 3306a and 3306b. In the illustrated example, a filter magazine 3306 is provided for each of the left and right optical paths. In other embodiments, a single filter magazine 3306 may be provided for both the left and right optical paths.

The example filter magazines 3306 are configured to connect to the axle 3304 at a center portion. The axle 3304 may be configured to pass through or be reflected around the center portion of the magazines 3306 while enabling light to pass through the assembly 740. In other examples, the axle 3304 does not pass through the filter magazines 3306 and instead is partitioned into pieces between the magazines 3306 and the support sections 3302. In these examples the filtered light passes through a center of the magazines 3306. In some embodiments, the filter magazines 3306 may be mechanically and/or chemically connected to the axle 3304. In other examples, the filter magazines 3306 may include one or more gaskets or other elastomeric couplers that provide for a secure connection with the axle 3304. Positioning of both of the filter magazines 3306 on the same axle 3304 enables both magazines 3306 to be rotated around a rotation axis at the same speed and in the same direction for the same duration. In other examples, the filter magazines 3306 may be connected to separate axles for individual rotation control.

As shown in FIG. 33, each of the filter magazines 3306 includes a plurality of windows configured to accept or secure in place a light filter. For example, window 3308a of the filter magazine 3306a is configured to hold or secure in place light filter 3310a, while window 3308b of the filter magazine 3306b is configured to hold or secure in place light filter 3310b. Each of the example filter magazines 3306 includes six sides for accepting six filters. The filters 3310 have a diameter between 5 mm and 20 mm, preferably around 9 mm. In other examples, the filter magazines 3306 may include fewer sides and filters or additional sides and filters. Each of the filters 3310 include a lens that is colored or coated such that only light of certain wavelengths may pass through. The filters 3310 enable, for example, light corresponding to fluorescence emission wavelengths to pass through while blocking non-emission wavelengths, including visible light.

The example filter magazines 3306 are arranged on the axle 3304 such that they are perfectly or substantially aligned. Each of the corresponding sides of the filter magazines are configured to have the same filter type such that the same filter type is applied to light in both the left and right optical paths. For example, each of the light filters 3310a and 3310b may either be an infrared cut filter, a near-infrared bandpass filter, or a near-ultraviolet cut filter.

In some examples, six light filters 3310 are provided at the respective six sides of the filter magazine 3306. The light filters may be aligned such that the filter magazine 3306 has a side with a light filter that receives light and an adjacent or opposing side of the same filter type. In instances where light passes through the filter magazine 3306 without deflection, parallel, opposing sides are provided light filters of the same type. Alternatively, a first side may have one of the filter types while the parallel, opposing side has a clear lens that does not provide light filtering. In some embodiments, the clear lens may be replaced with the left or right single optical element 745 or 747 of FIGS. 7 and 8. In these embodiments, filters of different types are placed adjacent to each other.

In instances where the filter magazine 3306 includes internal deflecting elements, the deflecting elements are configured to refract or deflect light that passes in one side of the magazine 3306 such that the light is propagated through an adjacent side of the magazine 3306. As such, filters of the same type may be placed adjacent to each other.

The example axle 3304 is rotated via a gear 3312, which is linked to a gear 3314 of a drive axle 3316. Rotation of the drive axle 3316 causes the gear 3314 to rotate, which causes the gear 3312 and corresponding axle 3304 to rotate in the same manner. The drive axle 3316 is mechanically coupled to a filter motor (not shown), which is controlled by the filter magazine motor driver 1540 of FIG. 15. The use of the drive axle 3316 prevents, for example, force or torque from a drive motor from providing force on the filter magazine 3306 and/or the corresponding light filters 3310. The motor is configured to rotate the filter magazines 3306 at a rate sufficient enough to enable 120 frames to be recorded per second by the image sensors 746 and 748. Each frame may require an 8.33 microsecond exposure time. In instances, where an image is created using visible light and fluorescence emission light, the motor provides quick rotational movement between two different filter positions, while dwelling at each position for 8.33 microseconds before changing positions again.

Figure 34:
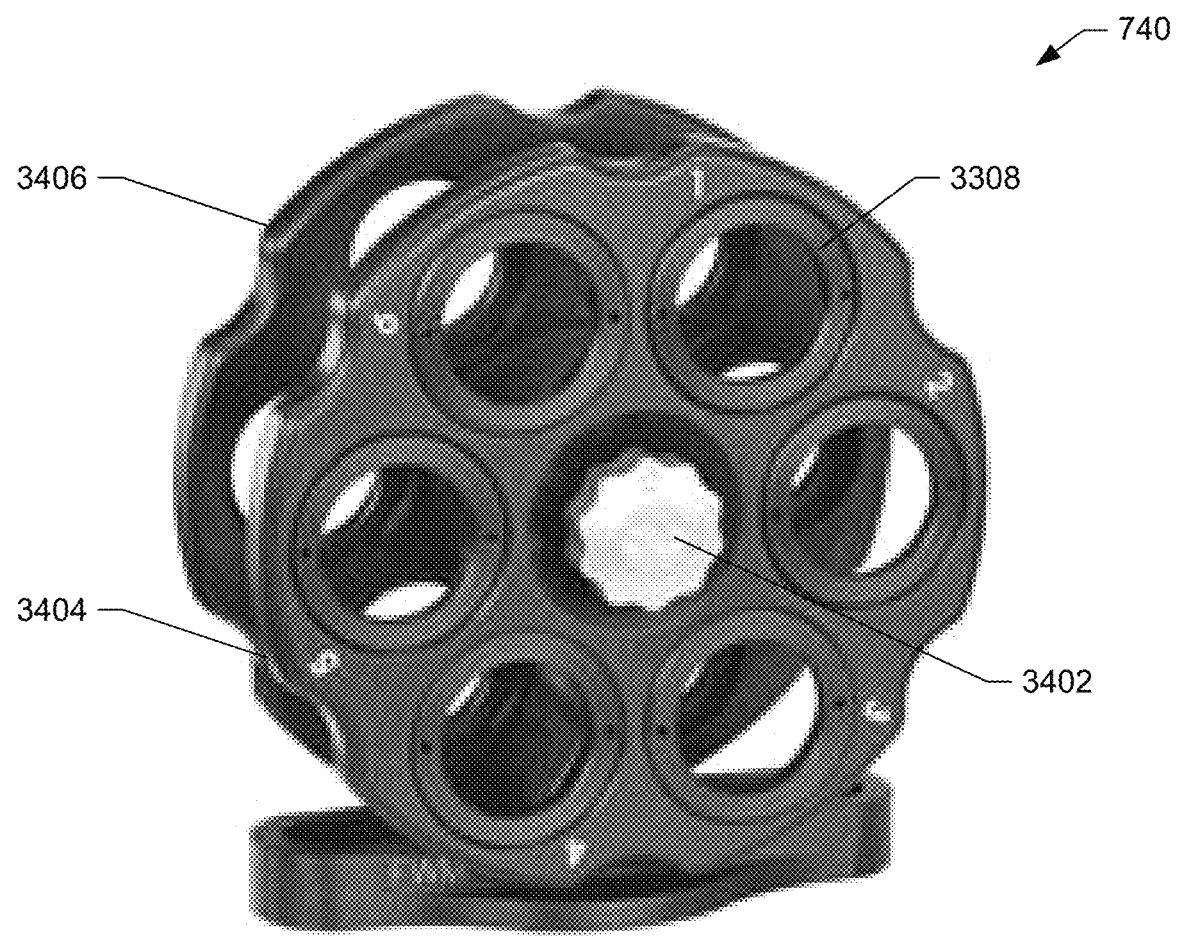

FIG. 34 shows another embodiment of the filter assembly 740 of FIGS. 7 and 8, according to an example embodiment of the present disclosure. The filter assembly 740 is shown as a wheel. In other embodiments, the filter assembly 740 may be configured as a ring or a turret. In the illustrated embodiment, the filter assembly 740 includes an axle 3402 directly connected to a motor. The filter assembly 740 also includes a first panel 3404 and a second panel 3406 that are parallel to each other. The axle 3402 is configured to pass through a center of the panels 3404 and 3406 to enable the panels to be rotated around an axis of rotation.

Each of the panels 3404 and 3406 include six windows 3308 to hold in place respective light filters. In addition, the panels 3404 and 3406 are separated from each other by a certain distance. In an embodiment, light filters may be placed in the windows 3308 of the first panel 3404 while clear lenses are placed in windows 3308 of the second panel 3406. In another embodiment, filters are placed in the windows 3308 of the first panel 3404 and the second panel 3406. The windows on the panels 3404 and 3406 are aligned to enable at least some light to pass through.

In some instances, the panels 3404 and 3406 are configured to receive light from both the left and right optical paths. For example, light from the left and right optical paths may be received at opposing windows of the same panel. In other instances, each of the left and right optical paths may have a separate filter assembly 740.

In other embodiments, the filter assembly 740 includes an optical directing device, such as movable mirrors. The directing device is configured to deflect light to one or more potential paths that each has a different light filter. The mirrors may be rotated or otherwise moved by respective motors or actuators. After filtering, the light is deflected to respective image sensors 746 and 748 and/or the final optical element set 742.

The following sections describe how the stereoscopic visualization camera 300 is configured to provide for different fluorescence modes by controlling activation of certain light sources 708 with one or more light filters of the filter assembly 740. While the disclosure is in reference to indocyanine green ("ICG") and 5-aminolevulinic acid ("ALA") fluorescence, it should be appreciated that that the stereoscopic visualization camera 300 may be configured for other types of fluorescence and/or lighting modes. For example, transmission wavelengths of the light sources 708 may be changed and/or the filter assembly 740 can be configured with different light filters to provide for different lighting modes.

A. Indocyanine Green ("ICG") Embodiment

ICG is a cyanine dye used to observe perfusion within a patient's body. In some instances, ICG may be used for performing angiography. Generally, ICG is useful for imaging or differentiating blood vessels from other tissue. ICG is used in medical applications as a result of its response to Near Infrared ("NIR") light when bonded to proteins in a patient's blood. The ICG absorbs light having wavelengths between 710 nm-822 nm, with peak absorption between 800-810 nm. Generally, light from a light source that provides light having a wavelength between 710 nm-822 nm causes the ICG (bonded to protein) to emit a light in the spectral range of 755 nm-880 nm, with a peak between 830 nm-832 nm. As such, photons from an excitation light source that have the same wavelength as the absorption wavelengths of ICG interact with the ICG, thereby causing the emission of light having a shifted wavelength.

Most humans cannot perceive light that has a wavelength above 700 nm. As a result, humans cannot view the emission of ICG fluorescence. Conventional known vision systems attempt to solve this problem by being sensitive in the NIR light spectrum. For instance, a conventional microscope uses a two-dimensional infrared camera, which is attached as an accessory. The known accessory cameras lack resolution and do not provide depth perception since they provide only two-dimensional video. The recorded video suffers from light loss since the camera is attached to an optical splitter, such as the splitter described in connection with FIG. 2. The loss of light makes it very difficult for a camera to visualize deep cavities. As a result of these limitations, accessory cameras may only have a working distance limit of 300 mm.

In an attempt to reduce the drawbacks, known conventional microscopes with accessory cameras tend to be large, heavy, and generate significant amounts of heat at the target surgical site, which is not ideal for the patient. The additional heat generated by increasing light intensity to compensate for the added camera and lack of depth perception often times causes surgical work on the patient to be paused during ICG excitation. Further, these systems tend to lose fluorescence visualization due to reduced resolution at magnification settings greater than 5× and are limited to smaller illumination field diameters resulting from less illumination power distribution over the surgical area. As a result of these deficiencies, many surgeons do not use conventional microscopes for ICG fluorescent visualization if it is not needed.

Figure 35:
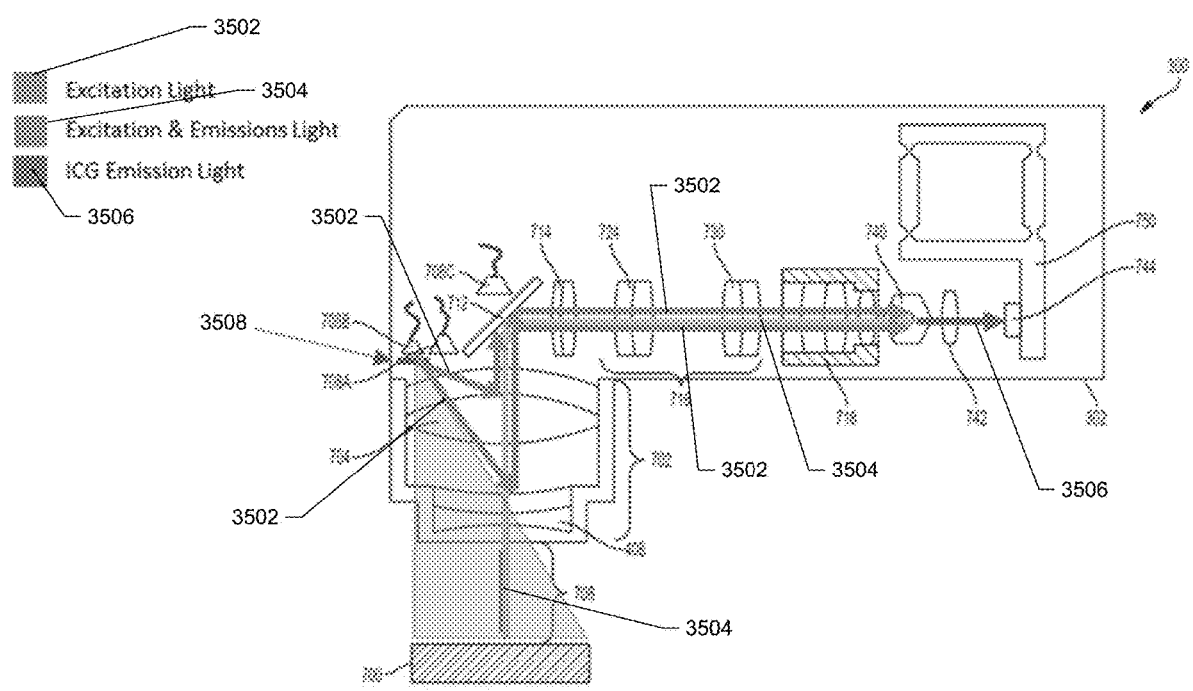
FIG. 35 shows a diagram illustrative of how the stereoscopic visualization camera of FIG. 3 uses a near-infrared ("NIR") light source with a filter assembly for providing light corresponding to indocyanine green ("ICG") emission wavelengths to image sensors, according to an example embodiment of the present disclosure.

The example stereoscopic visualization camera 300 disclosed herein overcomes at least some of the known problems of conventional microscopes by synchronizing light source activation and filter selection to optimize the reception of ICG emission light. FIG. 35 shows an embodiment illustrative of how the stereoscopic visualization camera 300 uses the NIR light source 708b with the filter assembly 740 for providing light corresponding to ICG emission wavelengths to the image sensors 746 and 748, according to an example embodiment of the present disclosure.

In the illustrated example, an operator selects an NIR mode of the stereoscopic visualization camera 300. The operator may select the NIR mode using controls on the arms 304 and/or via an input device 1410. The motor and lighting controller 1520 and/or the processor 1562 of FIG. 15 receives the request for NIR mode and transmits one or more messages or signals to the NIR light driver 1536 for activating the NIR light source 708b and/or the visible light driver 1538 to activate the visible light source 708a. The motor and lighting controller 1520 and/or the processor 1562 may also deactivate the other light sources 708a and/or 708c. In addition to activating the NIR light source 708b, the motor and lighting controller 1520 and/or the processor 1562 cause the filter assembly 740 to rotate the left and right filter magazines 3306 to cause near-infrared bandpass filters to be placed in the left and right optical paths.

In some embodiments, the motor and lighting controller 1520 and/or the processor 1562 use one or more zoom lookup tables to cause the front zoom lens set 724 and/or rear zoom lens set 730 to move along the optical path to maintain focus. The movement may be only a few microns to account for a different focal point (compared to visible light) as a result of longer wavelengths associated with infrared light. The zoom lookup table enables the same front zoom lens set 724 and/or rear zoom lens set 730 to be used for focusing both visible and IR light onto the image sensors 746 and 748 without having to move the image sensors further away to account for the wavelength differences. In some embodiments, the motor and lighting controller 1520 and/or the processor 1562 may also adjust a position of the front working distance lens 408 and/or the rear working distance lens 704 to improve focus for light in the IR spectrum. Additionally or alternatively, the motor and lighting controller 1520 and/or the processor 1562 may adjust settings of the image sensors 746 and 748 to improve sensitivity to light in the ICG wavelength range.

As shown in the illustrated example of FIG. 35, excitation light 3502 transmits through an excitation filter 3508 that is configured to remove a large percentage or portion of the excitation light that is within the same wavelength range as that of the emissions filter of the filter assembly 740. In other words, the excitation filter 3508 permits light between, for example 730 nm to 820 nm (or 738 nm to 802) nm to pass, corresponding to the absorption wavelength range of ICG, while blocking light having wavelengths above 802 nm or 820 nm (and below 730 nm in some embodiments) to prevent contamination with excitation light having a wavelength above 820 nm. As such, as shown in FIG. 35 any excitation light 3502 that propagates to the end of the optical path due to reflections in the main objective assembly 702 (or from the target surgical site 700, shown as exited and emissions light 3504) is blocked by the excitation filter (e.g., the near-infrared bandpass filter) of the filter assembly 740 so that only ICG emissions light 3506 (e.g., light having a wavelength between 817 nm to 900 nm) is received at the image sensors 746 and 748 (collectively optical image sensor 744).

It should be appreciated that the image sensors 746 and 748 of the stereoscopic visualization camera 300 have a greater resolution than IR-specific cameras used as accessories in conventional microscopes. The greater resolution of the image sensors 746 and 748 produces sharper images with move overall detail. Further, the use of left and right image sensors 746 and 748 provides three-dimensional images with depth, which enables a surgeon to safely maneuver instruments in the surgical area while viewing the video on the display monitor 512, 514. The use of single left and right optical paths eliminates the need for optical splitters of known microscopes, thereby decreasing system complexity, cost, and light loss. The maximization of light throughput to the image sensors 746 and 748 enables the stereoscopic visualization camera 300 to use less powerful illumination (e.g., 20 to 25 watts) compared to known microscopes, which use up to 400 watts and need to operate at 80% to 100% for proper fluorescence. The use of less light (and power generally) generates less heat at the surgical site, thereby reducing the risk of burning or overheating patient tissue, which reduces the amount of external hydration that needs to be applied to the surgical site.

It should also be appreciated that the light sources 708 of the stereoscopic visualization camera 300 are positioned relative to the main objective assembly 702 to provide semi-coaxial illumination, which increases the amount of light that can reach into deep cavities. As such, the example stereoscopic visualization camera 300 has little or no magnification or working distance restrictions and can visualize ICG fluorescence up to 10× or 20× through the entire working distance between 200 mm-450 mm. The stereoscopic visualization camera 300 provides a wide illumination field by default since the focusing is performed by the main objective assembly 702 and/or the zoom assembly 716 rather than in independent optics found in known conventional microscopes.

In some embodiments, the stereoscopic visualization camera 300 is configured to provide back-illumination using visible light while visualizing ICG emission light. In known conventional microscopes, when a surgeon is viewing ICG emission light, the surrounding areas that are not emitting light are completely dark, making it very difficult for the surgeon to introduce or move their instrument at the target surgical site. The stereoscopic visualization camera 300 may switch between the visible light source 708a and the NIR light source 708b while having the near-infrared bandpass filter of the filter assembly 740 engaged with the optical paths. The stereoscopic visualization camera 300 may alternatively activate the visible light source 708a at the same time as the NIR light source 708b. While the light sources 708a and 708b are activated, the image sensors 746 and 748 record the ICG emission light for stereoscopic display. In this manner, the addition of the visible spectrum light enables the surgeon to see surrounding tissue while still being able to view the fluorescing vascular system in real time via the stereoscopic visualization on the display monitor 512 and 514.

Figure 36:
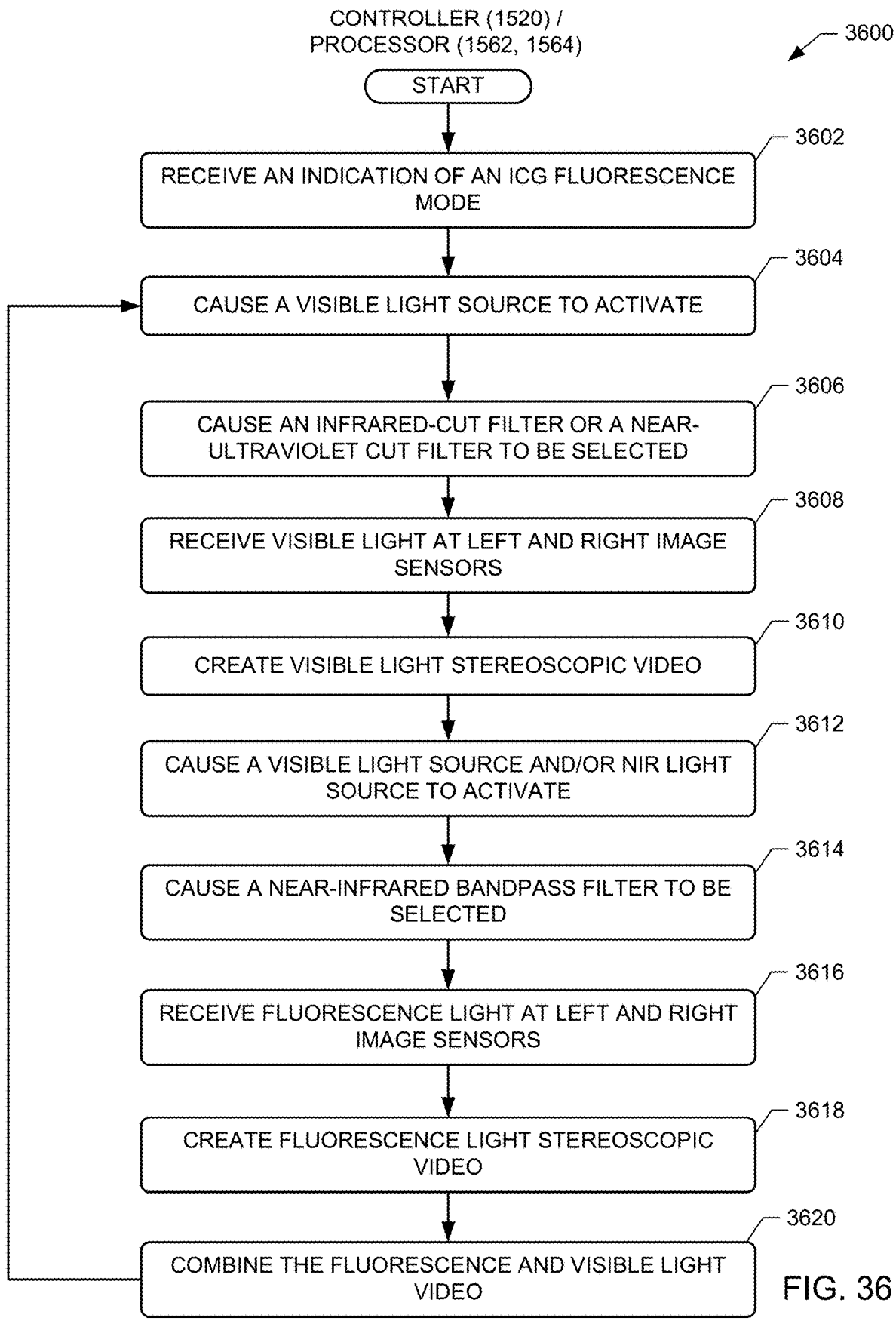
FIG. 36 shows a diagram of an example procedure for providing a live stereoscopic view of visible light and ICG fluorescence at the same time, according to an example embodiment of the present disclosure.

In some embodiments, the motor and lighting controller 1520 and/or the processor 1562 is configured to display a live stereoscopic view of visible light and ICG fluorescence at the same time. In these embodiments, the motor and lighting controller 1520 and/or the processor 1562 is configured to synchronize the filter assembly 740 to rotate between alternative positions for a first filter and a second filter as the light sources are activated. FIG. 36 shows a diagram of an example procedure 3600 for providing a live stereoscopic view of visible light and ICG fluorescence at the same time, according to an example embodiment of the present disclosure. The example procedure 3600 may be defined by one or more instructions stored in the memory 1524 and/or the memory 1570. The instructions are executable by the motor and lighting controller 1520 and/or the processor 1562 to perform the operations disclosed herein. It should be appreciated that in some embodiments, the other of the blocks may be different, certain blocks may be omitted, and/or blocks may be added.

The example procedure 3600 begins when the motor and lighting controller 1520 and/or the processor 1562 receives an indication that an ICG fluorescence mode of the stereoscopic visualization camera 300 has been activated by an operator (block 3602). The indication may include a message or signal from, for example, the input device 1410 of FIGS. 14 and 15. As described herein, the ICG fluorescence mode includes superimposing fluorescence graphics from a fluorescence scene onto a visible light scene during a visible light mode. To acquire one or more video frames or signals for the visible light scene, the motor and lighting controller 1520 and/or the processor 1562 causes the visible light source 708a to be activated (block 3604) and causes the filter assembly 740 to rotate to the infrared cut filter or the near-ultraviolet cut filter (block 3606). During this time, visible light is reflected from a surgical site 700 and received at the image sensors 746 and 748, which convert the received light to image data (block 3608). The processor 1562 and/or a graphics processing unit 1564 then combine the left and right image data into stereoscopic video signals and/or video data for display on a monitor as the visible light scene (block 3610). The motor and lighting controller 1520 and/or the processor 1562 continues to remain in the visible light mode for at least the exposure time for one frame.

At a designated time, the motor and lighting controller 1520 and/or the processor 1562 acquires one or more video frames or signals for the fluorescence light scene by switching to a fluorescence mode. The motor and lighting controller 1520 and/or the processor 1562 switches from visible light mode to fluorescence mode by causing at least one of the visible light source 708a and/or the NIR light source 708b to be activated (block 3612) and causes the filter assembly 740 to rotate to the ICG emissions filter (e.g., the near-infrared bandpass filter) (block 3614). The switching of modes may be performed during a blanking time of the image sensors 746 and 748. During the fluorescence mode, mixed excitation and emissions light is reflected from a surgical site 700 and filtered to ICG emission light, which is received at the image sensors 746 and 748 for conversion to image data (block 3616). The processor 1562 and/or the graphics processing unit 1564 then combine the left and right image data into stereoscopic video signals and/or video data as the fluorescence light scene (block 3618). The processor 1562 and/or the graphics processing unit 1564 may visualize the areas in the video image that correspond to fluorescence light by applying at least one graphic or changing pixel colors to a light wavelength that is viewable to an operator. The motor and lighting controller 1520 and/or the processor 1562 continues to remain in the fluorescence light mode for at least the exposure time for one frame.

The processor 1562 and/or the graphics processing unit 1564 is also configured to combine the fluorescence video with the visible light video. In some embodiments, this includes overlaying the fluorescence video frame on top of the visible light video frames (e.g., combining the separate visible and fluorescence images into a single image by laying the fluorescence image over the visible image). In other embodiments, the processor 1562 and/or the graphics processing unit 1564 is configured to extract the portions of the fluorescence video frame (or the created fluorescence graphics) that comprise fluorescence portions, identify corresponding locations in the visible light video frames using, for example, shape or feature matching, and superimpose or overlay the fluorescence portions on top of the corresponding visible light portions. The processor 1562 and/or the graphics processing unit 1564 may also use pixel locations in a display coordinate plane such that the pixels from the fluorescence image data are displayed in the same location over the visible light image data. For instance, if a pixel from fluorescence image data is located in an image plane of (45, 92) (corresponding to a pixel color value of fluorescence emission light), the processor 1562 and/or the graphics processing unit 1564 shades the pixel to a color visible to a human operator and overlays or replaces a pixel at the location (45, 92) of the visible light image data with the shaded pixel from the fluorescence image data.

The combined video is then provided for display showing areas of tissue with fluorescence superimposed on the visible video. This configuration provides a surgeon an improved view of the surrounding tissue while also highlighting, for example, fluorescing vessels. After the video signals are displayed, the procedure returns to block 3604 to acquire additional visible video frames. The example procedure 3600 continues until the fluorescence mode is disabled or deactivated.

It should be appreciated that the motor and lighting controller 1520 and/or the processor 1562 may acquire alternating frames in the visible light and fluorescence modes. As such, the video frame rate may be reduced since at least some of the video acquired during the fluorescence mode is combined with the visible light video frames. To improve the frame rate, the ratio of visible light frames to fluorescence light frames may be increased, where, for example, the fluorescence frames provide a sampling of the fluorescence data. For example, the motor and lighting controller 1520 and/or the processor 1562 may be configured to acquire two, three, four, five, etc. visible light frames for every fluorescence light frame acquired. In these embodiments, fluorescence video from one frame is combined with multiple visible video frames.

In some embodiments, the motor and lighting controller 1520 and/or the processor 1562 are configured to provide an option for an operator to view side-by-side fluorescence and visible light views. In some instances, the image may be stereoscopic, where a first video display shows the visible light view, while an adjacent video display shows the fluorescence view. In these instances, the visible light view and fluorescence views are at least one frame apart.

In other examples, the filter assembly 740 may be configured to enable different filters to be selected for the left and right views. For example, the infrared-cut filter or the near-ultraviolent cut filter may be selected for the right optical path to provide visible light to the right image sensor 746 while the near-infrared bandpass filter is selected for the left optical path to provide ICG excitation fluorescence light to the left image sensor 748. In this configuration, the processor 1562 and/or the graphics processing unit 1564 produces two two-dimensional displays, one display being the visible light view and the other being the fluorescence view.

B. 5-Aminolevulinic Acid ("ALA") Embodiment

5-ALA is an amino acid that is orally digested six to eight hours by a patient prior to surgery. After ingestion, 5-ALA is transported in the blood stream throughout the body and is a precursor for Protoporphyrin IX. With 5-ALA, glioblastomas metabolize in higher quantity compared to healthy tissue Protoporphyrin IX, which reacts to light in the spectral range of 300 nm-640 nm, with the strongest sensitivity between 400 nm-415 nm. Reactions between Protoporphyrin IX with 5-ALA and light having wavelengths in the range of 300 nm-640 nm causes or creates a release of photos in the spectral range of 480 nm-800 nm, peaking at 635 nm, with a smaller peak at 705 nm (viewed as a pinkish red glow).

Known microscopes have issues imaging 5-ALA fluorescence light that are similar to the issues for imaging ICG fluorescence light, discussed above. The issues include bulky filters, excessive power consumption/heat generation, inefficient light splitting, and less resolution two-dimensional video.

Figure 37:
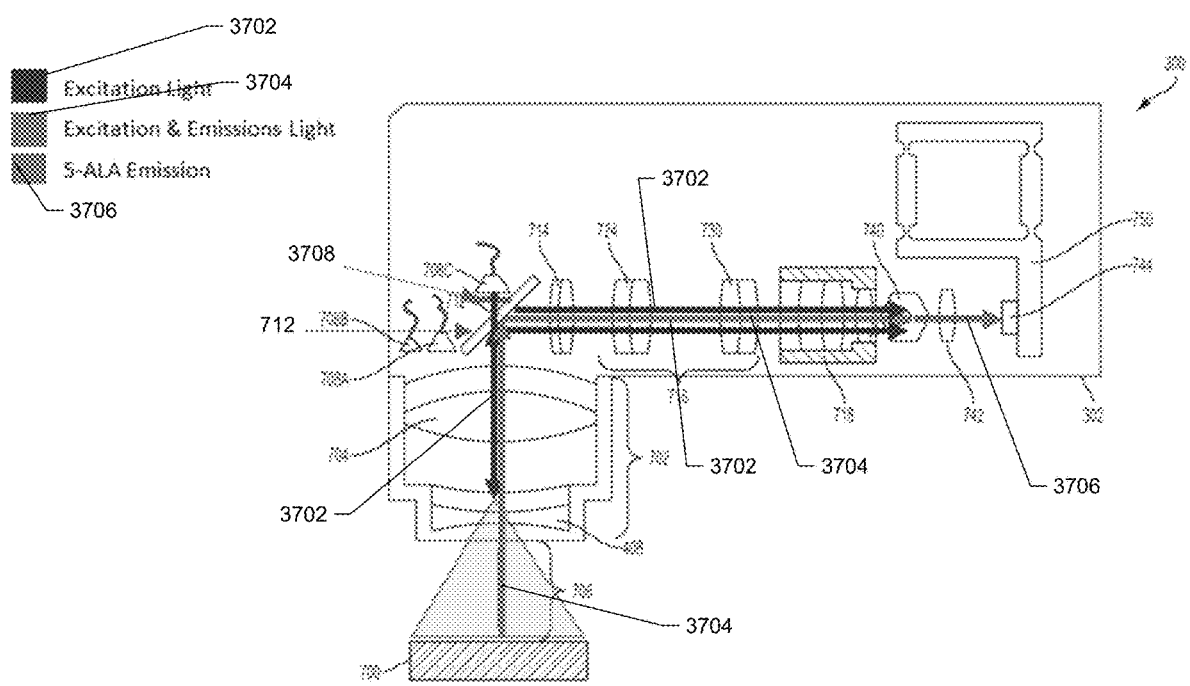
FIG. 37 shows a diagram illustrative of how the stereoscopic visualization camera of FIG. 3 uses a near-ultraviolet ("NUV") light source with a filter assembly for providing light corresponding to 5-aminolevulinic acid ("ALA") emission wavelengths to image sensors, according to an example embodiment of the present disclosure.

The example stereoscopic visualization camera 300 disclosed herein overcomes at least some of the known problems of conventional microscopes by synchronizing light source activation and filter selection to optimize the reception of 5-ALA emission light. FIG. 37 shows an embodiment illustrative of how the stereoscopic visualization camera 300 uses the NUV light source 708c with the filter assembly 740 for providing light corresponding to 5-ALA emission wavelengths to the image sensors 746 and 748, according to an example embodiment of the present disclosure.

In the illustrated example, an operator selects an NUV mode of the stereoscopic visualization camera 300. The operator may select the NUV mode using controls on the arms 304 and/or via an input device 1410. The motor and lighting controller 1520 and/or the processor 1562 of FIG. 15 receives the request for NUV mode and transmits one or more messages or signals to the NUV light driver 1534 for activating the NV light source 708c. The motor and lighting controller 1520 and/or the processor 1562 may also deactivate the other light sources 708a and/or 708b. In addition to activating the NUV light source 708c, the motor and lighting controller 1520 and/or the processor 1562 cause the filter assembly 740 to rotate the left and right filter magazines 3306 to cause near-ultraviolet cut filters to be placed in the left and right optical paths.

Similar to the ICG fluorescence mode, the motor and lighting controller 1520 and/or the processor 1562 use one or more zoom lookup tables to cause the front zoom lens set 724 and/or rear zoom lens set 730 to move along the optical path to maintain focus. The motor and lighting controller 1520 and/or the processor 1562 may also adjust a position of the front working distance lens 408 and/or the rear working distance lens 704 to improve focus for light in the NUV spectrum (e.g., light having a wavelength between 375 nm and 450 nm). Additionally or alternatively, the motor and lighting controller 1520 and/or the processor 1562 may adjust settings of the image sensors 746 and 748 to improve sensitivity to light in the 5-ALA emission wavelength range.

As shown in the illustrated example of FIG. 37, excitation light 3702 transmits through an excitation filter 3708 that is configured to remove a large percentage or portion of the excitation light that is within the same wavelength range as that of the near-ultraviolet cut filters of the filter assembly 740. In other words, the excitation filter 3708 permits light between, for example 300 nm-450 nm (or 380 nm to 450 nm) to pass, corresponding to the peak absorption wavelength range of 5-ALA, while blocking light having wavelengths above 450 nm (and below 380 nm in some embodiments) to prevent contamination with excitation light having a wavelength above 480 nm (e.g., light having a peak emission wavelength of 635 nm). As such, as shown in FIG. 37 any excitation light 3702 that makes its way towards the end of the optical path due to reflections in the main objective assembly 702 (or from the target surgical site 700, shown as exited and emissions light 3704) is blocked by the excitation filter (e.g., the near-ultraviolet cut filter) of the filter assembly 740 so that only 5-ALA emissions light 3706 is received at the image sensors 746 and 748 (collectively optical image sensor 744).

It should be appreciated that the image sensors 746 and 748 of the stereoscopic visualization camera 300 have a greater resolution than UV-specific cameras used as accessories in conventional microscopes. The greater resolution of the image sensors 746 and 748 produces sharper images with move overall detail. Further the use of left and right image sensors 746 and 748 provides three-dimensional images with depth, which enables a surgeon to safely maneuver instruments in the surgical area while viewing the video on the display monitor 512, 514. The maximization of light throughput to the image sensors 746 and 748 enables the stereoscopic visualization camera 300 to use less powerful illumination compared to known microscopes. The use of less light (and power generally) generates less heat at the surgical site, thereby reducing the risk of burning or overheating patient tissue, which reduces the amount of external hydration that needs to be applied to the surgical site. In addition, since the stereoscopic visualization camera 300 cuts off all blue light in the left and right optical paths, the stereoscopic image has higher contrast between a tumor and healthy tissue compared to contrast provided by conventional microscopes.

It should also be appreciated that the light sources 708 of the stereoscopic visualization camera 300 are positioned relative to the main objective assembly 702 to provide semi-coaxial illumination, which increases the amount of light that can reach into deep cavities. As such, the example stereoscopic visualization camera 300 has little or no magnification or working distance restrictions and can visualize 5-ALA fluorescence up to 10× or 20× through the entire working distance between 200 mm-450 mm. The stereoscopic visualization camera 300 provides a wide illumination field by default since the focusing is performed by the main objective assembly 702 and/or the zoom assembly 716 rather than in independent optics found in known conventional microscopes.

In some embodiments, the stereoscopic visualization camera 300 is configured to provide back-illumination using visible light while visualizing 5-ALA emission light for viewing of surrounding tissue and tools from a tumor. In known conventional microscopes, when a surgeon is viewing 5-ALA emission light, the surrounding areas that are not emitting light are completely dark, making it very difficult for the surgeon to introduce or move their instrument at the target surgical site. The stereoscopic visualization camera 300 may switch between the visible light source 708*a* and the NUV light source 708*c* while having the near-ultraviolet cut filter of the filter assembly 740 engaged with the optical paths. The stereoscopic visualization camera 300 may alternatively activate the visible light source 708*a* at the same time as the NUV light source 708*c*. While the light sources 708*a* and 708*b* are respectively activated, the image sensors 746 and 748 record the 5-ALA emission light for stereoscopic display. In this manner, the addition of the visible spectrum light enables the surgeon to see surrounding tissue while still being able to view the fluorescing tumor in real time via the stereoscopic visualization on the display monitor 512 and 514.

Figure 38:
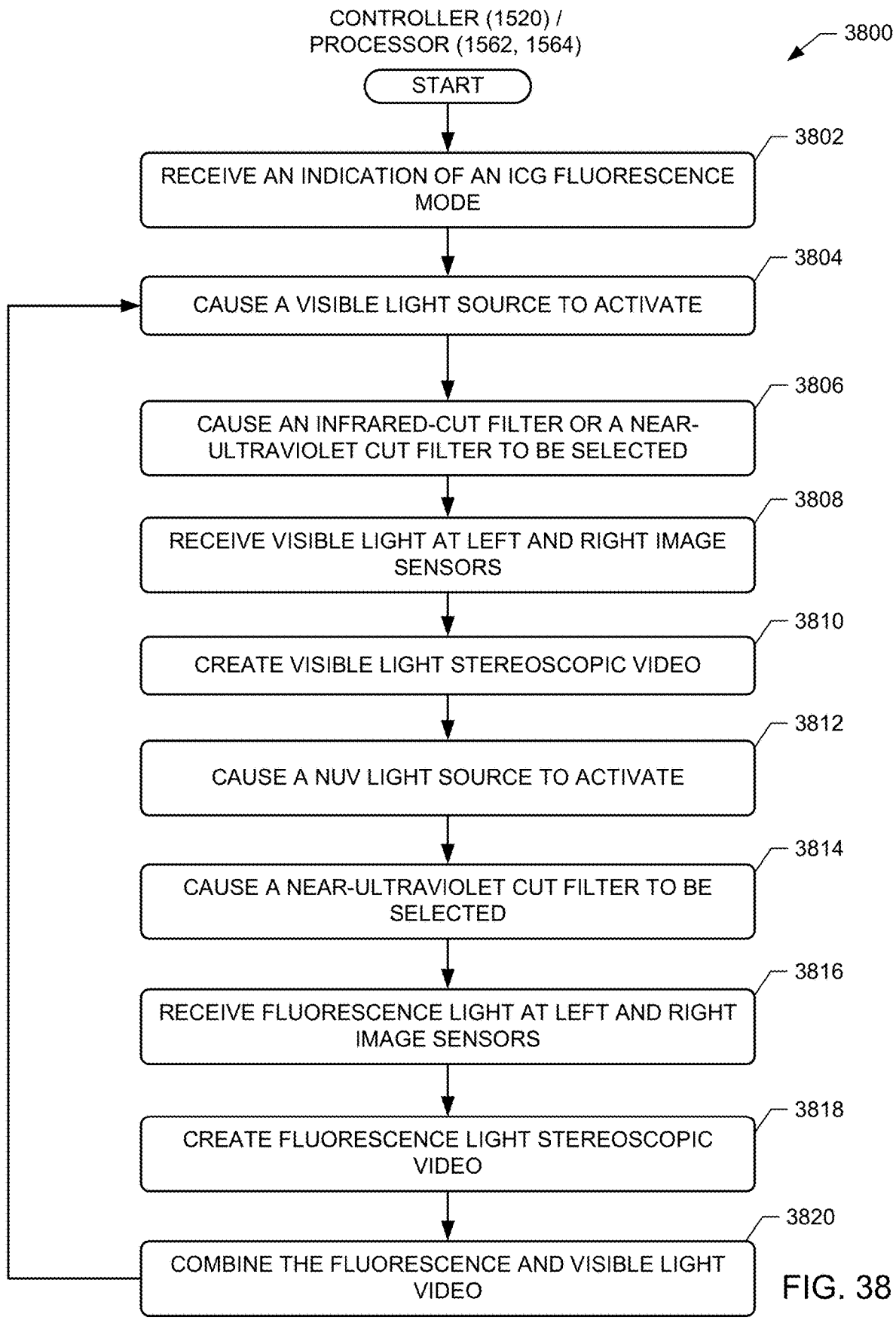
FIG. 38 shows a diagram of an example procedure for providing a live stereoscopic view of visible light and 5-ALA fluorescence at the same time, according to an example embodiment of the present disclosure.

In some embodiments, the motor and lighting controller 1520 and/or the processor 1562 is configured to display a live stereoscopic view of visible light and 5-ALA fluorescence at the same time. In these embodiments, the motor and lighting controller 1520 and/or the processor 1562 is configured to synchronize the filter assembly 740 to rotate between alternative positions for a first filter and a second filter as the light sources are activated. FIG. 38 shows a diagram of an example procedure 3800 for providing a live stereoscopic view of visible light and 5-ALA fluorescence at the same time, according to an example embodiment of the present disclosure. The example procedure 3800 may be defined by one or more instructions stored in the memory 1524 and/or the memory 1570. The instructions are executable by the motor and lighting controller 1520 and/or the processor 1562 to perform the operations disclosed herein. It should be appreciated that in some embodiments, the other of the blocks may be different, certain blocks may be omitted, and/or blocks may be added.

The example procedure 3800 begins when the motor and lighting controller 1520 and/or the processor 1562 receives an indication that a 5-ALA fluorescence mode of the stereoscopic visualization camera 300 has been activated by an operator (block 3802). The indication may include a message or signal from, for example, the input device 1410 of FIGS. 14 and 15. As described herein, the 5-ALA fluorescence mode includes superimposing fluorescence graphics from a fluorescence scene onto a visible light scene during a visible light mode. To acquire one or more video frames or signals for the visible light scene, the motor and lighting controller 1520 and/or the processor 1562 causes the visible light source 708*a* to be activated (block 3804) and causes the filter assembly 740 to rotate to the infrared cut filter or the near-ultraviolet cut filter (block 3806). During this time, visible light is reflected from a surgical site 700 and received at the image sensors 746 and 748, which convert the received light to image data (block 3808). The processor 1562 and/or a graphics processing unit 1564 then combine the left and right image data into stereoscopic video signals and/or video data for display on a monitor as the visible light scene (block 3810). The motor and lighting controller 1520 and/or the processor 1562 continues to remain in the visible light mode for at least the exposure time for one frame.

At a designated time, the motor and lighting controller 1520 and/or the processor 1562 acquires one or more video frames or signals for the fluorescence light scene by switching to a fluorescence mode. The motor and lighting controller 1520 and/or the processor 1562 switches from visible light mode to 5-ALA fluorescence mode by causing the NUV light source 708*c* to be activated (block 3812) and causes the filter assembly 740 to rotate to the 5-ALA emissions filter (e.g., the near-ultraviolet cut filter) (block 3814). The switching of modes may be performed during a blanking time of the image sensors 746 and 748. During the fluorescence mode, mixed excitation and emissions light is reflected from a surgical site 700 and filtered to 5-ALA emission light, which is received at the image sensors 746 and 748 for conversion to image data (block 3816). The processor 1562 and/or the graphics processing unit 1564 then combine the left and right image data into stereoscopic video signals and/or video data as the fluorescence light scene (block 3818). The processor 1562 and/or the graphics processing unit 1564 may visualize the areas in the video image that correspond to fluorescence light by applying at least one graphic or changing pixel colors to a light wavelength that is viewable to an operator. The motor and lighting controller 1520 and/or the processor 1562 continues to remain in the fluorescence light mode for at least the exposure time for one frame.

It should be appreciated that due to the peak emission wavelength of 5-ALA being in the 635 nm range, the red pixels of the image sensors 746 and 748 that are capturing the emitted photons have higher outputs compared to other pixels. The small change in values can be identified by the processor 1562 and/or the graphics processing unit 1564 via image processing for accentuating the difference by overlying brighter colors over the slightly hotter pixels. This enables the fluorescence emission to be clearly visible to an operator, thereby providing for the imaging of any glioblastoma in the patient. This enables a surgeon to remove more of a patient's tumor than is otherwise possible to help increase the life expectancy of the patient.

The processor 1562 and/or the graphics processing unit 1564 is also configured to combine the fluorescence video with the visible light video. In some embodiments, this includes overlaying the fluorescence video frame on top of the visible light video frames (e.g., combining the separate visible and fluorescence images into a single image by laying the fluorescence image over the visible image). In other embodiments, the processor 1562 and/or the graphics processing unit 1564 is configured to extract the portions of the fluorescence video frame (or the created fluorescence graphics) that comprise fluorescence portions, identify corresponding locations in the visible light video frames using, for example, shape or feature matching, and superimpose or overlay the fluorescence portions on top of the corresponding visible light portions. The combined video is then provided for display showing areas of tissue with fluorescence superimposed on the visible video. This configuration provides a surgeon an improved view of the surrounding tissue while also highlighting, for example, fluorescing tumors. After the video signals are displayed, the procedure returns to block 3804 to acquire additional visible video frames. The example procedure 3800 continues until the 5-ALA fluorescence mode is disabled or deactivated.

Similar to ICG fluorescence discussed above, the motor and lighting controller 1520 and/or the processor 1562 may acquire alternating frames in the visible light and fluorescence modes at virtually any ratio. In addition, the motor and lighting controller 1520 and/or the processor 1562 are configured to provide an option for an operator to view side-by-side fluorescence and visible light views. Further, the infrared-cut filter or the near-ultraviolent cut filter may be selected for the right optical path to provide visible light to the right image sensor 746 while the near-ultraviolent cut filter is selected for the left optical path to provide 5-ALA excitation fluorescence light to the left image sensor 748. In this configuration, the processor 1562 and/or the graphics processing unit 1564 produces two two-dimensional displays, one display being the visible light view and the other being the 5-ALA fluorescence view.

CONCLUSION

It will be appreciated that each of the systems, structures, methods and procedures described herein may be implemented using one or more computer programs or components. These programs and components may be provided as a series of computer instructions on any conventional computer-readable medium, including random access memory ("RAM"), read only memory ("ROM"), flash memory, magnetic or optical disks, optical memory, or other storage media, and combinations and derivatives thereof. The instructions may be configured to be executed by a processor, which when executing the series of computer instructions performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims. Moreover, consistent with current U.S. law, it should be appreciated that 35 U.S.C. 112(f) or pre-AIA 35 U.S.C. 112, paragraph 6 is not intended to be invoked unless the terms "means" or "step" are explicitly recited in the claims. Accordingly, the claims are not meant to be limited to the corresponding structure, material, or actions described in the specification or equivalents thereof.

The invention is claimed as follows:

1. A stereoscopic imaging apparatus comprising: a main objective assembly configured to change a working distance along an optical axis to a target surgical site; left and right lens sets defining respective parallel left and right optical paths along the optical axis and configured to form the respective optical paths from light that is received from the main objective assembly of the target surgical site; a light filter assembly having left and right filter magazines positioned respectively along the left and right optical paths and configured to selectively enable certain wavelengths of the light to pass through, each of the left and right filter magazines including: an infrared cut filter, a near-ultraviolet cut filter, and a near-infrared bandpass filter; left and right image sensors configured to receive the filtered light and convert the filtered light into image data that is indicative of the received filtered light; a processor communicatively coupled to the left and right image sensors and configured to convert the image data into stereoscopic video signals or video data for display on a display monitor; a visible light source positioned to transmit visible light to the target surgical site; a near-infrared light source positioned to transmit near-infrared light to the target surgical site; an excitation filter positioned in front of the near-infrared light source and configured to enable light at indocyanine green ("ICG") fluorescence absorption wavelengths to pass through; and a controller configured to: provide a visible light mode by causing the visible light reflected from the target surgical site to be provided to the left and right image sensors by activating the visible light source and selecting at least one of the infrared cut filter or the near-ultraviolet cut filter to be placed in the respective optical path, provide an ICG fluorescence mode by causing ICG fluorescence emission light from the target surgical site to be provided to the left and right image sensors by activating at least one of the visible light source or the near-infrared light source and selecting the near-infrared bandpass filter to be placed in the respective optical path, and switch between the visible light mode and the ICG mode to enable the processor to provide stereoscopic video signals or video data with at least some image data corresponding to the ICG fluorescence emission light to be superimposed on image data corresponding to the visible light.

2. The imaging apparatus of claim 1, wherein the left and right filter magazines each include six sides where a first two parallel sides each include the infrared cut filter, a second two parallel sides each include the near-ultraviolet cut filter, and a third two parallel sides each include the near-infrared bandpass filter.

3. The imaging apparatus of claim 1, wherein the left and right filter magazines each include six sides where a first side includes the infrared cut filter, a second side includes the near-ultraviolet cut filter, and a third side includes the near-infrared bandpass filter.

4. The imaging apparatus of claim 1, wherein the filter assembly includes an axle configured to connect to the left and right filter magazines and mechanically connect to a motor controlled by the controller for rotating each of the left and right filter magazines.

5. The imaging apparatus of claim 1, wherein the excitation filter is configured to enable light between a wavelength of 710 nanometers ("nm") and 822 nm to pass through, corresponding to the ICG fluorescence absorption wavelengths, and wherein the near-infrared bandpass filter is configured to enable light between a wavelength of 817 nm and 900 nm to pass through, corresponding to the ICG fluorescence emission light.

6. The imaging apparatus of claim 1, wherein the processor is configured to: identify the image data corresponding to the ICG fluorescence emission light based on pixel color values; and apply a pixel color that is visible to an operator to the identified pixels for superimposing on the image data corresponding to the visible light.

7. The imaging apparatus of claim 1, wherein the controller is configured to switch between the visible light mode and the ICG fluorescence mode during a blanking period of the left and right image sensors.

8. The imaging apparatus of claim 1, wherein the controller is configured to select the visible light mode for at least one of one, two, three, four, or five consecutive video frames for the stereoscopic video signals or the video data corresponding to the visible light.

9. The imaging apparatus of claim 8, wherein the controller is configured to select the ICG fluorescence mode for at least one of one, two, three, four, or five consecutive video frames for the stereoscopic video signals or the video data corresponding to the ICG fluorescence emission light.

10. The imaging apparatus of claim 9, wherein the processor is configured to superimpose one video frame, the stereoscopic video signals, or the video data corresponding to the ICG fluorescence emission light on more than one frame, the stereoscopic video signals, or the video data corresponding to the visible light.

11. The imaging apparatus of claim 1, further comprising a deflecting element that is located between the main objective assembly and the left and right lens sets, the deflecting element configured to reflect the light received from the main objective assembly to the left and right lens sets, wherein the deflecting element is coated or configured to reflect only light wavelengths that are beyond the near-ultraviolet light wavelengths range to enable light having near-ultraviolet light wavelengths from the near-ultraviolet light source to pass through the deflecting element to the main objective assembly.

12. The imaging apparatus of claim 1, further comprising: a near-ultraviolet ("NUV") light source positioned to transmit NUV light to the target surgical site; and a NUV excitation filter positioned in front of the NUV light source and configured to enable light at a 5-aminolevulinic acid ("ALA") fluorescence absorption wavelengths to pass through, wherein the controller is configured to: provide a 5-ALA fluorescence mode by causing 5-ALA fluorescence emission light from the target surgical site to be provided to the left and right image sensors by activating the NUV light source and selecting the near-ultraviolet cut filter to be placed in the respective optical path, and interchangeably switch between the visible light mode and the 5-ALA mode to enable the processor to provide stereoscopic video signals or video data with at least some image data corresponding to the 5-ALA fluorescence emission light to be superimposed on image data corresponding to the visible light.

* * * * *